United States Patent [19]
Siiman et al.

[11] Patent Number: 5,814,468
[45] Date of Patent: Sep. 29, 1998

[54] METHODS OF ENUMERATING RECEPTOR MOLECULES FOR SPECIFIC BINDING PARTNERS ON FORMED BODIES AND IN SOLUTION

[75] Inventors: Olavi Siiman, Davie; Alexander Burshteyn, Hialeah; Orlando Concepcion, Miramar; Meryl Forman, Miami, all of Fla.

[73] Assignee: Coulter International Corp., Miami, Fla.

[21] Appl. No.: 624,014

[22] Filed: Mar. 27, 1996

[51] Int. Cl.⁶ ............................. G01N 33/533; C12Q 1/70
[52] U.S. Cl. ............................ 435/7.21; 435/5; 435/7.32; 435/7.93
[58] Field of Search ............................. 435/5, 7.21, 7.32, 435/7.93, 968

[56] References Cited

U.S. PATENT DOCUMENTS

| | | | |
|---|---|---|---|
| 4,338,024 | 7/1982 | Bolz et al. | 356/23 |
| 4,476,231 | 10/1984 | Deindoerfer et al. | 436/534 |
| 4,665,020 | 5/1987 | Saunders | 435/7.4 |
| 4,752,563 | 6/1988 | Kortright et al. | 435/2 |
| 4,931,395 | 6/1990 | Griffin | 530/388.7 |
| 5,169,754 | 12/1992 | Siiman et al. | 435/5 |
| 5,342,754 | 8/1994 | Maples et al. | 435/2 |
| 5,527,713 | 6/1996 | Bolton et al. | 436/529 |

OTHER PUBLICATIONS

Abramson, J.S. and Wheeler, J.G. (Eds.), *The Neutrophil*, IRL Press at Oxford University Press, 1993, Table of Contents and Introduction.

Adamson, A.W., *Physical Chemistry of Surfaces*, Fourth Edition, Wiley–Interscience Publication, John Wiley & Sons, New York, 1982, pp. ix–xviii.

Barclay, A.N. et al., *The Leucocyte Antigen Facts Book*, Academic Press, Harcourt Brace Jovanovich, San Diego, 1993, p. 21.

Bennett, C.A. and Franklin, N.L., *Statistical Analysis in Chemistry and the Chemical Industry*, John Wiley & Sons, New York, 1967, pp. 15, 91.

Bohn, B., High–Sensitivity Cytofluorometric Quantitation of Lectin and Hormone Binding to Surfaces of Living Cells, *Exp. Cell Res.*, 103:39–46 (1976).

Bohn, B. et al., Application of Flow Cytofluorometry to Ligand Binding Studies on Living Cells: Practical Aspects and Recommendations for Calibration and Data Processing, *Flow Cytometry* IV: 227–232 (1980).

Bohn, B., Flow Cytometry: A Novel Approach for the Quantitative Analysis of Receptor–Ligand Interactions . . . Living Cells, *Molec. Cell. Endocrinol.*, 20:1–15 (1980).

Davies, D.R. et al., Antibody Structure, *Acc. Chem. Res.*, 26:421–427 (1993).

Dawson, H.M., A Method for Investigating Dissociation Equilibria . . . Potassium Mercuriiodide Solutions, *J. Chem. Soc.*, 95:870 (1909); *Chem. Abstr.*, 3:2080 (1909).

Edwards, S.W., *Biochemistry and Physiology of the Neutrophil*, Cambridge University Press, 1994, pp. v–xi.

Farr, R.S., A Quantitative Immunochemical Measure of the Primary Interaction Between I*BSA and Antibody, *J. Infect. Dis.*, 103:239 (1958).

Fleit, H.B. et al., A Soluble Form of FcγRIII Is Present in Human Serum and Other Body Fluids and Is Elevated at Sites of Inflammation, *Blood*, 79(10):2721–2728 (1992).

*Fluorescent Microbead Standards*, Flow Cytometry Standards Corporation, Research Triangle Park, NC (1988), pp. i–iii.

Fulwyler, M.J., Standards for Flow Cytometry, *Flow Cytometry and Sorting*, M.R. Melamed, P.F. Mullaney, M.L. Mendelsohn (Eds.), John Wiley & Sons, New York, pp. 351–358, 1979.

Harlow, E. et al., *Antibodies—A Laboratory Manual*, Chapter 14 Immunoassays, Cold Spring Harbor Laboratory, 1988, pp. iii–ix and 553–569.

Hiemenz, P.C., *Principles of Colloid and Surface Chemistry*, Second Edition, Marcel Dekker, Inc., New York, 1986, pp. ix–xiv.

Huizinga, T.W.J. et al., Soluble Fcγ Receptor III in Human Plasma Originates from Release by Neutrophils, *J. Clin. Invest.*, 86:416–423 (1990).

Janin, J. et al., The Structure of Protein—Protein Recognition Sites, *J. Biol. Chem.*, 265(27):16027–16030 (1990).

Karlsson, R. et al., Kinetic analysis of monoclonal antibody–antigen interactions with a new biosensor based analytical system, *J. Immunol. Methods*, 145:229–240 (1991).

Lepp, A. et al., Surface Raman Investigation of the Sorption of Dabsyl Aspartate and Polyvinylpyrrolidone on Colloidal Silver in Ethanol, *J. Coll. Interface Sci.*, 105(2):325–341 (1985).

Lisi, P.J. et al., A fluorescence immunoassay for soluble antigens employing flow cytometric detection, *Clinica Chimica Acta*, 120:171–179 (1982).

(List continued on next page.)

Primary Examiner—Marian C. Knode
Assistant Examiner—Donna C. Wortman
Attorney, Agent, or Firm—Michelle A. Kaye

[57] ABSTRACT

This invention relates generally to using fluorescent markers (labelled antibodies) and flow cytometry to enumerate the average number of receptors (antigen) on formed bodies (cells) in whole blood, and to evaluate the specific binding constant of the marker for the particular receptors. Mean channel fluorescence intensities of equilibrated marker-cell suspension mixtures, total concentrations of marker, and targeted cell counts obtained by established procedures are used to complete the analyses. The invention further describes a competitive binding assay between marker and unlabelled antibody for receptors shed from the surface of formed bodies into solution and receptors on the formed bodies to analyze for receptors in solution. Moreover, competitive binding assays between marker and unlabelled antibody for receptors on formed bodies in whole blood are described for determination of relative, specific, and average binding constants of unlabelled/labelled antibody for targeted receptors.

45 Claims, 7 Drawing Sheets

OTHER PUBLICATIONS

Muller, R., Calculation of Average Antibody Affinity in Anti–Hapten Sera from Data Obtained by Competitive Radioimmunoassay, *J. Immunol. Methods*, 34:345–352 (1980).

Oonishi, T. et al., Flow cytometric studies of the binding of monoclonal antibodies OKT3, OKT4 and OKT8, *J. Immunol. Methods*, 115:159–167 (1988).

Padlan, E., *Antibody–Antigen Complexes*, R.G. Landes Company, Austin, TX, 1994, pp. 59–76.

Rossotti, F.J.C. et al., *The Determination of Stability Constants*, Chap. 4, Section 4–6, pp. 78–81, McGraw–Hill Book Co., New York, 1961, pp. 58–82.

Saunders, G.C. et al., Amplified Flow–Cytometric Separation–Free Fluorescence Immunoassays, *Clin. Chem.*, 31(12):2020–2023 (1985).

Saunders, G.C. et al., Flow Cytometric Competitive Binding Assay for Determination of Actinomycin–D Concentrations, *Cytometry*, 11:311–313 (1990).

Siiman, O. et al., Surface–Enhanced Raman Scattering by Citrate on Colloidal Silver, *J. Phys. Chem.*, 87:1014–1023 (1983).

Sklar, L.A. et al., Analysis of Ligand–Receptor Interactions with the Fluorescence Activated Cell Sorter, *Cytometry*, 3(3):161–165 (1982).

Steward, M.W. et al., *Antibody Affinity: Thermodynamic Aspects and Biological Significance*, CRC Press, Boca Raton, FL, 1983, Table of Contents.

Tosi, M.F. et al., Surface Expression of Fcγ Receptor III (CD16) on Chemoattractant–stimulated Neutrophils . . . Storage Compartments, *J. Clin. Invest.*, 90:462–470 (1992).

Titus, J.A. et al., Fc(IgG) receptor distributions in homogeneous and heterogeneous cell populations by flow microfluorometry, *Proc. Natl. Acad. Sci. USA*, 78(1):519–523 (1981).

Visser, J. et al., Quantitative Immunofluorescence in Flow Cytometry, in *Immunofluoroescence and Related Staining Techniques*, W. Knapp, K. Holubat, G. Wick (Eds.), Elsevier, Amsterdam, pp. 147–159, 1978.

Vogt, R.F. Jr. et al., Interlaboratory Study of Cellular Fluorscence Intensity Measurements With Fluorescein–Labeled Microbead Standards, *Cytometry*, 12:525–536 (1991).

Voss, E.W. Jr. (Ed.), *Fluorescein Hapten: An Immunological Probe*, CRC Press, Boca Raton, FL, 1984, Table of Contents.

Whitehurst, C.E. et al., Sugar competition assays reveal high affinity receptors for *Erythrina cristagalli* lectin on feline monocytes, *J. Immunol. Methods*, 131:15–24 (1990).

Whitehurst, C.E. et al., A method of purifying feline T lymphocytes from peripheral blood using the plant lectin from *Pisum sativum*, *J. Immunol. Methods*, 175:189–199 (1994).

Wyman, J. Jr., Linked Functions and Reciprocal Effects in Hemoglobin: A Second Look, *Adv. Protein Chem.*, 19:223–286 (1964).

Yalow, R.S., Radioimmunoassay: A Probe for the Fine Structure of Biologic Systems, *Science*, 200:1236–1245 (1978).

METHODS OF ENUMERATING RECEPTOR MOLECULES FOR SPECIFIC BINDING PARTNERS ON FORMED BODIES AND IN SOLUTION

FIELD OF THE INVENTION

The present invention relates to a method for enumerating receptors on a formed body. The invention also relates to a method of evaluating the specific binding constant of labelled ligand (marker) for targeted receptors. The invention further relates to a method of analyzing for receptors released from the surface of formed bodies into a solution, and determining the relative, specific and average binding constants of unlabelled/labelled ligand for targeted receptors.

BACKGROUND OF THE INVENTION

Identification and enumeration of receptors on the surface of formed bodies are important because (a) the receptor type and frequency define the antigenic presentation of a cell to its environment; (b) the receptor type and frequency determine whether the receptor can be easily detected by conventional means, i.e., flow cytometry, or whether additional amplification methods are needed (e.g. enzyme and color development in chromophoric substrate); (c) shedding of receptors can be a symptom of disease or state of activation of a cell; and (d) receptor type and frequency can define subsets of major cell classifications, e.g., other than size and shape of whole blood cells. Thus, one of the major objectives in the field of cell research is the identification and quantitation of surface receptors on formed bodies. Thus, goals for such quantitative investigations are: (a) determination of the number of cell surface receptor molecules (binding sites) for ligands; (b) determination of specific binding constants of labelled/unlabelled ligand for receptors; and (c) determination of the association and dissociation constants of a ligand for its receptors.

In characterizing (enumerating and evaluating the binding constant) receptors on the surface of biological cells, determination of the number of receptors per cell has involved equilibration of labelled ligand with a cell suspension and then a separation of bound from unbound ligands, i.e., a wash step to remove free unbound ligands from the cells [1, 2, 3]. The separation step is required to obtain the solution concentration of ligand, for graphical analysis. Analysis of the steady state binding of ligand to receptor(s) was done by construction of a single reciprocal plot (Scatchard) or double reciprocal graphical analysis.

Alternatively, additional analysis of the binding of radio-labelled ($^{125}$I -labelled antibody) ligand together with fluorescent antibody binding was required to enumerate receptors per cell, or an external standard was used for calibration of fluorescence intensities [4, 5, 6, 7]. Another method using image analysis has been recently suggested as a way of measuring the distribution of a reagent between particles and a liquid [8, 9]. This method does not present an analytical method for enumerating reagent binding sites on the particles or determining the specific binding constant of reagent for sites on the particles.

The general characteristics of soluble antigen-antibody and hapten-antibody binding have been surveyed in two references [10, 11]. Competitive binding experiments of unlabelled and labelled ligand such as antigen or hapten with antibody as a sensitive determination of the amount of unknown ligand in a sample are not new when the label contains a radioactive element and an RIA (radioimmunoassay) is involved [12, 13]. Flow cytometric detection has been used in competitive binding immunoassays with coated microspheres introduced as extraneous supports [14, 15, 16, 17]. In addition, flow cytometry has been used to study competitive binding of fluorescence-labelled lectin and unlabelled sugars on feline mononuclear cells or feline peripheral blood lymphocytes [18, 19]. However, the use of flow cytometry to analyze quantitatively for antigen in solution in a competitive binding experiment of unlabelled and labelled ligand with unknown amounts of both antigen in solution and on cell surfaces, has never been suggested.

SUMMARY OF THE INVENTION

Herein we describe a new method for analyzing the steady state binding of fluorescent ligand to its complementary antigenic receptor on cell surfaces by flow cytometry without the previously required separation step or use of an external standard. The preferred method of the present invention involves mixing and equilibrating various titers of fluorescent ligand with a fixed number of cells in whole blood, fixing the cells by lysing red blood cells and quenching (Q-PREPing) them, running the fixed cells on a conventional flow cytometer, and analyzing the results. The method embodying the invention can be utilized with a variety of immunological reactions, such as immunological reactions involving ligands and formed bodies or cells. The cells or formed bodies suitably labelled, can be expected to be optically identified by the method of the invention in the same manner as the human blood cell examples.

Also described is a new method of obtaining: (1) the amount of soluble antigen in a sample, by determining the unlabelled ligand concentration at which the fluorescence intensity of labelled ligand in the competitive binding experiment with variable titers of unlabelled ligand and fixed titer of labelled ligand mixed with whole blood (and lysed and quenched) matches the fluorescence intensity of a control with no unlabelled ligand; (2) the suitability of labelled antibodies as cell surface markers as indicated by pairwise, relative affinity constants, and (3) the specific binding constant of unlabelled ligand and the average binding constant of unlabelled/labelled ligand to cell surface receptor, when the specific binding constant of labelled ligand has been established by other means.

Thus, it is an object of the present invention to provide a method for the enumeration of receptors on formed bodies wherein the receptors are capable of binding to a marker, wherein a fixed number of formed bodies are mixed with variable amounts of marker for a sufficient period of time and the mixtures are then analyzed with a flow cytometer.

It is an object of the present invention to provide a method for the enumeration of receptors which method does not require elaborate washing steps or the separation of cells from the solution in order to arrive at the result.

Another object of the present invention is to use the mean channel fluorescent (or enhanced Raman) intensities obtained for the marked formed bodies spanning the range of receptor occupancy from about $\frac{1}{100}$ to about 100% of saturation (saturation being defined as all receptors sites filled by labelled ligand) to enumerate the number of receptors per formed body and to evaluate the specific binding constant of labelled ligand for receptors without any separation of bound from unbound marker or further determination of the formed body concentration dependence of marker intensity.

A further object of the present invention is a method that utilizes flow cytometric data from a competitive binding experiment, in which titers of unlabelled ligand and fixed amount of labelled ligand are sufficiently mixed with a suspension of formed bodies, to analyze for receptors that have been released from the surface of the formed bodies into solution.

A further object of the present invention is a method that utilizes flow cytometric data from a competitive binding experiment, in which titers of unlabelled ligand and fixed amount of labelled ligand are sufficiently mixed with a suspension of formed bodies, to determine the relative binding constant for unlabelled/labelled ligand, the specific binding constant for unlabelled ligand, and average binding constants for unlabelled/labelled ligand.

Another object of the present invention is to provide a method wherein the label is fluorescent, such as fluorescein isothiocyanate (FITC) or phycoerythrin (PE).

Another object of the present invention is to provide a method wherein the label is an enhanced Raman one.

Another object of the present invention is to provide a method wherein the ligand is a binding partner, preferably monoclonal antibody, lectin, hormone, growth factor, or drug that is incubated with a fixed volume of a suspension of formed bodies.

Yet another object of the present invention is to provide a method wherein the formed bodies are biological cells, bacteria, viruses, parasites, or suitable colloidal particles that have receptors on their surface for the ligand.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

In FIG. 1, circles denote unconjugated beads, crosses denote anti-1D3 conjugated beads, and squares denote anti-KC16 conjugated beads.

In FIG. 2 circles denote sample, 3G8-FITC and whole blood; crosses denote sample blocked with unlabelled anti-1D3 antibody.

In FIG. 5, circles denote 1D3-FITC/1D3 run 1; triangles denote 1D3-FITC/1D3 run 3; crosses denote KC48-FITC\KC48, and hexagons denote 3G8-FITC\3G8.

In FIG. 7, circles denote donor 1, squares denote donor 2, triangles denote donor 3, and crosses denote donor 4.

DETAILED DESCRIPTION OF THE INVENTION

Figure 1:
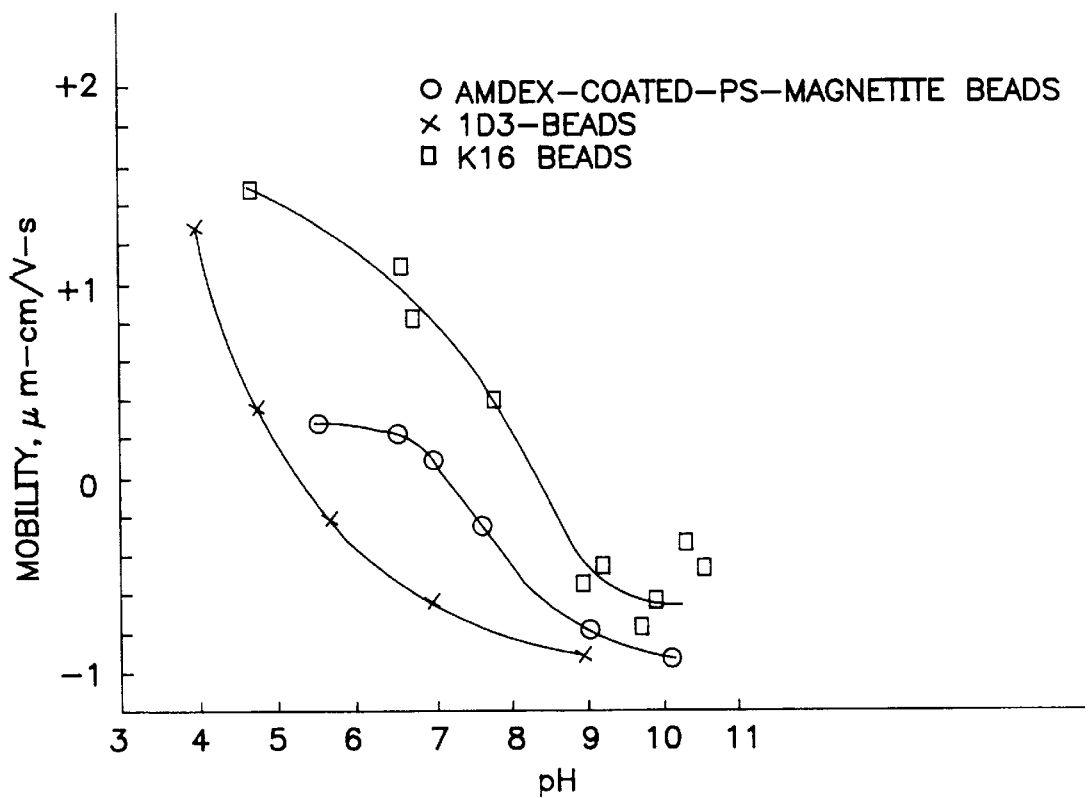
FIG. 1 graphically illustrates the dependence of the electrophoretic mobility of aminodextran-coated polystyrene-magnetite latex beads on pH of the suspension of beads.

While the present invention is satisfied by embodiments in many different forms, herein will be described in detail a particular embodiment of the invention, with the understanding that the following description is to be considered as exemplary of the principles of the invention and is not intended to limit the scope of the invention as determined by the appended claims and their equivalent.

All of the monoclonal antibodies (Ab) referred to herein are identifying designations used by Coulter Corporation, Miami, Fla. for monoclonal antibodies made by Coulter Corporation. The following information further identifies the antibodies used herein. The use of these monoclonal antibodies is by way of example only and is not to be understood as limiting the invention. The term "CD" refers to "Cluster Designation" adopted by the International Workshops on Human Leukocyte Differentiation Antigens. A.T.C.C. is the American Type Culture Collection, Rockville, Md.

| Antibody | CD | Description or Reference |
|---|---|---|
| T3 | CD3 (IgG1) | Derived from the hybridization of mouse P3/NS1/1-AG4-1 myeloma cells with spleen cells from BALB/c mice immunized with human infant thymocytes and peripheral blood lymphocytes from a patient with Sezary cell leukemia. |
| T4 | CD4 | Derived from hybridization of mouse NS/1-AG4 cells with spleen cells of BALB/cJ mice immunized with human peripheral blood T lymphocytes. |
| T8 | CD8 | As T4, but immunized with human thymocytes. |
| KC16 | — | U.S. Pat. No. 4,752,563; A.T.C.C. Deposit No. CRL 8994. |
| 3G8 | CD16b | Derived from hybridization of P3U1 mouse myeloma cells with splenocytes from a CD2F1 mouse immunized with human granulocytes. |
| 1D3 | CD16b | U.S. Pat. No. 4,931,395; A.T.C.C. Deposit No. HB 9445. |
| KC48 | CD15 | U.S. Pat. No. 4,865,971; A.T.C.C. Deposit No. 9584. |
| KC56 | CD45 | Derived from hybridization of mouse Sp2/0-AG14 myeloma cells with spleen cells from BALB/c mice immunized with a derivative of the CEM cell line. |

Other reagents used herein and commercially obtainable from Coulter Corporation are: MsIgG1-PE/MsIgG1-FITC: Mouse IgG1-phycoerythrin ("PE")/Mouse IgG1-Fluorescein Isothiocyanate ("FITC"); T3-FITC/T8-PE; T4-PE/T8-FITC; 1D3-FITC/KC56-PE; 3G8-FITC/KC56-PE; and KC48-FITC/KC56-PE. 1×PBS. Dissolve 53.8 g $K_2HPO_4$ in 1.6 L distilled water. Add 12.8 g $KH_2PO_4$ and stir until dissolved. Then dissolve 340 g NaCl in the solution. After all salts are dissolved, add distilled water to make up to 2 L volume and filter through a 0.2 μm filter. The resulting solution is 20×PBS. 1×PBS is prepared by dilution of 1 part 20×PBS with 19 parts distilled water. The 1×PBS solution has a pH in the range 7.1–7.3, typically 7.2, a conductivity in the range of 13,500 to 15,500 μMho-cm$^{-1}$ and is 0.15M in NaCl.

The term "ligand" as used herein and in the claims, refers to a reactant or specific binding partner.

The term "marker" as used herein and in the claims, refers to a ligand having a label attached to it and which is targeted for receptors on formed bodies.

The term "receptor" as used herein and in the claims, refers to a specific binding partner such as an antigen on the surface of a formed body.

The objectives of the present invention may be achieved by the methods of the present invention wherein elaborate washing steps and separation of cells from the solution in order to arrive at the result are eliminated.

The objectives of the present invention are further accomplished by providing a method of obtaining the association constant for the unlabelled ligand and obtaining a numerical figure for the amount of antigen in solution.

The objectives of the present invention are further accomplished by use of the Langmuir equation or equivalent binding equation. The same equation derivable from simple mass action law principles is applicable to covalent binding of ligand to receptor sites that are assumed to be all identical and independent [see for example reference 20 on binding of molecular oxygen]. The Langmuir equation, or equivalent binding equation, is used to calculate the total surface site concentration (saturation) in a sample. The analysis of the binding of molecular species to surfaces such as those of colloidal particles has been treated in the simplest form by the Langmuir equation. In one of its forms, the Langmuir equation may be represented as follows:

$$\theta_2/(1-\theta_2)=Kc$$

wherein $\theta_2$ is the fractional occupation of surface (receptor) sites; K is the binding or association constant; and c represents the solution concentration of binding species (fluorescent marker).

Raman band intensities have been used to evaluate the number of binding sites on a silver particle for dye molecules. In analyzing the surface Raman band intensities of a dye adsorbed non-specifically on colloidal silver particles [21], $\theta_2$ values were obtained from ratios of Raman band intensities at various dye titers to the maximum band intensity at saturation of silver surface by dye. Since $c_{solution}$ was unknown in the experiments it was calculated from the expression $$[\theta_2/(1-\theta_2)]/K=c,$$

by estimating an initial value of the association constant, K. This estimate may be obtained from the slope of the linear, low concentration, portion of a $\theta_2/(1-\theta_2)$ versus $c_{total}$ plot. Since $c_{solution}$ is always less than $c_{total}$ in a binding situation, this estimated K value establishes a lower bound on the true value of the association constant. Subsequently, the surface concentration of dye (or occupied site concentration) could be computed as $$c_{surface}=c_{total}-c,$$

and the saturation concentration of dye on the surface was $$c_{sat}=c_{surface}/\theta_2.$$

The values of $c_{sat}$ for different $c_{total}$ values were compared and the variance was minimized by making small adjustments in the association constant, K. The final average value of $c_{sat}$ can be taken as equivalent to the total surface site concentration in the sample.

The objectives of the present invention are further accomplished by use of competitive binding reaction to calculate the association constants for unlabelled ligand.

The basic thesis of competitive reactions was first expressed by Dawson in 1909 in the following words, "The essential feature of the method consists in the mode of determination of the proportion in which one of the two components of the solution is present in the uncombined condition. This is effected by adding to the solution a third substance which combines with this component to form another complex compound, for which the value of the dissociation constant is known." [22]. Derivation of the first set of equations necessary for analyses of competitive binding equilibria (below) follows the methods described in a classic text on metal-ligand binding [23].

The competitive binding reaction involves one central group, the antigen on the cell surface, and two ligands, unmarked and marked ligand. If only 1:1 complexes are formed, the predominant equilibrium in solutions containing the antigen, and the two ligands may be represented by the ligand exchange reaction, $$RL^*+L<-->RL+L^*$$

wherein R is the antigen on the cell surface; L is the unmarked ligand; and L* is the marked ligand.

The corresponding equilibrium constant, $K_{rel}$, is given by

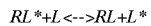

$$K_{rel}=[RL][L^*]/([RL^*][L])=K^L/K^{L^*}.$$

wherein $K_{rel}$ is the equilibrium constant; and $K^L$ ($K^{L^*}$) are association constants between unlabelled (labelled) ligand and receptor. By application of the mass action law to the non-interacting, multiple binding site, R, equilibria, (RL<-->L+)R(+L*<-->RL*), are $K^L=[RL]/([R][L])$ and $K^{L^*}=[RL^*]/([R][L^*])$ for 1:1 complexes.

Thus, if $K_{rel}$ can be determined experimentally, the value of $K^L$ can be calculated, provided that $K^{L^*}$ is known. No knowledge of the free, unbound receptor concentration, [R], is required. The equilibrium concentrations of the various species are related to the total concentrations by the mass-balance equations, $$R=[RL]+[RL^*]+[R]$$

$$L=[RL]+[L]$$

$$L^*=[RL^*]+[L^*]$$

If the ligands, L and L*, are present in excess of R, then R>>[R] and the free receptor concentration may be neglected, provided that the complexes RL and RL* are of high stability. Thus, $$R=[RL]+[RL^*],$$

and if the total receptor concentration, R, is known from another experiment with L*, and either the free concentration of one of the species, [L] or [L*], or the ratio of the concentrations of two species can be measured, then the value of $K_{rel}$ can be found.

The remainder of the analysis that was used herein for competitive antibody reactions with antigen on cell surfaces continued with the expressions for $K_{rel}$. The RIA method [24] elaborated for competitive hapten binding to anti-hapten antibody could not be applied to cases where the affinity constants of unlabelled and labelled analyte, inhibitor and tracer, respectively, were not identical or very nearly so. Thus, equilibrium expressions applicable to a competitive antibody (fluorescence-labelled and unlabelled) assay for antigen on cell surfaces by flow cytometry were derived. Rearranging the equation for $K_{rel}$, we have the ratio of bound, unlabelled to bound, labelled ligand concentrations as $$[RL]/[RL^*]=(K^L/K^{L^*})([L]/[L^*]).$$

Now, the concentrations of unlabelled (labelled) ligand for experiments in which unlabelled and labelled ligand bind to antigenic receptors on cells are directly proportional to the loss (gain) of fluorescence intensity along the sigmoidal part of an intensity versus ligand concentration curve, so that $$[RL]/[RL^*]=(\Delta F_{max}-\Delta F)/(\Delta F-\Delta F_{min}),$$

in which $\Delta F_{max}$, $\Delta F_{min}$ define the plateau levels at high and low intensity, and $\Delta F$ defines the fluorescence intensity at any point along the curve. Thus, at the half-titration point, when $\Delta F=\Delta F_{min}+\frac{1}{2}(\Delta F_{max}-\Delta F_{min})$, so that $(\Delta F_{max}-\Delta F)/(\Delta F-\Delta F_{min})=1$, then $[RL]=[RL^*]$, i.e., the concentration of unlabelled ligand bound sites is equal to the concentration of labelled ligand bound sites. Also, it follows that $$(K^L/K^{L^*})([L]/[L^*])=1, \text{ and so}$$

$$K^L/K^{L^*}=[L^*]/[L].$$

Also, note that $K_{rel}=K^L/K^{L^*}=[L^*]/[L]$ at the half-titration point. Further, if the total ligand concentrations, L and L*, at the half-titration point are arranged experimentally so that the concentrations of bound ligand, [RL] and [RL*], are much smaller than the solution concentrations, [L] and [L*], then $[L]\sim L$ and $[L^*]\sim L^*$, and $K_{rel}=L^*/L$.

Conditions for useful competitive reactions can be stipulated as follows:
1. The components of the reaction should be chosen such that the relative equilibrium constant is of the order of unity;
2. If condition 1 cannot be met, the concentrations of ligands should be adjusted so that all species involved in the equilibrium are present in appreciable concentrations.

Furthermore, the exchange rate constants for the antibody-antigen reaction as estimated from association-dissociation rate constants, $k_d$ or $c_o k_a$[25] ranging from about $10^2$ to $10^{-4}$ sec$^{-1}$ are low, bordering on and overlapping with values for kinetically inert complexes, $10^{-3}$ to $10^{-6}$ sec$^{-1}$. For this range, the half-lives of association or dissociation reactions are greater than one minute. Rates for interaction of antibody with antigen on cell surfaces are expected to be even lower due to selectivity of monoclonal antibody for specific antigens only, and thus antibody-cell equilibration times range from about 10 to 60 minutes.

In a preferred method of the present invention the specific binding constant of a marker (a labelled ligand) was evaluated as follows:
(a) a plurality of titers of blood samples with a predetermined amount of marker material was incubated with a fixed volume of a suspension of formed bodies for a sufficient time (60–120 minutes) to produce a plurality of mixtures in which the marker concentration varies from mixture to mixture, over a sufficient range of marker concentration (below and above saturation point, preferably between about 100% saturation and less than about 10% saturation, saturation defined as the point wherein all targeted receptors are occupied by labelled ligand);
(b) the mixtures were analyzed with an instrument that measures light scatter and fluorescent emission of formed bodies such as a flow cytometer, to provide a first set of values, each value of said first set representing the mean channel intensity of the fluorescence or light scatter produced by material bound to the irradiated blood cells comprising an associated mixture;
(c) the set of values obtained from the mean channel intensities was used to calculate the specific binding constant by the following steps:
(i) obtain a set of values for the fraction of receptor sites on targeted formed bodies that are occupied by marker, by dividing each mean channel fluorescence intensity by the mean channel fluorescence intensity at saturation;
(ii) evaluate the saturation concentration of marker on formed bodies from a set of $\theta_2$ (fractional occupancy of surface receptor) values (range 0–1), obtained by dividing the mean channel at each titer by the maximum value (saturation). This sets $\theta_2=1$ at saturation. Saturation is obtained by running a series of increasing titers until the intensity no longer changes or reaches a maximum value—this is saturation;
(iii) a plot of $\theta_2/1-\theta_2$ versus the total concentration of fluorescent labelled ligand is drawn, and an estimate of the specific binding constant, K, is obtained from the slope of said plot;
(iv) with the estimate of the specific affinity constant, the solution concentration of fluorescent marker for each titer point is then calculated using the binding equation, $[\theta_2/(1-\theta_2)]$/association constant=solution concentration. The initial association constant is estimated from the slope of the plot in step (iii);
(v) having obtained the solution concentration, surface concentration of marker and saturation concentration for each titer point may be calculated;
(vi) the values obtained for saturation concentration for all titer trials are compared in order to minimize their difference i.e., make them as similar as possible for all trials, by adjustment of the binding or association constant value;
(vii) the final adjusted association constant value is the specific binding constant.

In a preferred method of the present invention the receptors on formed bodies contained in a whole blood sample, were enumerated as follows:
(a) a plurality of titers of blood samples with a predetermined amount of marker material was incubated with a fixed volume of a suspension of formed bodies for a sufficient time (60–120 minutes) to produce a plurality of mixtures in which the marker concentration varies from mixture to mixture, over a sufficient range of marker concentration (below and above saturation point, preferably between about 100% saturation and less than about 10% saturation, saturation defined as the point wherein all targeted receptors are occupied by labelled ligand);
(b) the marked formed bodies were analyzed with an instrument that measures light scatter and fluorescent emission of formed bodies preferably a flow cytometer, to obtain a first set of values, each value of said first set representing the mean channel intensity of the fluorescence or light scatter produced by marker material bound to the irradiated blood cells comprising an associated mixture;
(c) the set of values obtained for the mean channel intensities was used to calculate the average number of receptors per formed body by the following steps:
(i) obtain a set of values for the fraction of receptor sites on targeted formed bodies that are occupied by marker by dividing each mean channel fluorescence intensity by the mean channel fluorescence intensity at saturation;
(ii) evaluate the saturation concentration of marker on formed bodies from a set of $\theta_2$ (fractional occupancy of surface receptor) values (range 0–1), obtained by dividing the mean channel at each titer by the maximum value (saturation). This sets $\theta_2=1$ at saturation. Saturation is obtained by running a series of increasing titers until the intensity no longer changes or reaches a maximum—this is saturation;

(iii) a plot of $\theta_2/1-\theta_2$ versus the total concentration of fluorescent labelled ligand is drawn, and an estimate of the specific binding constant, K, is obtained from the slope of said plot;

(iv) with the estimate of the specific affinity constant, the solution concentration of fluorescent marker for each titer point is then calculated using the binding equation, $[\theta_2/(1-\theta_2)]$/association constant=solution concentration. The initial association constant is estimated from the slope of the plot in step (iii);

(v) having obtained the solution concentration, surface concentration of marker and saturation concentration for each titer point may be calculated;

(vi) the values obtained for saturation concentration for all titer trials are compared in order to minimize their difference i.e., make them as similar as possible for all trials, by adjustment of the binding or association constant value;

(vii) final adjusted association constant value is the specific binding constant;

(viii) the total concentration of receptors and the total number of receptors was then determined using the final optimized value of the saturation concentration of marker;

(ix) the total number of formed bodies in a sample of appropriately labelled ligand was obtained by running the sample on a hematology analyzer preferably the COULTER® STKS or S-Plus counter and, if required for subsets, on a flow cytometer;

(x) having obtained the total surface site concentration in a sample and having obtained the total number of formed bodies in a sample, the number of sites per formed body may then be calculated from the ratio of total number of receptors in (viii) to the total number of formed bodies.

Having obtained the specific binding constant of the labelled ligand, competitive binding experiments were used to obtain the specific binding constant of unlabelled ligand, which cannot be obtained directly using flow cytometry. The specific binding constant of unlabelled ligand is important, because in order for the labelled ligand to be useful, the specific binding constant of the labelled ligand should be very similar to that of the unlabelled ligand. Thus, obtaining the specific binding constant of unlabelled ligands provides a method of identifying useful markers (labelled ligands). Competitive binding experiments provide a method of obtaining the specific binding constant of the unlabelled ligands.

The competitive binding experiment also provides a means for analyzing for soluble antigen that is present in whole blood plasma in addition to analyzing antigen that is expressed on the cell surface. Soluble antigen in plasma is a result of shedding from the cell surface. The presence of soluble antigen is important because of its correlation with disease states or state of activation of cells.

Thus, provided that there is still antigen on the formed body, a competitive binding experiment is used to determine the amount of antigen that is in solution.

In a preferred method of the present invention the receptors released from the surface of formed bodies into the solution are determined by performing competitive binding experiments with samples of whole blood, as follows:

(a) incubating a plurality of samples of labelled ligand (marker) for a sufficient time (60 to 120 minutes) with a fixed volume of suspension of formed bodies, in which a suitable concentration of marker (i.e., concentration is not above but close to saturation) is maintained constant;

(b) adding and incubating unlabelled ligand for a sufficient time (60 to 120 minutes) with mixtures of step (a), in which the concentration of unlabelled ligand is varied over a sufficient range (i.e., where enough marker is displaced so as to obtain from 0 to 95–100% inhibition);

(c) analyzing the marked formed bodies in mixtures from step (b) with an instrument that measures light scatter and fluorescent emission of formed bodies preferably a flow cytometer to obtain the mean channel fluorescence intensities of marked formed bodies for each titer mixture of step (b);

(d) using the mean channel intensities to obtain the percent inhibition of labelled ligand binding to receptors on formed bodies by the presence of unlabelled ligand for each titer point;

(e) obtaining a probability-log graphical representation of said percent inhibition as the logit function against the concentration of unlabelled ligand for all titer points;

(f) identifying the concentration of unlabelled ligand in the bimodal curve of said graphical representation at which a discontinuity in the slope of the curves is observed;

(g) using the concentration of unlabelled ligand from step (f) to determine the concentration of receptors released from the surface of formed bodies into solution by using an appropriate ligand (antibody)-to-receptor (soluble antigen) binding ratio (1:2 for IgG antibody, 1:10 for IgM antibody) and a sample-to-blood volume factor.

In a preferred method of the present invention the receptors released from the surface of formed bodies into the solution are determined by performing competitive binding experiments with sample of whole blood, as follows:

(a) incubating a plurality of samples of labelled ligand (marker) for a sufficient time (60 to 120 minutes) with a fixed volume of suspension of formed bodies, in which a suitable concentration of marker (i.e., concentration is not above but close to saturation) is maintained constant;

(b) adding and incubating unlabelled ligand for a sufficient time (60 to 120 minutes) with mixtures of step (a), in which the concentration of unlabelled ligand is varied over a sufficient range (i.e., where enough marker is displaced so as to obtain from 0 to 95–100% inhibition);

(c) analyzing the marked formed bodies in mixtures from step (b) with an instrument that measures light scatter and fluorescent emission of formed bodies preferably a flow cytometer to obtain the mean channel fluorescence intensities of marked formed bodies for each titer mixture of step (b);

(d) identifying the concentration of unlabelled ligand at which the mean channel intensity in the competitive binding trials is equal to the mean channel intensity of a control which contained no unlabelled ligand but had the same concentration of labelled ligand and the same volume of a suspension of formed bodies;

(e) using the concentration of unlabelled ligand from step (d) to determine the concentration of receptors released from the surface of formed bodies into solution by using an appropriate ligand (antibody)-to-receptor (soluble antigen) binding ratio (1:2 for IgG antibody, 1:10 for IgM antibody) and a sample-to-blood volume factor.

In another preferred method of the present invention, the specific binding constant of unlabelled ligand for receptors on formed bodies in a whole blood sample, are determined as follows:

(a) incubating a plurality of titers of blood samples with a predetermined amount of marker material to produce a plurality of mixtures in which the marker concentration varies from mixture to mixture, over a sufficient range between about 100% saturation and less than about 10% saturation;

(b) analyzing the mixtures with an instrument that measures light scatter and fluorescent emission of formed bodies, to provide a first set of value, each value of said first set representing the mean channel intensity of the fluorescence or light scatter produced by material bound to the irradiated blood cells comprising an associated mixture;

(c) using the set of values obtained from the mean channel intensities to calculate the specific binding constant of labelled ligand (marker) by the following steps:

(i) obtain a set of values for the fraction of receptor sites on targeted formed bodies that are occupied by marker, by dividing each mean channel fluorescence intensity by the mean channel fluorescence intensity at saturation;

(ii) evaluate the saturation concentration of marker on formed bodies from a set of $\theta_2$ (fractional occupancy of surface receptor) values (range 0–1), obtained by dividing the mean channel at each titer by the maximum value (saturation). This sets $\theta_2=1$ at saturation. Saturation is obtained by running a series of increasing titers until the intensity no longer changes or reaches a maximum value— this is saturation;

(iii) a plot of $\theta_2/1-\theta_2$ versus the total concentration of fluorescent labelled ligand is drawn, and an estimate of the specific binding constant, K, is obtained from the slope of said plot;

(iv) with the estimate of the specific affinity constant, the solution concentration of fluorescent marker for each titer point is then calculated using the binding equation, $[\theta_2/(1-\theta_2)]$/association constant=solution concentration. The initial association constant is estimated from the slope of the plot in step (iii);

(v) having obtained the solution concentration, surface concentration of marker and saturation concentration for each titer point may be calculated;

(vi) the values obtained for saturation concentration for all titer trials are compared in order to minimize their difference i.e., make them as similar as possible for all trials, by adjustment of the binding or association constant value;

(vii) obtaining the specific binding constant of labelled ligand (marker) from the final adjusted association constant;

(d) incubating a plurality of samples of labelled ligand (marker) for a sufficient time (60 to 120 minutes) with a fixed volume of suspension of formed bodies, in which a suitable concentration of marker (i.e., concentration is not above but close to saturation) is maintained constant;

(e) adding and incubating unlabelled ligand for a sufficient time (60 to 120 minutes) with mixtures of step (d), in which the concentration of unlabelled ligand is varied over a sufficient range (i.e., where enough marker is displaced so as to obtain from 0 to 95–100% inhibition);

(f) analyzing the marked formed bodies in mixtures from step (e) with an instrument that measures light scatter and fluorescent emission of formed bodies preferably a flow cytometer to obtain the mean channel fluorescence intensities of marked formed bodies for each titer mixture of step (e);

(g) identifying the concentration of unlabelled ligand at which the mean channel intensity in the competitive binding trials of step (e) reaches the half-titration point;

(h) using said concentration of unlabelled ligand, the constant concentration of labelled ligand, and the specific binding constant determined for the labelled ligand to evaluate the specific binding constant of the unlabelled ligand by using the reciprocal relationship derived between specific binding constant and concentration of ligand at the half-titration point of competitive binding experiments.

The following examples further illustrate various features of the invention but are intended to in no way limit the scope of the invention for enumerating receptor molecules for specific binding partners on formed bodies and in solution.

EXAMPLE 1

Enumeration of Surface Sites for Dye Molecule on Silver Particle

The method of this Example uses a previous study [21]. The number of surface sites available to the dye molecule per silver particle was not calculated in the previous study [21] but (if the number of particles/cm$^3$ were accurately known), it could be estimated as follows:

Volume of sample in L×total surface site concentration in mol/L×$N_{Avogadro}$ (6.022×10$^{23}$/mol)/no. of particles in sample.

It is estimated as 0.010 L×1.1×10$^{-5}$M×6.022×10$^{23}$/mol// 1.5×10$^{13}$ particles=4.4×10$^3$ dye sites/particle. The number of silver particles per cm$^3$ was not directly measured but was estimated from the amount of silver used to prepare the colloid and from the size of the silver particles (~20 nm diameter). Similar results for citrate measured by a radioactive exchange method on the same silver particles of 13–15 nm diameter [26] gave an estimate of 2.1×10$^3$ citrate sites/particle.

EXAMPLE 2

Enumeration of Surface Sites for Fluorescent Markers on Formed Bodies

The method of Example 1 as outlined can be extended to specific, fluorescent marker instead of dye molecule as the ligand, and biological cell surfaces instead of a silver colloid surface. Various titers of fluorescent marker were mixed with a constant number of cells, equilibrated, the cells were fixed and quenched, and analyzed by flow cytometry. In these experiments, the background fluorescence intensity from marker in solution is much weaker than the fluorescence intensity from the high local concentration of marker on cells that are analyzed one at a time on the flow cytometer. Thus, separation of bound and unbound marker such as by washing of cells to remove unbound marker is unnecessary. The normalized fluorescent marker intensity was calculated from the ratio of mean channel positions of fluorescent marker at various total marker concentrations, $\Delta F$, to a maximum mean channel position for a marker concentration that gave saturation of receptor sites, $\Delta F_{max}$. This normalized intensity, $\Delta F/\Delta F_{max}$, is also the fraction, $\theta_2$, of receptor sites on the biological cell surface, occupied by the fluorescent marker. Assuming a 1:1 binding stoichiometry between fluorescent ligand and antigenic cell surface receptor, the final average value of $c_{sat}$ (obtained as described supra) was taken to be equivalent to the total receptor concentration in the sample. The number of receptors per cell was then calculated as (Volume of sample in L)×(total receptor concentration in mol/L)×($N_{Avogadro}$)/(number of targeted cells per 100 $\mu$L whole blood as determined on the COULTER S-Plus counter or STKS 2B analyzer, and the COULTER Profile II flow cytometer when needed to determine lymphocyte subset percentage).

Note that a single whole blood sample per fluorescent marker titer is required in this method. No fractional occupancy versus concentration of cells dependence [27] is needed.

EXAMPLE 3

Equilibrium Binding Characteristics and Enumeration of CD4 and CD8 Antigenic Sites on Lymphocytes As a reference for a high affinity antibody-cell surface antigen interaction for which data on receptors/cell, $3\times10^4$ [28], $7.53\times10^4$ [29], and $6.5\times10^4$ [30] have been established, CD4 antigen receptors per CD4 lymphocyte in whole blood were first enumerated to test the outlined methods. Also, preserved CD4 control cells [31], treated with 10 ng/mL phorbol myristate acetate (PMA) for 24 hours to induce the activated CD4 lymphocytes to partially release their antigenic receptors and then washed, were analyzed in the same way to investigate the sensitivity of this receptor enumeration method to small changes in the number of receptors/cell. Fluorescence labelling of the cells was done with titers of the dual marker, T4-PE/T8-FITC (T4 clone SFCI12T4D11 and T8 clone SFCI21Thy2D3), and 100 $\mu$L of sample (whole blood or reconstituted control cells) in capped 12×75 mm glass tubes. The standard 10 $\mu$L titer of dual marker contained 0.28 $\mu$g T4-PE and 0.14 $\mu$g T8-FITC.

The COULTER Profile II flow cytometer was used in all runs. COULTER DNA-Check and Standard-Brite beads are run prior to measuring controls and samples for alignment of laser source to set CVs at +/−2% and to standardize the mean channel fluorescence intensities within 0.5 channels. Then, the isotypic control, consisting of MsIgG1-PE/MsIgG1-FITC, is used to determine intensities of background auto- and non-specific fluorescence. Quadstats are usually set in first decade of dual color histogram (Fl1 versus Fl2) so that quadrant 3, closest to the origin, contains between 98.0 and 100% of fluorescent events, and fluorescence intensities of samples below Quad-stat or discriminator lines can be discounted. Further, the color compensation control, T4-PE (Fl2)/T8-FITC(Fl1) is used to correct for overlap between fluorescence emission spectra of FITC and PE chromophores. CD4+ and CD8+ cells as well as CD3+ cells (in subsequent section) were analyzed by gating on the lymphocyte population in the histogram while CD16B+ and CD15+ cells (in subsequent sections) were analyzed by gating on the granulocyte population.

The raw fluorescence data are compiled in Table I. The total sample volume was made constant for all titers in each run by addition of 1xPBS buffer. Mixtures of control cells or EDTA-stabilized whole blood and markers were incubated at room temperature for 10 min on a Corning Model 4010 multi-tube vortexer and then Q-PREPed for 35 sec to lyse red blood cells and fix the white blood cells. The Q-PREP added about 1 mL to the total volume of sample and was assumed not to disturb the equilibrated amount of marker on the cells.

TABLE I

Dual Marker, T4-PE/T8-FITC, titers with whole blood and preserved lymphocytes: run with 3 donors and run with 2 vials of preserved cells; values in parentheses are standard deviations (SD), no SD was given to values near or below the discriminator line.

| $\mu$L of dual marker | donor 1 | donor 2 | donor 3 | vial 1 | vial 2 |
|---|---|---|---|---|---|
| mean channel T4-PE fluorescence intensity | | | | | |
| .010 | 0.18 | 0.13 | 0.23 | — | 1.200 |
| .025 | 0.40 | 0.21 | 0.90 | – | 1.383 |
| .050 | 1.737 | 1.340 | 2.990 | 1.194 | 1.683 |
| | | | (0.817) | | |
| .075 | 2.550 | 1.527 | 3.777 | 1.413 | 2.141 |
| | (0.597) | | (1.012) | | |
| .100 | 3.559 | 2.279 | 4.567 | 1.567 | 2.128 |
| | (0.883) | (0.521) | (1.180) | | |
| .250 | 6.542 | 5.280 | 8.250 | 2.052 | 2.390 |
| | (1.785) | (1.226) | (2.167) | | |
| .500 | 9.899 | 9.007 | 10.63 | 2.173 | 2.474 |
| | (3.110) | (2.157) | (3.05) | | |
| .750 | 11.33 | 10.57 | 11.28 | 2.297 | 2.460 |
| | (3.65) | (2.97) | (3.19) | | |
| 1.00 | 11.88 | 11.35 | 11.45 | 2.338 | 2.364 |
| | (3.63) | (2.99) | (3.13) | | |
| 5.00 | 13.26 | 12.97 | 12.25 | 2.009 | 1.984 |
| | (4.41) | (3.96) | (3.51) | | |
| 10.0 | 13.48 | 13.35 | 12.48 | 2.014 | 2.005 |
| | (4.29) | (4.09) | (3.79) | | |
| 20.0 | 13.39 | 13.17 | 13.11 | | |
| | (5.30) | (5.36) | (3.76) | | |
| mean channel TB-FITC fluorescence intensity | | | | | |
| .250 | | | 1.463 | | |
| .500 | 1.835 | 1.639 | 2.569 | | |
| | | | (0.657) | | |
| .750 | 2.506 | 2.328 | 3.872 | | |
| | (0.595) | (0.612) | (1.125) | | |
| 1.00 | 2.921 | 3.099 | 4.856 | | |
| | (0.782) | (1.006) | (1.656) | | |
| 5.00 | 8.323 | 8.167 | 10.61 | | |
| | (3.989) | (5.707) | (5.38) | | |
| 10.0 | 10.77 | 10.03 | 12.24 | | |
| | (5.98) | (7.74) | (7.00) | | |
| 20.0 | 11.08 | 10.27 | 13.01 | | |
| | (6.08) | (8.20) | (7.20) | | |

The fluorescence intensity versus total marker concentration data showed the characteristics of Langmuir-type binding [32, 33] of marker to receptor sites on cell surfaces. A steep, linear rise at low concentration was followed by a smooth curvature away from the intensity axis and then a plateau at high concentration to give a hyperbolic curve. Also, characteristic of fluorescent emitters on surfaces, some concentration quenching of intensity was noted at or near saturation as the average distance between emitters became small. Thus, only titer points well below saturation could be reliably processed for further analyses. Further, low concentration titer points generally showed more deviation due to errors in dilution of the marker concentrates.

The raw data consisting of cell fluorescent marker intensities on CD4+ or CD8+ lymphocytes and total marker concentrations before Q-PREPing were then used to obtain the results in Tables II and III. Estimates of K values for T4-PE binding were first made as $6.8\times10^9$, $4.7\times10^9$, and $1.2\times10^{10}$; $4.3\times10^{10}$, and $1.8\times10^{11} M^{-1}$ for donors 1, 2, 3 and vials 1 and 2, respectively, from the slopes of $\theta_2/(1-\theta_2)$ versus $c_{tot}$ plots at low concentrations between 0.010 and 0.250 $\mu$L titers of dual marker. The slopes of the corresponding log-log plots near the 50% site occupation point between $\theta_2$=0.20 and 0.80 gave Hill constants of 1.3, 1.4, 1.1, 1.1, and 0.84, respectively, close to the non-cooperative interaction value of 1.0. The maximum value for the Hill constant in a cooperative binding case would be the number of receptor sites per cell.

TABLE II

T4-PE Binding Data Analysis

| $\mu$L | $\theta_2$ | $\theta_2/1-\theta_2$ | $c_{tot}$, M × 10$^{10}$ | $c_{soln}$, M × 10$^{10}$ | $c_{surf}$, M × 10$^{10}$ | $c_{sat}$, M × 10$^{10}$ |
|---|---|---|---|---|---|---|
| \multicolumn{7}{c}{Donor 1, K = 9.0 × 10$^9$ M$^{-1}$} |
| .010 | .013 | .013 | .058 | .014 | .044 | 3.35 |
| .025 | .030 | .031 | .146 | .034 | .112 | 3.72 |
| .050 | .129 | .148 | .292 | .164 | .128 | 0.99 |
| .075 | .189 | .233 | .438 | .259 | .179 | 0.95 |
| .100 | .264 | .359 | .583 | .399 | .184 | 0.70 |
| .250 | .485 | .942 | 1.458 | 1.047 | .411 | 0.85 |
| .500 | .734 | 2.759 | 2.917 | — | — | — |
| .750 | .841 | 5.289 | 4.375 | — | — | — |
| 1.00 | .881 | 7.403 | 5.833 | — | — | — |
| 5.00 | .984 | 61.5 | 29.167 | — | — | — |
| 10.0 | 1.00 | — | — | — | — | — |
| \multicolumn{7}{c}{Donor 2, K = 7.0 × 10$^9$ M$^{-1}$} |
| .010 | .0097 | .0098 | .058 | .014 | .044 | 4.54 |
| .025 | .016 | .016 | .146 | .023 | .123 | 7.69 |
| .050 | .100 | .111 | .292 | .159 | .134 | 1.34 |
| .075 | .114 | .129 | .438 | .184 | .254 | 2.23 |
| .100 | .171 | .206 | .583 | .294 | .289 | 1.69 |
| .250 | .396 | .656 | 1.458 | .937 | .521 | 1.31 |
| .500 | .675 | 2.077 | 2.917 | — | — | — |
| .750 | .792 | 3.808 | 4.375 | — | — | — |
| 1.00 | .850 | 5.667 | 5.833 | — | — | — |
| 5.00 | .972 | 34.71 | 29.167 | — | — | — |
| 10.0 | 1.00 | — | — | — | — | — |
| \multicolumn{7}{c}{Donor 3, K = 1.65 × 10$^{10}$ M$^{-1}$} |
| .010 | .017 | .018 | .058 | .011 | .047 | 2.69 |
| .025 | .069 | .074 | .146 | .045 | .101 | 1.47 |
| .050 | .228 | .295 | .292 | .179 | .113 | .496 |
| .075 | .288 | .404 | .438 | .245 | .193 | .670 |
| .100 | .348 | .534 | .583 | .324 | .259 | .744 |
| .250 | .629 | 1.695 | 1.458 | 1.027 | .431 | .685 |
| .500 | .811 | 4.291 | 2.917 | 2.601 | .316 | .390 |
| .750 | .860 | 6.143 | 4.375 | 3.723 | .652 | .758 |
| 1.00 | .873 | 6.874 | 5.833 | 4.166 | 1.667 | 1.91 |
| 5.00 | .934 | 14.15 | 29.167 | 8.576 | 20.591 | 22 |
| 10.0 | .952 | 19.83 | 58.333 | 12.018 | 46.315 | 49 |
| 20.0 | 1.00 | — | — | — | — | — |
| \multicolumn{7}{c}{Vial 1, K = 5.0 × 10$^{10}$ M$^{-1}$} |
| .010 | — | — | — | — | — | — |
| .025 | — | — | — | — | — | — |
| .050 | .511 | 1.045 | .318 | .209 | .109 | .213 |
| .075 | .604 | 1.525 | .477 | .305 | .172 | .285 |
| .100 | .670 | 2.030 | .636 | .406 | .230 | .343 |
| .250 | .878 | 7.197 | 1.59 | 1.439 | .151 | .172 |
| .500 | .929 | 13.085 | 3.18 | 2.617 | .563 | .606 |
| .750 | .982 | 54.555 | 4.77 | 10.911 | — | — |
| 1.00 | 1.00 | — | — | — | — | — |
| \multicolumn{7}{c}{Vial 2, K = 2.0 × 10$^{11}$ M$^{-1}$} |
| .010 | .485 | .942 | .0636 | .047 | .017 | .035 |
| .025 | .559 | 1.268 | .159 | .063 | .096 | .172 |
| .050 | .680 | 2.125 | .318 | .106 | .212 | .312 |
| .075 | .865 | 6.407 | .477 | .320 | .157 | .182 |
| .100 | .860 | 6.143 | .636 | .307 | .329 | .383 |
| .250 | .966 | 28.412 | 1.59 | 1.421 | .169 | .175 |
| .500 | 1.00 | — | — | — | — | — |

TABLE III

T8-FITC Binding Data Analysis

| $\mu$L | $\theta_2$ | $\theta_2/(1-\theta_2)$ | $c_{tot}$, M × 10$^{10}$ | $c_{soln}$, M × 10$^{10}$ | $c_{surf}$, M × 10$^{10}$ | $c_{sat}$, M × 10$^{10}$ |
|---|---|---|---|---|---|---|
| \multicolumn{7}{c}{Donor 1, K = 7.0 × 10$^8$ M$^{-1}$} |
| .500 | .1656 | .1985 | 3.646 | 2.836 | 0.810 | 4.9 |
| .750 | .2262 | .2923 | 5.469 | 4.176 | 1.293 | 5.7 |
| 1.00 | .2636 | .3579 | 9.722 | 5.113 | 4.609 | 17. |
| 5.00 | 3.019 | 48.61 | 43.13 | 5.483 | 7.3 |  |
| 10.0 | .9720 | 34.71 | 97.22 | 495.8 | — | — |
| 20.0 | 1.000 | — | — | — | — | — |
| \multicolumn{7}{c}{Donor 2, K = 1.0 × 10$^9$ M$^{-1}$} |
| .500 | .1596 | .1899 | 3.646 | 1.899 | 1.747 | 10.9 |
| .750 | .2267 | .2931 | 5.469 | 2.931 | 2.538 | 11.2 |
| 1.00 | .3017 | .4320 | 9.722 | 4.320 | 5.402 | 17.9 |
| 5.00 | .7952 | 3.883 | 48.61 | 38.83 | 9.781 | 12.3 |
| 10.0 | .9766 | 41.73 | 97.22 | 417.3 | — | — |
| 20.0 | 1.000 | — | — | — | — | — |
| \multicolumn{7}{c}{Donor 3, K = 1.0 × 10$^9$ M$^{-1}$} |
| .250 | .1124 | .1266 | 1.823 | 1.266 | 0.557 | 4.9 |
| .500 | .1975 | .2461 | 3.646 | 2.461 | 1.185 | 6.0 |
| .750 | .2976 | .4237 | 5.469 | 4.237 | 1.232 | 4.1 |
| 1.00 | .3732 | .5954 | 9.722 | 5.954 | 3.768 | 10.1 |
| 5.00 | .8155 | 4.420 | 48.61 | 44.20 | 4.411 | 5.4 |
| 10.0 | .9408 | 15.89 | 97.22 | 158.9 | — | — |
| 20.0 | 1.000 | — | — | — | — | — |

Estimates of K values for T8-FITC binding were 6.4×10$^8$, 8.4×10$^8$, and 9.3×10$^8$ M$^{-1}$ for donors 1, 2, and 3, respectively, from the slope of $\theta_2/(1-\theta_2)$ versus $c_{tot}$ plots at low titers between 0.250 and 5.00 $\mu$L of dual marker. The corresponding log-log plots gave Hill constants of 1.0, 0.83, and 1.1, respectively. The high association constants (~10$^{10}$M$^{-1}$), calculated for T4-PE binding to CD4antigen on lymphocytes, served to produce the most consistent set of $c_{sat}$ values. Each titer point can be considered as a separate determination of $c_{sat}$. Values of $c_{sat}$, averaged for titers in the middle of the range between 0.050 and 1.00 or 5.00 $\mu$L, for each run were then used to calculate the number of receptors per cell listed in Table IV, when samples were analyzed on the COULTER S-Plus counter for lymphocytes (L) and then on the COULTER Profile II flow cytometer for percentage CD4+ and CD8+ cells in the lymphocyte population.

TABLE IV

Total CD4 and CD8 Receptor Concentrations in Samples and No. Receptors/Cell. Estimated standard deviations are given in parentheses.

|  | L/100 $\mu$L | % CD4 in L | % CD8 in L |
|---|---|---|---|
| Donor 1 | 2.3 × 10$^5$ | 43.1 | 24.3 |
| Donor 2 | 1.7 × 10$^5$ | 45.1 | 23.0 |
| Donor 3 | 2.2 × 10$^5$ | 41.4 | 33.7 |
| Vial 1 | 1.1 × 10$^5$ | 38.5 | — |
| Vial 2 | 1.1 × 10$^5$ | 39.1 | — |

| Sample | $c_{sat}$ M × 10$^{10}$ | Sample Vol., L × 10$^4$ | Total No. Receptors | No. CD4 Cells | Receptors /Cell |
|---|---|---|---|---|---|
| Donor 1 | 0.87(.13) | 1.20 | 6.29 × 10$^9$ | 9.9 × 10$^4$ | 6.3(0.9) × 10$^4$ |
| Donor 2 | 1.64(.43) | 1.20 | 1.18 × 10$^{10}$ | 7.7 × 10$^4$ | 1.5(0.4) × 10$^5$ |
| Donor 3 | 0.62(.15) | 1.20 | 4.48 × 10$^9$ | 9.1 × 10$^4$ | 4.9(1.2) × 10$^4$ |
| Vial 1 | 0.25(.08) | 1.10 | 1.68 × 10$^9$ | 4.2 × 10$^4$ | 3.9(1.2) × 10$^4$ |
| Vial 2 | 0.24(.10) | 1.10 | 1.62 × 10$^9$ | 4.3 × 10$^4$ | 3.8(1.5) × 10$^4$ |

TABLE IV-continued

Total CD4 and CD8 Receptor Concentrations in Samples and No. Receptors/Cell. Estimated standard deviations are given in parentheses.

| | | | No. CDB Cells | | |
|---|---|---|---|---|---|
| Donor 1 | 6.0(1.2) | 1.20 | $4.3 \times 10^{10}$ | $5.6 \times 10^4$ | $7.7(1.5) \times 10^5$ |
| Donor 2 | 11.(1.) | 1.20 | $8.3 \times 10^{10}$ | $3.9 \times 10^4$ | $2.1(0.2) \times 10^6$ |
| Donor 3 | 5.1(.8) | 1.20 | $3.7 \times 10^{10}$ | $7.4 \times 10^4$ | $5.0(0.8) \times 10^5$ |

Previous measurements [30] of the number of bound OKT8 antibody-FITC molecules per T8+ cell in a preparation of human peripheral blood mononuclear cells by flow cytometry gave receptor/cell values of $2.29 \times 10^5$ at 12° C. and $2.99 \times 10^5$ at 36° C.

EXAMPLE 4

Equilibrium Binding Characteristics and Enumeration of 1D3 and 3G8 Antigenic Sites on Neutrophils 1D3 (anti-CD16b or anti-FcγRIIIB), an IgM monoclonal antibody specific to neutrophils [34], was used. The 1D3 clone [A.T.C.C. Deposit No. HB 9445] was derived from fusion of Balb C mouse spleen cells immunized with purified human granulocytes and NS-1 plasmacytoma mouse myeloma cells. Purification of the 1D3 monoclonal antibody from concentrated cell culture supernatant was accomplished by 40% aqueous ammonium sulfate precipitation of proteins followed by Sephacryl S-300 HR (Pharmacia Biotech, Piscataway, N.J.) gel filtration chromatography. Prior to the precipitation step the conditioned media were filtered through a 0.2 μm filter. Following precipitation of proteins, the suspension was centrifuged at 1800×g for 20 minutes at 25° C. The supernatant was discarded and the residue was resuspended with 1×PBS, 0.1% sodium azide buffer solution, pH 7.2–7.3, to a total volume which did not exceed 2% of the S300 HR column volume. The pre-column sample was then centrifuged at 1800×g for 20 minutes at 25° C. The residue was discarded and the supernatant was loaded onto the S-300 HR column at a rate 10 times the cross-sectional area per hour (column equilibrated with 1×PBS, 0.1% sodium azide buffer, pH 7.2–7.3). The eluant from the column was monitored at 280 nm and the first detectable peak contained the 1D3 monoclonal antibody. The eluted peak fraction was then concentrated using a stirred cell fitted with a YM100 membrane (Amicon, Beverly, Mass.). Recovery of 1D3 monoclonal antibody, as determined by a rate nephelometry protein assay, was approximately 80%.

The 1D3 monoclonal antibody was further characterized by conjugating it to magnetic latex beads coated with aminodextran as previously disclosed [35]. Then, the mobility of the 1D3-conjugated beads was measured on the COULTER DELSA (Doppler Electrophoretic Light Scatter Analyzer) instrument as a function of pH. This provided an estimate of the pI of 1D3 monoclonal antibody, which cannot be obtained for IgM antibodies by conventional electrophoresis. All samples were prepared by adding 0.250 mL of 2.5% w/v beads to 500 mL of 0.01M aqueous potassium nitrate solution and adjusting pH with either 1M aqueous nitric acid or 1M potassium hydroxide solution. The results of mobility (μm-cm/V-s) versus pH measurements for aminodextran-coated polystyrene-magnetite latex beads, 1D3-conjugated beads, and KC16-conjugated beads are displayed in FIG. 1. KC16, a monoclonal antibody specific to red blood cells [36] (A.T.C.C. Deposit No. CRL 8994) is an IgG with a pI range of 7.8–8.35 as determined by electrophoresis. The pH at the point of zero charge (p.z.c.) was 7.2, 5.35, and 8.35, respectively, for the above beads. Since the p.z.c. of KC16-beads fell in the pI range of KC16 antibody alone, the p.z.c. of 1D3 beads, 5.35, may provide a good estimate of the actual pI of 1D3 antibody alone. A similar result (p.z.c.=5.85) was obtained with KC48-conjugated beads.

Conjugation of 1D3 monoclonal antibody to fluorescein-5-isothiocyanate (FITC Isomer I, Sigma Chemical Co., St. Louis, Mo.) was performed by addition of a calculated amount of a FITC stock solution to a fixed amount of antibody solution under continuous stirring and constant 25° C. temperature. The calculated amount of FITC stock solution was determined by performing 1 mg antibody conjugations at various excess molar ratios of FITC, spectrophotometrically determining the FITC:1D3 molar ratio (F/P) of the formed conjugates, generating an X-Y plot of excess molar ratio versus F/P, and computing the excess molar ratio required to obtain a conjugate with an F/P=25. The final concentration of 1D3 antibody in the reaction was 10 mg/mL. The 1D3 antibody concentrate was supplied in 1×PBS, 0.1% sodium azide solution. The stock solution of FITC was prepared by dissolving a calculated amount of FITC isomer I in 1.0M borate buffer, pH 9.8, solution at a concentration of 10 mg/mL. To minimize hydrolysis of FITC, the solution was used within one hour. The ligands were incubated for one hour, at which time the unbound FITC was separated from 1D3-FITC conjugate by Sephadex G-50 (Pharmacia Biotech) gel filtration chromatography (column equilibrated with 1×PBS, 0.1% sodium azide buffer). The first yellow-green band which eluted from the G-50 column contained the 1D3-FITC conjugate. Recovery of 1D3 in the FITC conjugate was 90%, as determined by a Lowry protein assay and the value of F/P=23.53 was determined spectrophotometrically.

Conjugation of the 1D3 monoclonal antibody to phycoerythrin (PE) was accomplished by first individually activating amino groups on the 1D3 antibody with the heterobifunctional cross-linker, sulfo-SMCC, sulfosuccinimidyl 4-(N-maleimidomethyl)cyclohexane-1-carboxylate (Pierce Chemical Co., Rockford, Ill.), to introduce reactive maleimide groups and activating amino groups on PE with Traut's reagent, IT, 2-iminothiolane hydrochloride (Pierce), to introduce reactive sulfhydryl groups in addition to intrinsic ones of cysteinyl residues in PE. The activation reactions were performed at a pH of 7.4 and at an approximate molar excess of activating reagent of 15. After incubation of the ligands in each activation for one hour at 25° C. using continuous stirring, the individual activated species were separated from other unreacted species on Sephadex G-50 (Pharmacia Biotech) gel filtration columns equilibrated with 5 mM Tris, 100 mM sodium chloride, pH 5.5. The activated species, sulfo-SMCC-1D3 and IT-PE, were then combined at a 1:1 molar ratio and allowed to react at 25° for one hour with continuous stirring. At the end of the conjugation reaction period, the 1D3-PE conjugate was separated from unreacted 1D3 and PE by gel filtration chromatography using a column packed with Sephacryl S-300 HR (Pharmacia Biotech) media and equilibrated with 100 mM phosphate buffer, 100 mM sodium chloride, 0.1 mM EDTA, ph 6.8. The first colored band to elute from the S-300 HR column contained the 1D3-PE conjugate. The conjugate was then diafiltered into 1×PBS, 0.1% sodium azide buffer solution, pH 7.2–7.3, with stabilizers. Concentration and recovery were determined spectrophotometrically. The recovery of 1D3 in the 1D3-PE conjugate was about 40%.

1D3-FITC was then used with the general white blood cell marker, KC56(anti-CD45)-PE, as a dual marker of cells in whole blood for analysis by flow cytometry.

Various aspects of neutrophil function have recently been reviewed [37, 38]. The Fcγ receptor III on neutrophil surfaces has some unusual characteristics. Soluble FcγRIII in normal human serum was detected in variable concentrations ranging from 7.3 to 75.9 nmol/L [39] with the monoclonal antibodies, CLBFcRgran 1, BW209/2 and 3G8 or 3G8 Fab. 3G8 is an anti-CD16b, IgG1 monoclonal antibody (clone derived from the hybridization of P3U1 mouse myeloma cells with splenocytes from a CD2F1 mouse immunized with human granulocytes). The 3G8 receptor is expressed on neutrophils, most (90%) natural killer cells, macrophages, and a subpopulation (10%) of peripheral blood monocytes. It cannot be detected on peripheral blood B and T cells of most individuals. Certain stimuli such as the chemotactic peptide, N-Formyl-MET-LEU-PHE, and phorbol myristate acetate (PMA), induce shedding of FcγRIII from the neutrophil surface [40, 41].

We found that neutrophils in normal blood donors have a highly variable expression of 1D3, FcγRIIIB antigen, on their surface at all times of the year. This was observed by flow cytometry of whole blood mixtures with various titers of the dual marker, 1D3-FITC/KC56-PE (4 μg 1D3-FITC/5 μg KC56-PE per 10 μL), followed by Q-PREP (lyse and quench) of the mixtures. Sufficiently high titers were used to obtain constant high mean channel intensities, indicating saturation of receptor sites, or to observe a decrease in mean channel intensity, showing concentration quenching of fluorescence intensity due to proximity of antigenic sites on the cell surface, possibly induced by crosslinking with the 1D3 antibody. A sigmoidal binding curve is often an indication of cooperative binding. Small changes might occur in fluorescence intensity at low marker concentrations due to weak binding to the antigen on the cell surface. The initial curve becomes more concave towards the intensity axis as more marker occupies antigenic sites, since molecules of IgM marker have attraction for one another on the surface of the cells. This attraction can also lead to aggregation of the IgM antibody on the cell surface with concomitant non-specific binding and higher than expected numbers of receptors per cell. Data for 1D3-FITC and 1D3-PE on neutrophils in whole blood do not show cooperative binding interactions. Also, Hill plots of $\log [\theta_2/(1-\theta_2)]$ versus $\log [c_{total}]$ gave slopes of 1.0+/−0.3 near $\theta_2=0.5$, indicative of non-cooperative binding.

We checked that the mean channel intensities of marker on neutrophils in Q-PREPed samples varies only up to one half a mean channel when samples are run within 2–3 hours on the flow cytometer. The outlined method of analysis was used to enumerate the mean receptor/neutrophil ratio. In run 1 with five normal donors as compiled in Table V, titers of dual marker were mixed with 100 μL of whole blood and incubated for 10 min, Q-PREPed, and the following raw, 1D3-FITC marker intensities on neutrophils were measured by flow cytometry.

TABLE V

Dual marker, 1D3-FITC/KC56-PE, titers with 100 μL of whole blood; run 1 with 5 donors; values in parentheses are standard deviations

| | mean channel 1D3-FITC fluorescence intensity | | | | |
|---|---|---|---|---|---|
| μL of dual marker | donor 1 | donor 2 | donor 3 | donor 4 | donor 5 |
| 1.25 | 5.387 | 2.837 | 5.312 | 3.775 | 4.680 |
| | (1.951) | (1.095) | (2.425) | (1.981) | (1.912) |
| 2.5 | 7.173 | 3.894 | 9.906 | 5.626 | 8.736 |
| | (2.496) | (1.879) | (4.122) | (3.052) | (3.370) |
| 5 | 10.53 | 4.588 | 12.89 | 8.238 | 11.86 |
| | (3.55) | (2.157) | (4.96) | (4.457) | (4.21) |
| 10 | 12.51 | 5.058 | 15.42 | 10.86 | 13.88 |
| | (4.19) | (2.236) | (5.73) | (5.58) | (4.90) |
| 15 | 13.96 | 5.336 | 16.70 | 11.91 | 14.80 |
| | (5.06) | (2.475) | (6.85) | (6.14) | (5.09) |
| 20 | 14.67 | 5.381 | 17.66 | 13.61 | 15.86 |
| | (5.70) | (2.423) | (7.69) | (7.36) | (5.84) |
| 25 | 14.77 | 5.490 | 15.43 | 14.19 | 16.26 |
| | (5.87) | (2.574) | (8.72) | (7.79) | (6.66) |
| 35 | 15.25 | 5.562 | 15.02 | 14.89 | 16.50 |
| | (8.35) | (2.712) | (10.20) | (9.62) | (7.66) |
| 50 | 14.77 | 5.424 | 14.08 | 14.85 | 16.57 |
| | (10.36) | (2.799) | (11.37) | (10.46) | (8.69) |

The data for each donor were used to estimate an initial K value from the slope of plots of $\theta_2/(1-\theta_2)$ versus $c_{tot}$ and a Hill constant, n, from the slope of the corresponding log-log plot. The results are shown as follows.

| donor | Estimated $K(M^{-1}) \times 10^8$ | n |
|---|---|---|
| 1 | 1.5 | 0.83 |
| 2 | 3.3 | 1.06 |
| 3 | 1.9 | 1.30 |
| 4 | 0.89 | 1.04 |
| 5 | 1.7 | 1.09 |

The results of analyses of the intensity data are shown in Table VI.

TABLE VI

Binding Data Analysis: run 1

| μL | $\theta_2$ | $\theta_2/1 - \theta_2$ | $c_{tot}$, $M \times 10^8$ | $c_{soln}$, $M \times 10^8$ | $c_{surf}$, $M \times 10^8$ | $c_{sat}$, $M \times 10^8$ |
|---|---|---|---|---|---|---|
| Donor 1, K = 1.6 × 10$^8$ M$^{-1}$ | | | | | | |
| 1.25 | .3532 | .5461 | .3865 | .3413 | .0291 | .082 |
| 2.5 | .4704 | .8882 | .7729 | .5551 | .2178 | .46 |
| 5 | .6905 | 2.231 | 1.546 | 1.394 | .0866 | .13 |
| 10 | .8203 | 4.565 | 3.092 | 2.853 | .1099 | .13 |
| 15 | .9154 | 10.82 | 4.638 | — | — | — |
| 20 | .9620 | 25.32 | 6.183 | — | — | — |
| 25 | .9685 | 30.75 | 7.729 | — | — | — |
| Donor 2, K = 3.4 × 10$^8$ M$^{-1}$ | | | | | | |
| 1.25 | .5101 | 1.041 | .3865 | .3062 | .0803 | .16 |
| 2.5 | .7001 | 2.334 | .7729 | .6865 | .0864 | .12 |
| 5 | .8249 | 4.711 | 1.546 | 1.385 | .161 | .19 |
| 10 | .9094 | 10.04 | 3.092 | 2.953 | .139 | .15 |

TABLE VI-continued

Binding Data Analysis: run 1

| $\mu L$ | $\theta_2$ | $\theta_2/(1-\theta_2)$ | $c_{tot}$, M × 10⁸ | $c_{soln}$, M × 10⁸ | $c_{surf}$, M × 10⁸ | $c_{sat}$, M × 10⁸ |
|---|---|---|---|---|---|---|
| 15 | .9594 | 23.63 | 4.638 | 6.950 | — | — |
| 20 | .9675 | 29.77 | 6.183 | 8.756 | — | — |
| 25 | .9871 | 76.52 | 7.729 | 22.50 | — | — |
| Donor 3, K = 2.2 × 10⁸ M⁻¹ | | | | | | |
| 1.25 | .3008 | .4302 | .3865 | .1955 | .1749 | .58 |
| 2.5 | .5609 | 1.277 | .7729 | .5804 | .1603 | .28 |
| 5 | .7299 | 2.702 | 1.546 | 1.228 | .253 | .35 |
| 10 | .8732 | 6.886 | 3.092 | — | — | — |
| 15 | .9456 | 17.38 | 4.638 | — | — | — |
| Donor 4, K = 1.0 × 10⁸ M⁻¹ | | | | | | |
| 1.25 | .2535 | .3396 | .3865 | .3396 | .0308 | .12 |
| 2.5 | .3778 | .6072 | .7729 | .6072 | .1335 | .35 |
| 5 | .5533 | 1.239 | 1.546 | 1.239 | .242 | .44 |
| 10 | .7293 | 2.694 | 3.092 | 2.694 | .269 | .37 |
| 15 | .7999 | 3.998 | 4.638 | 3.998 | .446 | .56 |
| 20 | .9140 | 10.63 | 6.183 | — | — | — |
| 25 | .9530 | 20.28 | 7.729 | — | — | — |
| Donor 5, K = 2.0 × 10⁸ M⁻¹ | | | | | | |
| 1.25 | .2824 | .3935 | .3865 | .1967 | .1736 | .61 |
| 2.5 | .5272 | 1.115 | .7729 | .5575 | .1832 | .35 |
| 5 | .7158 | 2.519 | 1.546 | 1.259 | .2215 | .31 |
| 10 | .8377 | 5.161 | 3.092 | 2.580 | .3825 | .46 |
| 15 | .8932 | 8.363 | 4.638 | 4.181 | .2625 | .29 |
| 20 | .9572 | 22.36 | 6.183 | — | — | — |
| 25 | .9813 | 52.47 | 7.729 | — | — | — |
| 35 | .9958 | 237.1 | 10.82 | — | — | — |

The total number of wbcs per 100 $\mu L$ of whole blood was determined on the COULTER S-Plus counter and the percentage of neutrophils in the wbc population was obtained by flow cytometry as the ratio of 1D3-FITC fluorescence intensity, bitmapped in the granulocyte region of the light scatter (FS versus SS) histogram, to the KC56-PE fluorescence intensity bitmapped over the entire granulocyte, monocyte, and lymphocyte regions.

Then, the average value of $c_{sat}$ was calculated from results in Table VI to give the number of 1D3 receptors per neutrophil as listed in Table VII.

TABLE VII

Total 1D3 Receptor Concentrations in Samples and No. Receptors/Cell, run 1

| donor | wbc/100 $\mu L$ | % N in wbc | N/100 $\mu L$ |
|---|---|---|---|
| 1 | 5.5 × 10⁵ | 43.0 | 2.36 × 10⁵ |
| 2 | 5.9 | 36.8 | 2.17 |
| 3 | 5.1 | 53.0 | 2.70 |
| 4 | 5.9 | 50.0 | 2.95 |
| 5 | 5.2 | 56.6 | 2.94 |

| Sample | $c_{sat}$, M × 10⁹ | Sample Vol, L | Total No. Receptors | No. Neutrophils | Receptors/Neutrophil |
|---|---|---|---|---|---|
| Donor 1 | 1.1(0.3) | 1.50 × 10⁻⁴ | 9.94 × 10¹⁰ | 2.36 × 10⁵ | 4.2(1.1) × 10⁵ |
| Donor 2 | 1.5(0.3) | 1.50 × 10⁻⁴ | 1.35 × 10¹¹ | 2.17 × 10⁵ | 6.2(1.2) × 10⁵ |
| Donor 3 | 3.1(0.5) | 1.50 × 10⁻⁴ | 2.80 × 10¹¹ | 2.70 × 10⁵ | 1.0(0.2) × 10⁶ |
| Donor 4 | 3.7(1.6) | 1.50 × 10⁻⁴ | 3.34 × 10¹¹ | 2.95 × 10⁵ | 1.1(0.5) × 10⁶ |
| Donor 5 | 4.0(1.3) | 1.50 × 10⁻⁴ | 3.61 × 10¹¹ | 2.94 × 10⁵ | 1.2(0.4) × 10⁶ |

No previous receptor/cell data for 1D3 antigenic sites on neutrophils has been available.

To explore the sensitivity of the method, run 2 with dim (donor 2), medium (donor 3), and bright (donor 1) donors for 1D3-FITC fluorescence were analyzed. This time, titers below 1 $\mu L$ (0.4 $\mu g$ 1D3-FITC/0.5 $\mu g$ KC56-PE) of dual marker were added for more sensitivity in the analyses, especially for the presence of soluble 1D3 antigen in the serum. The raw 1D3-FITC fluorescent marker intensities are listed in Table VIII.

TABLE VIII

Dual marker, 1D3-FITC/KC56-PE, titers with 100 $\mu L$ of whole blood; run 2 with 3 donors; values in parentheses are standard deviations (SD), no SD was given to values near or below the discriminator line.

| | mean channel 1D3-FITC fluorescence intensity | | |
|---|---|---|---|
| $\mu L$ of dual marker | donor 1 | donor 2 | donor 3 |
| .020 | 1.20 | — | 0.20 |
| .040 | 3.492(0.928) | — | 0.60 |
| .067 | 5.425(1.990) | 0.15 | 0.744 |
| .100 | 6.095(2.358) | 0.20 | 1.366 |
| .200 | 18.20(8.63) | 0.237 | 5.168(1.981) |
| .400 | 31.02(13.96) | 0.337 | 9.077(3.800) |
| 1.00 | 45.18(18.73) | 1.366 | 15.19(6.13) |
| 2.00 | 57.37(21.39) | 2.623(1.023) | 18.85(7.11) |
| 5.00 | 71.37(25.40) | 3.589(1.753) | 24.88(8.94) |
| 10.0 | 78.39(26.70) | 4.042(2.046) | 26.07(9.28) |
| 20.0 | 80.32(31.26) | 4.420(2.268) | 27.68(10.33) |
| 30.0 | 87.57(33.88) | 5.696(2.947) | 30.58(12.60) |

Aside from the large variability in the maximum fluorescence intensity that was reached at high titers of 1D3-FITC with the three normal donors, the intensities at low titers are also extremely variable. The latter region in the titrations is very sensitive to the presence of soluble 1D3 antigen, which will tend to react first with the soluble 1D3-FITC marker because of its much greater kinetic energy and thus greater number of collisions per unit time. If the cut-off for observable fluorescence signals from targeted cells is taken as one mean channel unit, then the increasing order of soluble 1D3 antigen in the three donors is 1, 3, 2 at titers of <0.020, between 0.100 and 0.067, and between 1.00 and 0.400 $\mu L$ of dual marker, or at <0.00880, ~0.0268, and ~0.16 $\mu g$ of 1D3-FITC. With a valence of 10 for the labelled IgM antibody, 1D3-FITC, and a molecular weight of 862,500 Daltons, crude estimates of the concentration of soluble 1D3 antigen in 100 $\mu L$ of whole blood were <0.92, ~3.1, and ~18.5 nM for donors 1, 3, and 2, respectively.

The raw data were analyzed in the same way as for the previous run 1 and results are shown in Table IX. Initial estimates of K values from the slopes of $\theta_2/(1-\theta_2)$ versus $c_{tot}$ plots gave 2.7×10⁸, 0.99×10⁸, and 2.4×10⁸ M⁻¹ for donors 1, 2, and 3, respectively, from data obtained at low concentrations for titers of 0.020 to 5.00 $\mu L$ dual marker. Slopes of corresponding log-log plots produced Hill constants, n=1.03, 1.02, and 1.19, indicative of non-cooperative interaction between occupied receptor sites. Corrections were made to $c_{total}$ values of donors 2 and 3 to compensate for the amount of 1D3-FITC that first reacted with soluble 1D3 antigen and therefore was not detected on the neutrophils by flow cytometry.

TABLE IX

Binding Data Analysis: run 2

| μL | $\theta_2$ | $\theta_2/(1-\theta)$ | $c_{tot}$, M × $10^8$ | $c_{tot}$, corr, M × $10^8$ | $c_{soln}$, M × $10^8$ | $c_{surf}$, M × $10^8$ | $c_{sat}$, M × $10^8$ |
|---|---|---|---|---|---|---|---|
| \multicolumn{8}{c}{Donor 1, K = 5.0 × $10^8$ $M^{-1}$} |
| .020 | .0137 | .0139 | .0071 |  | .0028 | .0043 | .31 |
| .040 | .0399 | .0416 | .0143 |  | .0083 | .0060 | .15 |
| .067 | .0620 | .0661 | .0238 |  | .0132 | .0106 | .17 |
| .100 | .0696 | .0748 | .0357 |  | .0150 | .0207 | .30 |
| .200 | .2078 | .2623 | .0713 |  | .0525 | .0188 | .09 |
| .400 | .3542 | .5485 | .1427 |  | .1097 | .0330 | .09 |
| 1.00 | .5159 | 1.066 | .3567 |  | .2132 | .1435 | .28 |
| 2.00 | .6551 | 1.899 | .7135 |  | .3798 | .3337 | .51 |
| 5.00 | .8150 | 4.405 | 1.784 |  | .8810 | .9030 | 1.11 |
| 10.0 | .8952 | 8.542 | 3.567 |  | 1.708 | 1.859 | 2.07 |
| 20.0 | .9172 | 11.08 | 7.135 |  | 2.215 | 4.920 | 5.36 |
| 30.0 | 1.000 | — |  |  | — | — | — |
| \multicolumn{8}{c}{Donor 2, K = 1.8 × $10^8$ $M^{-1}$} |
| .067 | .0263 | .0270 | .0238 | — | — | — | — |
| .100 | .0351 | .0364 | .0357 | — | — | — | — |
| .200 | .0416 | .0434 | .0713 | — | — | — | — |
| .400 | .0592 | .0629 | .1427 | — | — | — | — |
| 1.00 | .2398 | .3154 | .3567 | .2140 | .1752 | .0388 | .16 |
| 2.00 | .4605 | .8536 | .7135 | .5708 | .4742 | .0966 | .21 |
| 5.00 | .6301 | 1.703 | 1.784 | 1.641 | .9461 | .6949 | 1.10 |
| 10.0 | .7096 | 2.444 | 3.567 | 3.424 |  |  |  |
| 20.0 | .7760 | 3.464 | 7.135 | 6.992 |  |  |  |
| 30.0 | 1.000 | — | — |  | — | — | — |
| \multicolumn{8}{c}{Donor 3, K = 5.5 × $10^8$ $M^{-1}$} |
| .020 | .0065 | .0066 | .0071 | — | — | — | — |
| .040 | .0196 | .0200 | .0143 | — | — | — | — |
| .067 | .0243 | .0249 | .0238 | — | — | — | — |
| .100 | .0447 | .0468 | .0357 | .0119 | .0085 | .0034 | .08 |
| .200 | .1690 | .2034 | .0713 | .0475 | .0370 | .0105 | .06 |
| .400 | .2968 | .4221 | .1427 | .1189 | .0767 | .0422 | .14 |
| 1.00 | .4967 | .9869 | .3567 | .3329 | .1794 | .1535 | .31 |
| 2.00 | .6164 | 1.607 | .7135 | .6897 | .2922 | .3975 | .64 |
| 5.00 | .8136 | 4.365 | 1.784 | 1.760 | .7936 | .9664 | 1.19 |
| 10.0 | .8525 | 5.780 | 3.567 |  |  |  |  |
| 20.0 | .9052 | 9.549 | 7.135 |  |  |  |  |
| 30.0 | 1.000 | — | — |  | — | — | — |

Both runs 1 and 2 gave association constants of order $10^7$ to $10^8$ for binding of 1D3-FITC to its antigenic sites on neutrophils, indicating much lower affinity receptors than those for T4-PE ($K \sim 10^{10}$) on CD4 lymphocytes. The continuing increase in fluorescence intensity for some donors at high titers suggested the presence of considerable non-specific binding of marker to neutrophils. Non-specific binding of 1D3-FITC to granulocytes, lymphocytes, and monocytes was verified at titers greater than 10 μL by gating on the separated, resolved regions for these white blood cells in the forward versus side scatter histograms, while accumulating fluorescence emission signals from 1D3-FITC on the cells. Above 10 μL titers of dual marker, another separate region of 1D3-FITC fluorescence intensity began to emerge from below the discriminator level in the dual color fluorescence, 1D3-FITC versus KC56-PE, histogram. Gated on the granulocyte light scatter region, this fluorescence may originate from non-specific labelling of eosinophils and basophils at high marker concentrations. Thus, only $c_{sat}$ values below the standard 10 μL titer were averaged to calculate the number of 1D3 receptors per neutrophil. This time, the COULTER STKS2B hematology analyzer was used to directly obtain the number of neutrophils per 100 μL of whole blood.

TABLE X

Total 1D3 Receptor Concentrations in Samples and No. Receptors/Neutrophil, run 2

| Sample | $c_{sat}$, M × $10^9$ | Sample Vol, L | Total No. Receptors | No. Neutrophils | Receptors /Neutrophil |
|---|---|---|---|---|---|
| Donor 1 | 2.4(1.4) | 1.30 × $10^{-4}$ | 1.88 × $10^{11}$ | 1.3 × $10^5$ | 1.4(0.8) × $10^6$ |
| Donor 2 | 1.8(3.4) | 1.30 × $10^{-4}$ | 1.41 × $10^{11}$ | 2.0 × $10^5$ | 7.0(1.3) × $10^5$ |
| Donor 3 | 2.5(2.9) | 1.30 × $10^{-4}$ | 1.96 × $10^{11}$ | 3.7 × $10^5$ | 5.3(0.6) × $10^5$ |

Larger numbers of 1D3 sites per cell were calculated in run 2, about two to four times previous enumerations (1×$10^5$ to 4×$10^5$) of 3G8 (also an anti-CD16B monoclonal antibody) receptor sites expressed on neutrophils. Therefore, a third run of dual marker, 1D3-FITC/KC56-PE titers with whole blood was carried out and accompanied by a parallel set of samples in which the targeted sites on cells in whole blood were first blocked with a large excess of unmarked 1D3 antibody (10 μL of 30.48 mg/mL antibody concentrate). Each sample of 100 μL of whole blood was incubated for one hour with the unmarked antibody before adding the respective titers of dual marker and compensating 1×PBS buffer solution to obtain constant total volume, and incubating the mixtures for another hour. The equilibrated samples were then Q-PREPed and run on the COULTER Profile II flow cytometer. For samples with marker concentrations that did not show intensity above the discriminator level in histograms, the mean channel position was estimated as the midpoint of the densest part in the histogram above autofluorescence. We noted that 1D3-FITC-blood sample mixtures needed longer incubation times (60 min instead of 10 min) to reach equilibrium than samples with higher affinity IgG antibody, such as CD4 markers, since 1D3, an IgM of about 850,000 Daltons molecular weight, binds to a medium affinity receptor. Results of trials with two donors, in which 10 μL of dual marker, 0.4 μg/μL 1D3-FITC/0.5 μg/μL KC56-PE, were added to 100 μL of whole blood and mixed for varying times are shown in Table XI, and support adoption of the longer mixing time.

TABLE XI

Mixing time dependence of 1D3-FITC fluorescence intensity for dual marker, 1D3-FITC/KC56-PE, and whole blood mixtures.

| | mean channel 1D3-FITC fluorescence intensity | |
|---|---|---|
| Mixing Time, min | donor 1, 3.2 × $10^5$ N/100 μL | donor 2, 2.8 × $10^5$ N/100 μL |
| 2 | 21.96(8.39) | 13.51(6.85) |
| 5 | 23.23(9.35) | 13.82(7.11) |
| 10 | 21.49(8.58) | 11.92(6.12) |
| 20 | 23.20(9.36) | 13.43(6.87) |
| 40 | 25.02(11.22) | 16.02(8.08) |
| 60 | 27.28(12.63) | 15.52(8.05) |

The raw 1D3-FITC fluorescent intensities for the third run and the accompanying blocked sample intensities are listed in Table XII.

TABLE XII

Dual marker, 1D3-FITC/KC56-PE, titers with whole blood and with 1D3 antibody-blocked whole blood for non-specific background correction; run 3 with 3 donors; values in parentheses are standard deviations (SD), no SD was given to values below the discriminator line.

| μL of dual marker | donor 1 | donor 2 | donor 3 |
|---|---|---|---|
| | sample-mean channel 1D3-FITC fluorescence intensity | | |
| .020 | | | 0.35 |
| .040 | | | 0.85 |
| .067 | | 1.00 | 2.00 |
| .100 | 0.25 | 1.33 | 2.747(0.630) |
| .200 | 0.80 | 3.28 | 4.166(1.350) |
| .400 | 4.766(2.685) | 4.08 | 7.518(2.506) |
| 1.00 | 6.662(4.495) | 7.662(2.942) | 12.26(3.69) |
| 2.00 | 9.366(6.632) | 9.016(3.564) | 14.98(4.38) |
| 5.00 | 12.92(8.70) | 11.52(4.44) | 21.13(5.74) |
| 10.0 | 15.89(10.69) | 16.58(6.48) | 24.68(7.49) |
| 20.0 | 20.86(13.04) | 21.49(8.92) | 29.70(10.67) |
| 30.0 | 23.69(14.25) | 24.67(11.15) | 32.57(12.87) |
| 40.0 | 27.28(16.28) | 26.56(11.78) | 35.42(15.31) |
| 50.0 | 30.72(18.22) | 29.25(13.10) | 37.47(16.51) |
| | blocked sample-mean channel 1D3-FITC fluorescence | | |
| .020 | | | 0.10 |
| .040 | | | 0.10 |
| .067 | | 0.10 | 0.10 |
| .100 | 0.10 | 0.10 | 0.10 |
| .200 | 0.10 | 0.12 | 0.13 |
| .400 | 0.13 | 0.13 | 0.14 |
| 1.00 | 0.15 | 0.15 | 0.15 |
| 2.00 | 0.20 | 0.18 | 0.20 |
| 5.00 | 0.57 | 0.70 | 0.60 |
| 10.0 | 1.20 | 1.30 | 2.00 |
| 20.0 | 3.801(1.869) | 3.595(1.386) | 3.758(1.824) |
| 30.0 | 4.548(2.331) | 4.549(2.060) | 4.785(2.501) |
| 40.0 | 6.060(3.441) | 5.860(2.912) | 6.099(3.509) |
| 50.0 | 7.543(4.077) | 7.202(3.628) | 7.502(4.405) |

The blocked samples showed the characteristics of competitive 1D3-FITC/1D3 binding (See Example. 5). When the fluorescence intensity versus concentration of labelled 1D3 was plotted on linear-log paper, extrapolated half-titration points of 98, 86, and 190 μg 1D3-FITC in the presence of 304.8 μg 1D3 were obtained for donors 1, 2, and 3, respectively. These data agree with 1D3/1D3-FITC competitive binding results which showed higher affinity constants for 1D3-FITC compared to 1D3 binding to their antigenic sites on neutrophils. The sample intensities were further used in the analyses for which results appear in Table XIII. Preliminary estimates of K values from the slopes of $\theta_2/(1-\theta_2)$ versus $c_{tot}$ plots gave $0.71 \times 10^8$, $0.69 \times 10^8$, and $1.1 \times 10^8 M^{-1}$ for donors 1, 2, and 3, respectively, at low concentrations corresponding to titers of dual marker between 0.020 and 2.00 μL.

TABLE XIII

Binding Data Analysis: run 3

| μL | $\theta_2$ | $\theta_2/(1-\theta_2)$ | $c_{tot}$, M × 10$^8$ | $c_{soln}$, M × 10$^9$ | $c_{surf}$, M × 10$^8$ | $c_{sat}$, M × 10$^8$ |
|---|---|---|---|---|---|---|
| | | | Donor 1, K = 1.5 × 10$^8$ M$^{-1}$ | | | |
| .100 | .0081 | .0082 | .0309 | .0055 | .0027 | .33 |
| .200 | .0260 | .0267 | .0618 | .0178 | .0440 | 1.7 |
| .400 | .1551 | .1836 | .1237 | .1224 | .0013 | .01 |
| 1.00 | .2169 | .2770 | .3092 | .1847 | .1245 | .57 |
| 2.00 | .3049 | .4386 | .6183 | .2924 | .3259 | 1.1 |
| 5.00 | .4206 | .7259 | 1.546 | .4839 | 1.062 | 2.5 |
| 10.0 | .5172 | 1.071 | 3.092 | .7140 | 2.378 | 4.6 |
| 20.0 | .6790 | 2.115 | 6.183 | 1.410 | 4.773 | 7.0 |
| 30.0 | .7711 | 3.369 | 9.275 | 2.246 | 7.029 | 9.1 |
| 40.0 | .8880 | 7.928 | 12.37 | 5.285 | 7.085 | 8.0 |
| 50.0 | 1.000 | — | 15.46 | — | — | — |
| | | | Donor 2, K = 2.1 × 10$^8$ M$^{-1}$ | | | |
| .067 | .0342 | .0354 | .0206 | .0168 | .0038 | .11 |
| .100 | .0455 | .0477 | .0309 | .0227 | .0082 | .18 |
| .200 | .1121 | .1262 | .0618 | .0601 | .0017 | .01 |
| .400 | .1395 | .1621 | .1237 | .0772 | .0465 | .33 |
| 1.00 | .2619 | .3548 | .3092 | .1689 | .1403 | .53 |
| 2.00 | .3082 | .4455 | .6183 | .2121 | .4062 | 1.3 |
| 5.00 | .3938 | .6496 | 1.546 | .3093 | 1.237 | 3.1 |
| 10.0 | .5668 | 1.308 | 3.092 | .6228 | 2.469 | 4.3 |
| 20.0 | .7347 | 2.769 | 6.183 | 1.318 | 4.865 | 6.6 |
| 30.0 | .8434 | 5.386 | 9.275 | 2.565 | 6.710 | 7.9 |
| 40.0 | .9080 | 9.869 | 12.37 | 4.699 | 7.671 | 8.4 |
| 50.0 | 1.000 | — | 15.46 | — | — | — |
| | | | Donor 3, K = 2.8 × 10$^8$ M$^{-1}$ | | | |
| .020 | .0093 | .0094 | .0062 | .0033 | .0029 | .31 |
| .040 | .0227 | .0232 | .0124 | .0083 | .0041 | .18 |
| .067 | .0534 | .0564 | .0206 | .0201 | .0005 | .01 |
| .100 | .0733 | .0791 | .0309 | .0282 | .0027 | .04 |
| .200 | .1112 | .1251 | .0618 | .0447 | .0171 | .15 |
| .400 | .2006 | .2509 | .1237 | .0896 | .0341 | .17 |
| 1.00 | .3272 | .4863 | .3092 | .1737 | .1355 | .41 |
| 2.00 | .3998 | .6661 | .6183 | .2379 | .3804 | .95 |
| 5.00 | .5639 | 1.293 | 1.546 | .4618 | 1.084 | 1.9 |
| 10.0 | .6587 | 1.930 | 3.092 | .6893 | 2.403 | 3.6 |
| 20.0 | .7926 | 3.822 | 6.183 | 1.365 | 4.818 | 6.1 |
| 30.0 | .8692 | 6.645 | 9.275 | 2.373 | 6.902 | 7.9 |
| 40.0 | .9453 | 17.28 | 12.37 | 6.171 | 6.199 | 6.5 |
| 50.0 | 1.000 | — | 15.46 | — | — | — |

The binding constant and $c_{sat}$ values are similar to those obtained in the second series of trials, and gave numbers of receptors per neutrophil, appearing in Table XIV.

TABLE XIV

Total 1D3 Receptor Concentrations in Samples and No. Receptors/Neutrophil, run 3

| Sample | $c_{sat}$, M × 10$^9$ | Sample Vol, L | Total no. Receptors | No. Neutrophils | Receptors/Neutrophil |
|---|---|---|---|---|---|
| Donor 1 | 5.0(4.6) | 1.50 × 10$^{-4}$ | 4.52 × 10$^{11}$ | 4.4 × 10$^5$ | 1.0(0.9) × 10$^6$ |
| Donor 2 | 2.5(2.0) | 1.50 × 10$^{-4}$ | 2.08 × 10$^{11}$ | 3.6 × 10$^5$ | 5.8(5.0) × 10$^5$ |
| Donor 3 | 1.8(1.4) | 1.50 × 10$^{-4}$ | 1.62 × 10$^{11}$ | 4.7 × 10$^5$ | 3.4(2.6) × 10$^5$ |

Furthermore, to investigate any beneficial effects of a non-specific interaction blocker in the titers of 1D3-FITC with whole blood, a run, in which the dual marker was prepared in 3% BSA, 0.02% sodium azide in 1×PBS and all titers with 100 μL whole blood were adjusted to a total volume of 160 μL with the same BSA buffer, was carried out. The data are presented in Table XV.

TABLE XV

Dual marker, 1D3-FITC/KC56-PE, titers in BSA buffer with whole blood and with 1D3 (304.8 μg)-blocked whole blood.

| μL, dual marker | $c_{tot}$, M × 10$^8$ | mean channel 1D3-FITC intensity sample | blocked sample | $\theta_2$ |
|---|---|---|---|---|
| .010 | .0029 | .19 | — | .0055 |
| .020 | .0058 | .20 | — | .0062 |
| .040 | .0116 | 1.0 | — | .0291 |
| .067 | .0193 | 1.5 | — | .0437 |
| .200 | .0580 | 3.578(1.416) | — | .1042 |
| .400 | .1169 | 4.838(2.078) | .15 | .1410 |
| 1.00 | .2898 | 11.69(4.02) | .16 | .3406 |
| 2.00 | .5797 | 14.26(5.37) | .15 | .4155 |
| 5.00 | 1.449 | 19.11(6.83) | .17 | .5568 |
| 10.0 | 2.898 | 25.88(8.50) | .50 | .7541 |
| 20.0 | 5.797 | 25.42(9.05) | 1.0 | .7407 |
| 30.0 | 8.696 | 31.86(11.96) | 2.0 | .9283 |
| 40.0 | 11.59 | 34.32(13.59) | 3.156(1.314) | 1.000 |
| 50.0 | 14.49 | 32.32(13.65) | 3.688(1.667) | — |

An optimized binding constant $K^{1D3\text{-}FITC}=2.7\times10^8 M^{-1}$ gave an average $c_{sat}=0.30(0.26)\times10^{-8}M$ for titers between 0.010 and 2.00 μL. This, in turn, gave a receptor/neutrophil ratio of 1.4 (1.2)×10$^6$ for a sample with 2.0×10$^5$ neutrophils/100 μL whole blood. Since the results are similar to other runs in which BSA blocker was not used, BSA was not generally necessary in the titrations of labelled or unlabelled antibody with whole blood.

Most notable in the analyses of 1D3-FITC binding data were the unexpectedly high values of receptors per neutrophil for donor 2 in both runs 1 and 2, that showed a dim fluorescence intensity (low mean channel) in the normal titer range as well as an abnormally wide range of 1D3-FITC fluorescence intensities about the mean. Also, donor 1 in run 3 showed an abnormally high standard deviation in its mean channel 1D3-FITC fluorescence intensity. Generally, the magnitude of the mean channel intensity for a tight distribution of fluorescence intensities per cell should be proportional to the relative number of targeted sites per cell. If shed, soluble 1D3 antigen were present in the plasma of blood donors, the analyses of flow cytometry results for these donors would not correctly reflect the binding of fluorescent marker to cell surface antigen alone. Note that the number of soluble 1D3 receptor molecules (vide infra) in the plasma of 100 μL of whole blood, 48×10$^{-9}$ mol/L× 6.022×10$^{23}$ receptors/mol×100×10$^{-6}$ L=28×10$^{11}$ receptors, is greater than the upper bound in the range, 1–9×10$^{11}$, of total number of 1D3 receptors on neutrophils in 100 μL of whole blood. Thus, calculations of receptors per cell and binding constants need a correction for the presence of soluble antigen in the whole blood sample.

To compare the effects of a naturally-occurring proteinaceous fluorescence label, phycoerythrin, against FITC, the 1D3-PE conjugate was used. The product could not be separated from pure 1D3 antibody, but was used as a mixture with an F/P=0.41. Concentrations of 1D3/1D3-PE were calculated from an absorbance reading at 280 nm for total protein and then using an average molecular weight, 850,000+(0.41×240,000)=948,400 g/mol. A correction for fluorescence intensities was not needed since the fraction of surface sites occupied by 1D3/1D3-PE, $\theta_2$, is calculated from the ratios of $\Delta F/\Delta F_{max}$, from which the correction would cancel out. Thus, variable amounts of dual marker, 1D3/1D3-PE (0.5124 μg/μL) and KC56-FITC (0.1937 μg/μL), were mixed with 100 μL of whole blood, Q-PREPed, and run on the flow cytometer to obtain the intensity data listed below. Fluorescence intensity was also measured for similar mixtures that were first blocked with an excess (304.8 μg) of unlabelled 1D3 antibody. Only a single marker was used at high titers between 20.0 and 50.0 μL. Data are given in Table XVI.

TABLE XVI

Dual marker, 1D3-PE/KC56-FITC, titers with whole blood and 1D3-blocked whole blood.

| μL, dual marker | μg 1D3 | $c_{tot}$, M × 10$^8$ | mean channel 1D3-PE intensity sample | blocked sample | $\theta_2$ |
|---|---|---|---|---|---|
| .040 | | .018 | 1.0 | — | .0421 |
| .067 | | .030 | 1.3 | — | .0548 |
| .100 | | .045 | 2.0 | — | .0843 |
| .200 | | .090 | 4.254(2.131) | — | .1793 |
| .400 | .0706 | .180 | 5.997(2.811) | 0.13 | .2528 |
| 1.00 | .1766 | .450 | 8.480(3.443) | 0.17 | .3575 |
| 2.00 | .3531 | .900 | 9.119(3.068) | 0.30 | .3844 |
| 5.00 | .8829 | 2.25 | 11.05(3.14) | 0.63 | .4658 |
| 10.0 | 1.766 | 4.50 | 14.25(3.89) | 2.2 | .6007 |
| 20.0 | 3.531 | 9.00 | 17.79(5.39) | 5.494(2.167) | .7500 |
| 30.0 | 5.297 | 13.5 | 21.51(6.41) | 8.977(3.230) | .9068 |
| 40.0 | 7.063 | 18.0 | 23.72(7.03) | 10.14(3.70) | 1.000 |
| 50.0 | 8.829 | 22.5 | 22.72(7.12) | 11.39(4.13) | — |

The best fit for titers between 0.040 and 0.400 μL was obtained with an average affinity constant, $K=2.8\times10^8 \, M^{-1}$, to give an average $c_{sat}=1.3$ (0.7)×10$^{-9}$M and a total no. of receptors=1.17×10$^{11}$. Therefore, for this donor with 4.7×10$^5$ neutrophils per 100 μL of whole blood, as measured on the COULTER STKS hematology instrument, the number of receptors per neutrophil was 2.5 (1.3)×10$^5$. These figures compare well with the range determined for binding of 1D3-FITC to neutrophil receptor sites, and with previous results for 3G8 antibody binding to neutrophil receptor sites. This blocked sample also showed the characteristics of competitive 1D3-PE/1D3 binding when the fluorescence intensity versus labelled 1D3-PE concentration was plotted on linear-log paper. An extrapolated half-titration point was located at 9.8 μg (6.458×10$^{-8}$M) 1D3-PE in the presence of 304.8 μg (224.1×10$^{-8}$M) 1D3. Thus, $k_{rel}=[L^*]/[L]^-L^*/L=$ 6.458×10$^{-8}$/224.1×10$^{-8}$= 0.0288, which is also=$K^L/K^{L*}=$ $K^L/2.8\times10^8$ so that $K^{1D3}=8.1\times10^6 M^{-1}$.

Moreover, a run similar to run 3 was carried out to show competition for 1D3 and 3G8 sites on neutrophils. This run with varying titers of dual marker, 1D3-FITC/KC56-PE, and 100 μL of whole blood was accompanied by a parallel set of samples to each of which a large excess of unmarked 3G8 antibody (7.25 μL of 42.08 mg/mL antibody concentrate) was first added. Each sample of 100 μL of whole blood was incubated for one hour with unmarked 3G8 antibody or 1×PBS for the unblocked samples before adding the respective titers of dual marker and compensating 1×PBS buffer solution to give a constant total volume, and incubating the mixtures for another hour. The equilibrated samples were Q-PREPed and run on the COULTER Profile II flow cytometer in the usual way. The fluorescence intensity data for unblocked and blocked samples are summarized in Table

XVII.

TABLE XVII

Dual marker, 1D3-FITC/KC56-PE, titers with whole blood and with 3G8 antibody-blocked whole blood samples; values in parentheses are standard deviations (SD), no SD was given to values below the discriminator line.

|  |  | mean channel 1D3-FITC intensity | |
| --- | --- | --- | --- |
| µL dual marker | conc 1D3-FITC, M × 10⁸ | unblocked samples | blocked samples |
| .400 | .1237 | 4.752(2.382) | 0.15 |
| 1.00 | .3092 | 13.17(7.11) | 0.20 |
| 2.00 | .6183 | 25.28(12.04) | 0.30 |
| 5.00 | 1.546 | 20.02(11.82) | 0.70 |
| 10.0 | 3.092 | 47.22(20.23) | 1.30 |
| 20.0 | 6.183 | 24.33(15.38) | 2.00 |
| 30.0 | 9.275 | 51.83(26.45) | 3.617(1.532) |
| 40.0 | 12.37 | 56.80(28.82) | 4.140(1.831) |
| 50.0 | 15.46 | 58.40(31.42) | 4.852(2.342) |

The complete extinction of 1D3-FITC fluorescence intensity by excess 3G8 antibody at titers below the standard 10 µL one, for which eosinophils and basophils are not non-specifically marked, shows that 3G8 blocks the epitope on the CD16b antigen (FcγRIIIB) that 1D3-FITC would normally bind on neutrophils. Thus, binding of 3G8 to a different epitope of CD16 can create steric hindrance which prevents binding of 1D3-FITC to its epitope on the CD16b antigen. An initial estimated value of $K=1.4\times10^8 M^{-1}$ for 1D3-FITC binding was used to calculate an optimized value of $K^{1D3\text{-}FITC}=2.0\times10^8 M^{-1}$ and $c_{sat}=7.5\times10^{-9} M$ for titers between 0.400 and 2.00 µL of dual marker. For a blood sample containing $3.3\times10^5$ neutrophils/100 µL whole blood, these figures gave $2.2\times10^6$ receptors/neutrophil. Also, extrapolation of the blocked sample data between 20.0 and 50.0 µL of dual marker in a plot of mean channel 1D3-FITC intensity versus concentration of 1D3-FITC gave a crude estimate of $6.78\times10^{-4} M$ for the 1D3-FITC total concentration at the half-titration point (mean channel intensity=½ (58.40) =29.20). With a total 3G8 concentration of $1.21\times10^{-5} M$ in each sample, then $k_{rel}{}^-L^*/L=56.0=K^L/K^{L^*}$, so that $K^{3G8}=1.1\times10^{10} M^{-1}$.

In addition, a second run with reversed labels was done to demonstrate competition for 1D3 and 3G8 sites on neutrophils. This time a run with varying titers of dual marker, 3G8-FITC(0.075 µg/µL)/KC56-PE(0.5 µg/µL), and 100 µL of whole blood was accompanied by a parallel set of samples to each of which a large excess of unmarked 1D3 antibody (8.7 µL of 35.09 mg/mL antibody concentrate) was first added. The samples were then treated the same way as in the previous run and intensities were measured on the COULTER Profile II. The average F/P ratio for 3G8-FITC was 6.41 for two pooled fractions, one containing 82% by weight of the product at an F/P=6.18 and the other with 18%, and an F/P=7.46. The data are displayed in the Table VIII.

TABLE XVIII

Dual marker, 3G8-FITC/KC56-PE, titers of whole blood and 1D3-blocked whole blood.

|  |  | mean channel 3G8-FITC intensity | | | |
| --- | --- | --- | --- | --- | --- |
| µL dual marker | conc 3G8-FITC, M × 10⁸ | sample | blocked sample | $\theta_2$ | $\theta_2/(1-\theta_2)$ |
| .010 | .0029 | .524(.325) | .13 | .0111 | .0112 |
| .020 | .0059 | 1.168(.649) | .14 | .0247 | .0253 |
| .040 | .0118 | 2.334(.689) | .507(.231) | .0494 | .0520 |
| .067 | .0197 | 4.438(1.335) | .938(.394) | .0939 | .1036 |
| .100 | .0295 | 6.787(1.815) | 1.643(.336) | .1437 | .1678 |
| .200 | .0591 | 11.42(2.95) | 4.122(.720) | .2417 | .3187 |
| .400 | .1181 | 17.60(4.24) | 6.622(1.065) | .3726 | .5939 |
| 1.00 | .2954 | 26.51(6.07) | 17.94(3.25) | .5612 | 1.279 |
| 2.00 | .5907 | 32.71(8.25) | 23.07(3.47) | .6924 | 2.251 |
| 5.00 | 1.477 | 33.50(9.36) | 34.42(8.85) | .7091 | 2.438 |
| 10.0 | 2.954 | 35.68(11.90) | 36.97(12.49) | .7553 | 3.087 |
| 20.0 | 5.907 | 38.81(14.79) | 38.29(15.71) | .8215 | 4.602 |
| 30.0 | 8.861 | 44.19(20.53) | 41.72(18.32) | .9354 | 14.48 |
| 40.0 | 11.81 | 44.86(22.08) | 46.01(22.96) | .9496 | 18.84 |
| 50.0 | 14.77 | 47.24(24.06) | 49.41(24.13) | 1.000 | — |

An initial value of $K=3.85\times10^8 M^{-1}$ and $n=0.94$ were estimated from the slopes of $\theta_2/(1-\theta_2)$ versus $c_{tot}$ and the corresponding log-log plots, respectively. An optimized $K^{3G8\text{-}FITC}=1.0\times10^9 M^{-1}$ gave $c_{sat}=1.27\times10^{-9} M$; and, with a blood sample containing $4.76\times10^5$ neutrophils/100 µL of whole blood, the number of 3G8 receptors/neutrophil=$2.5\times10^5$.

Figure 2:
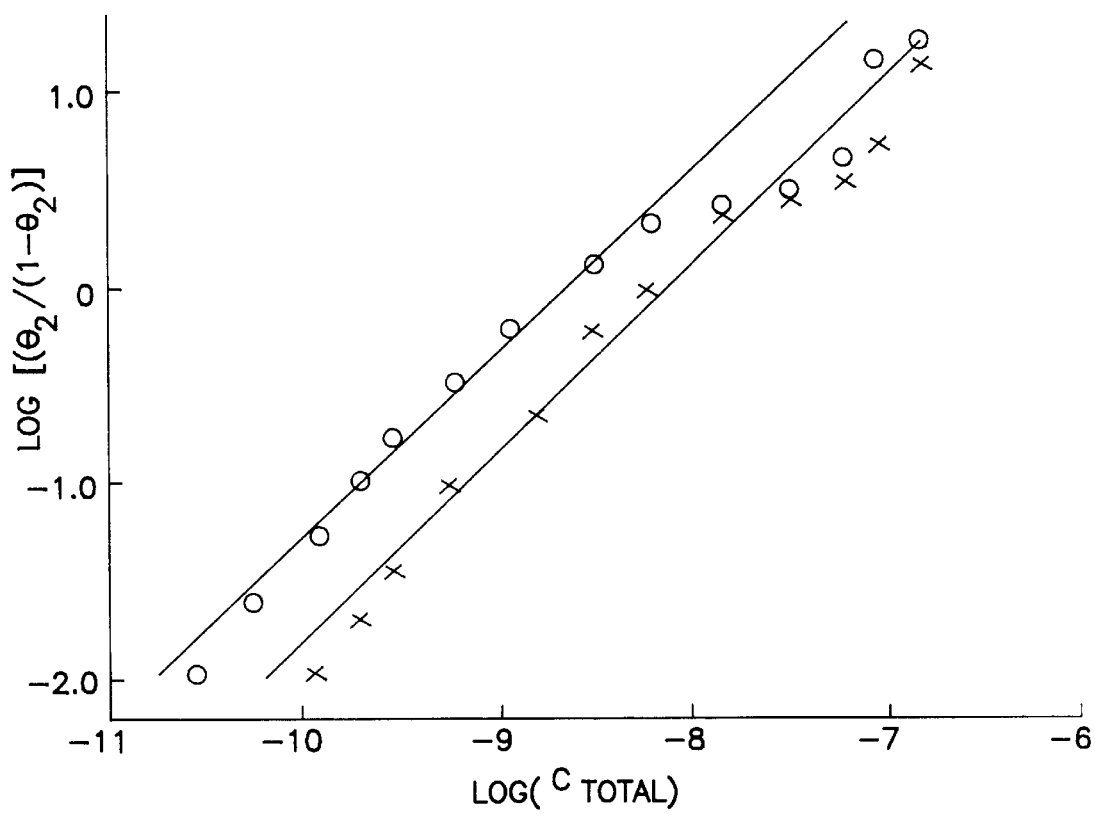
FIG. 2 graphically displays the log-log dependence of the ratio of bound-to-unbound fraction, $[\theta_2/(1-\theta_2)]$, of 3G8-FITC marker on neutrophils in whole blood, as determined by flow cytometry from mean channel 3G8-FITC fluorescence intensities for various titers, on the total molar concentration of 3G8-FITC marker.

Log-log plots for the blocked sample and the unblocked sample are shown in FIG. 2. The slopes (n and n') of both curves near $\log[\theta_2/(1-\theta_2)]=0$ are about the same, 0.940 and 0.936, which is indicative of competitive binding between 1D3 and 3G8-FITC for sites on the FcγRIIIB receptor on the surface of neutrophils. Competitive binding can be shown by first writing the Langmuir equation incorporating the Hill constant for 3G8-FITC binding in the absence of inhibitor (unprimed) and in the presence of inhibitor (primed) at the half-titration point as follows, $$\theta_2/(1-\theta_2)=1=Kc^n \text{ at } \theta_2=0.5, \text{ and}$$

$$\theta_2'/(1-\theta_2')=1=K'c'^{n'} \text{ at } \theta_2'=0.5.$$

Then, $Kc^n=K'c'^{n'}$, so that for identical slopes, $n'=n$, at the half-titration point in the non-cooperative n=1 case, $$K/K'=c'/c,$$

which is analogous to the condition for competitive binding that was derived from mass action law considerations in a previous section, when the second equation is written for the inhibitor binding instead of the marker. Note that c'>c when $\theta_2'=\theta_2$, to compensate for inhibitor binding. At the half-titration point of the blocked sample, i.e., at a mean channel intensity of ½(49.41)=24.7, the total concentration of 3G8-FITC was $7.76\times10^{-9} M$ as read from the graph in FIG. 2. Also, the total concentration of 1D3 in each sample was $2.26\times10^{-6} M$, so that $K_{rel}{}^-L^*/L=3.43\times10^{-3}=K^L/K^{L^*}$ and $K^{1D3}=3.4\times10^6 M^{-1}$. This unusually low and indirectly obtained association constant for 1D3 antibody may have been artificially produced by incomplete blocking via steric hindrance of 3G8 antigenic epitopes on neutrophils by the larger IgM antibody, 1D3. By the same token, the wide difference in $K^{3G8}$ values determined by 3G8/1D3-FITC competition, $1.1\times10^{10} M^{-1}$, and by 3G8/3G8-FITC competition (See Example 5), $5.1\times10^7 M^{-1}$, implies that the indirect determination of 3G8 affinity by extrapolation in 3G8/1D3-FITC competition gave an artificially high $K^{3G8}$ value.

EXAMPLE 5

Competitive Antibody Binding to Soluble Antigen and Antigen on Biological Cells by Flow Cytometry—the Cytoimmunoassay (CYIA)

We used one of the four variations of an immunoassay previously described [42], the antibody competition, and one of the three classes of immunoassay previously described [42], the antibody capture, but without the presence of pure or partially pure antigen and without an extraneous solid support such as microtiter plates or beads for any component of the reaction, as recommended for quantitating antigen in competition assays. Rather, a competitive binding protocol of unlabelled and labelled antibody for the same antigen in solution and on the surface of cells was used so that flow cytometry could be used as a sensitive technique to determine the concentration of soluble antigen in blood plasma, the specific affinity constant for binding of unmarked antibody to its antigen on a cell surface once the specific affinity constant of marked antibody was determined by other means, and the average affinity constant. The results of the technique may also be used to correct binding constant and receptor populations for the presence of soluble antigen in blood plasma. The following protocol in the variable concentration of unmarked antibody and constant concentration of marked antibody mode, that is very sensitive to changes in fluorescence intensity at the low, unmarked antibody concentration, demonstrates the method. For optimum sensitivity, the concentration of marked antibody alone in the control should be chosen so that about 90% of saturation of receptor sites on targeted cells is obtained.

10 μL of variable amounts (1/100 to 100× the standard amount of 4 μg) of unmarked 1D3 antibody were first incubated for one hour with whole blood samples (100 μL), followed by an additional one hour incubation of all the mixtures with the standard 10 μL of dual fluorescent marker, 1D3-FITC/KC56-PE. All samples were then Q-PREPed and analyzed on the COULTER Profile II flow cytometer. The mean channel 1D3-FITC fluorescence intensity thus recorded was plotted (FIG. 3) against the concentration in mol/L of unmarked 1D3 antibody that was used per sample. A small rise, compared to the control without unmarked antibody, and then fall in fluorescence intensity at the lowest titers in the plot indicated reaction of soluble antigen with unmarked antibody to increase the intensity of fluorescent antibody on cells, which labelled antibody might otherwise bind to soluble antigen and not be detected by flow cytometry. This sensitivity in fluorescence intensity on targeted cells due to the presence of soluble antigen could not be achieved in the reverse competitive antibody mode, i.e., variable concentration of marked antibody and constant concentration of unmarked antibody, that is described in the previous section, because of the very low fluorescence intensities at low variable titers at which binding occurs to soluble antigen. A definite maximum in the curves in FIG. 3 for runs 1 and 2 was not observed; however, the titration curve for run 3 (vide infra) in FIG. 4 did show a clear maximum at low titers. The latter phase in the graph (FIG. 3) is followed by a sigmoidal curve in which there is a smooth decrease in intensity as unmarked antibody took up antigenic sites on the targeted cell surface in competition with marked antibody. This decrease was log-linear over one to two decades of 1D3 antibody concentration. Finally, a plateau was reached at a lower level where all sites were filled by unmarked antibody and the intensity corresponded to the spontaneous fluorescence of the cells. The point at which the curve passes below the intensity of the control at low concentrations of unmarked 1D3 can be used to indicate the end-point in the titration of free soluble antigen in the blood plasma. The intensity of the control is reached when enough unmarked 1D3 antibody has been added to react with soluble antigen so that the concentration of marker, 1D3-FITC, available to the targeted cells is the same as it was in the control. A more exact determination of the end-point in the sigmoidal curve can be made by replotting the data on probability paper, on which the ordinate scale is graduated according to the area under a normal distribution function. If the shape of the frequency distribution of mean channel intensities in the sigmoidal curve is very nearly that of the theoretical distribution, then the polygon thus obtained will be very close to a straight line. Graphical interpolation for the endpoint is made to the point at which the curve begins to deviate widely from linearity. The mean channel intensities were first converted to percentages (p) of the mean channel of the control or maximum intensity, and then plotted on a linear ordinate scale for the logit function, $l=\ln[p(100-p)]$. This type of analysis has been frequently carried out when the results of radio-activity measurements of samples were analyzed [43]. Data for a dim donor in run 1 (single whole blood-1D3 antibody-dual marker sample per titer point) are shown in Table XIX, and similar data for a second dim donor in run 2 (samples in triplicate per titer point) are given in the same Table XIX.

TABLE XIX

Mean channel 1D3-FITC fluorescence intensities per aliquot of unmarked 1D3 antibody added to 100 μL whole blood for runs 1 and 2, and also per aliquot of 1D3-FITC added to 100 μL whole blood for run 1; values in parentheses are standard deviations (SD), no SD was given to values below the discriminator line.

mean channel 1D3-FITC fluorescence intensity

| μg 1D3 or 1D3-FITC | Run 1 1D3-FITC alone | Run 2 trial 1 | Run 2 trial 2 | Run 2 trial 3 | mean |
|---|---|---|---|---|---|
| .040 | 3.545 (1.802) | 4.924 (2.724) | 5.119 (2.955) | 5.206 (3.005) | 5.083 |
| .080 | 3.110 (1.627) | 5.084 (2.795) | 5.013 (2.777) | 5.028 (2.795) | 5.042 |
| .160 | 3.440 (2.250) | 0.4 | 5.066 (2.824) | 5.012 (2.713) | 5.089 (2.842) | 5.056 |
| .400 | 3.528 (2.426) | 0.8 | 4.910 (2.687) | 4.826 (2.654) | 4.553 (2.412) | 4.763 |
| .800 | 3.098 (1.723) | 1.4 | 4.660 (2.469) | 4.743 (2.670) | 4.727 (2.712) | 4.710 |
| 2.00 | 2.5 | 2.774 (1.251) | 4.258 (2.222) | 4.433 (2.345) | 4.211 (2.175) | 4.301 |
| 4.00 | 2.0 | 3.496 (1.751) | 3.141 (1.423) | 3.940 (2.021) | 3.925 (2.062) | 3.669 |
| 8.00 | 1.5 | 4.875 (2.635) | 3.051 (1.480) | 3.089 (1.445) | 3.008 (1.400) | 3.049 |
| 12.0 | 1.0 | 5.551 (3.229) | 2.476 (1.045) | 2.854 (1.357) | 2.456 (1.034) | 2.595 |
| 16.0 | 0.80 | 6.810 (3.933) | 2.502 (1.058) | 2.463 (1.063) | 2.446 (1.062) | 2.470 |
| 20.0 | 0.70 | 8.078 (4.808) | 2.1 | 2.2 | 2.1 | 2.13 |
| 40.0 | 0.65 | | 1.5 | 1.5 | 1.4 | 1.47 |
| 100. | 0.60 | | 1.1 | 1.3 | 1.0 | 1.1 |
| 200. | — | | 0.90 | 0.90 | 0.90 | 0.90 |
| 300. | — | | 0.90 | 0.90 | 0.90 | 0.90 |
| 400. | — | | 0.80 | 0.80 | 0.80 | 0.80 |
| control | | | 4.711 (2.602) | 4.974 (2.803) | 4.942 (2.742) | 4.876 |

Figure 3:
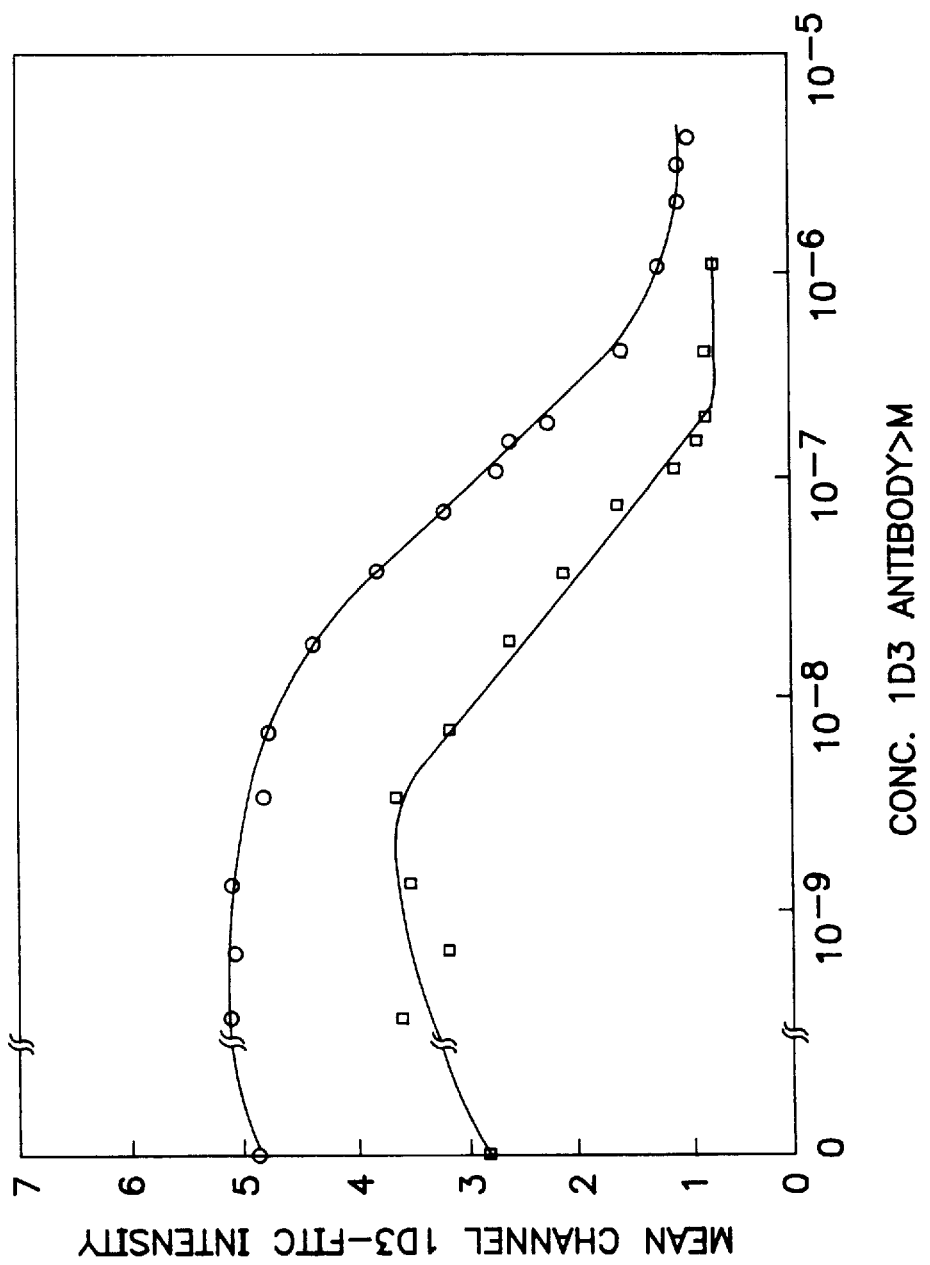
FIG. 3 graphically shows the linear-log dependence of mean channel 1D3-FITC fluorescence intensity on the molar concentration of anti-1D3 antibody in competitive binding runs 1 (squares) and 2 (circles).

The end-points for titration of soluble 1D3 antigen (FcγRIIIB) in runs 1 and 2, as read from the graphs in FIG. 3, are both at about 4 nM of 1D3 antibody (850,000

Daltons). Assuming an antigen valence of one and a 10:1 stoichiometry of antigen:IgM antibody in the region of antigen excess, this corresponds to a 4 nM×10×120 $\mu$L/100 $\mu$L=48 nM concentration of soluble 1D3 antigen in the serum of each dim donor. This figure falls in the middle of the range of soluble 3G8 antigen (also Fc$\gamma$RIIIB) in normal serum, that was determined by ELISA [39] to be 7.3 to 75.9 nmol/L.

A compilation of percentage inhibition values referenced to the maximum intensity in each sigmoidal curve are shown in Table XX for runs 1 and 2.

TABLE XX

Percentage inhibition data for runs 1 and 2.

| | | run 1 | | run 2 | |
|---|---|---|---|---|---|
| $\mu$g 1D3 antibody | conc 1D3, M × 10$^8$ | 1D3-FITC intensity | % inhibition | 1D3-FITC intensity | % inhibition |
| .160 | .157 | — | — | 5.056 | 0 |
| .400 | .392 | 3.528 | 0 | 4.763 | 5.79 |
| .800 | .784 | 3.098 | 12.2 | 4.710 | 6.84 |
| 2.00 | 1.96 | 2.5 | 29.1 | 4.301 | 14.9 |
| 4.00 | 3.92 | 2.0 | 43.3 | 3.669 | 27.4 |
| 8.00 | 7.84 | 1.5 | 57.5 | 3.049 | 39.7 |
| 12.0 | 11.8 | 1.0 | 71.6 | 2.595 | 48.7 |
| 16.0 | 15.7 | .80 | 77.3 | 2.470 | 51.1 |
| 20.0 | 19.6 | .70 | 80.1 | 2.13 | 57.9 |
| 40.0 | 39.2 | .65 | 81.6 | 1.47 | 70.9 |
| 100. | 98.0 | .60 | 83.0 | 1.1 | 78.2 |
| 200. | 196. | — | — | 0.9 | 82.2 |

In run 1, intensity data, summarized in Table XIX, were also collected for titers of 1D3-FITC only with 100 $\mu$L samples of the same blood donor. Analysis of these data gave the following results summarized in Table XXI.

TABLE XXI

Binding Data Analysis, 1D3-FITC only in run 1.

| $\mu$g 1D3 FITC | $\theta_2$ | $\theta_2/(1-\theta_2)$ | $c_{tot}$, M × 10$^8$ | $c_{soln}$, M × 10$^8$ | $c_{surf}$, M × 10$^8$ | $c_{sat}$, M × 10$^8$ |
|---|---|---|---|---|---|---|
| Run 1, K = 1.2 × 10$^8$ M$^{-1}$ | | | | | | |
| .160 | .0990 | .1099 | .1237 | .0916 | .0321 | .32 |
| .400 | .1980 | .2469 | .3092 | .2057 | .1035 | .52 |
| .800 | .3466 | .5304 | .6183 | .4420 | .1763 | .51 |
| 2.00 | .6868 | 2.193 | 1.546 | 1.827 | — | — |
| 4.00 | .8656 | 6.440 | 3.092 | 5.367 | — | — |

The results for runs 1 and 2 were then replotted on probability paper (FIG. 5) as a graph of % inhibition versus concentration of unlabelled antibody. The concentration of unlabelled 1D3 at the half-titration points can then be read from graphs. The relationship, $K_{rel}=K^L/K^{L*}=[L*]/[L]$ at the half-titration point, was derived in the Detailed Description of the Invention supra, and will be used here with data from run 1. Thus, $K_{1D3\text{-}FITC}=K^{L*}=1.2\times10^8 M^{-1}$, $[L*]=3.64\times10^{-8}M$, and $[L]=5.17\times10^{-8}M$ for $L*=3.86\times10^{-8}M$ total 1D3-FITC and $L=5.39\times10^{-8}M$ total 1D3 concentrations at the half-titration point. Since these high concentrations of L* and L are sufficient to saturate the surface receptor sites in run 1 as shown in Table XVI data, then each of the cell surface concentrations of 1D3 and 1D3-FITC will be $\frac{1}{2}\times c_{sat}=\frac{1}{2}\times 0.45\times10^{-8}M=0.22\times10^{-8}M$. Subtracting the latter concentration from the respective total concentrations of 1D3 and 1D3-FITC yields the above values of [L*] and [L]. Then, $K^L=K^{L*}([L*]/[L])=1.2\times10^8(3.64\times10^{-8}/5.17\times10^{-8})$, so that $K_{1D3}=8.4\times10^7 M^{-1}$ and $K_{rel}=0.704$.

The average $K=K_{1D3, 1D3\text{-}FITC}$ can be considered as the geometric mean of the two specific binding constants, i.e. $K=\sqrt{(K_{1D3})(K_{1D3\text{-}FITC})}$. An average K value of $1.0\times10^8 M^{-1}$ was calculated for 1D3/1D3-FITC in run 1.

For run 2, $K_{rel}=[L*]/[L]\cdot L*/L=3.86\times10^{-8}/13.2\times10^{-8})=0.292$ and also $=K^L/K^{L*}=K^L/1.3\times10^8$ for similar donor, so that $K^{1D3}=3.8\times10^7 M^{-1}$.

To investigate the method with a medium intensity (1D3-FITC) donor, data for run 3 were obtained in the same way as for run 2, and are shown in Table XXII.

TABLE XXII

Mean channel 1D3-FITC fluorescence intensities per aliquot of 1D3 antibody added to 100 $\mu$L whole blood for run 3; values in parentheses are standard deviations (SD), no SD was given to values near or below the discriminator line.

mean channel 1D3-FITC fluorescence intensity

| $\mu$g 1D3 antibody | trial 1 | trial 2 | trial 3 | mean |
|---|---|---|---|---|
| .040 | 27.08(13.08) | 27.32(12.95) | 30.47(15.30) | 28.29 |
| .080 | 27.77(12.27) | 29.22(13.01) | 33.51(15.15) | 30.17 |
| .160 | 27.45(11.88) | 29.64(12.90) | 33.11(14.68) | 30.07 |
| .400 | 26.86(11.48) | 26.17(10.97) | 32.16(13.79) | 28.40 |
| .800 | 24.59(10.29) | 24.91(10.54) | 28.83(12.12) | 26.11 |
| 2.00 | 22.37(9.17) | 24.04(9.73) | 25.27(10.39) | 23.89 |
| 4.00 | 19.58(8.21) | 18.08(7.30) | 19.76(7.93) | 19.14 |
| 8.00 | 14.95(5.90) | 16.57(6.74) | 15.92(6.26) | 15.81 |
| 12.0 | 13.00(5.11) | 14.38(5.69) | 13.22(5.38) | 13.53 |
| 16.0 | 11.14(4.61) | 12.68(5.06) | 13.77(5.60) | 12.53 |
| 20.0 | 10.56(4.54) | 11.84(5.06) | 10.22(4.39) | 10.87 |
| 40.0 | 7.134(3.164) | 8.434(3.743) | 7.456(3.319) | 7.675 |
| 100. | 4.354(2.055) | 4.106(1.813) | 4.378(1.987) | 4.279 |
| 200. | 2.20 | 2.30 | 2.20 | 2.23 |
| 300. | 1.50 | 1.60 | 1.50 | 1.53 |
| 400. | 1.25 | 1.20 | 1.50 | 1.32 |
| control | 25.79(11.15) | 28.32(11.97) | 27.17(12.04) | 27.09 |

Figure 4:
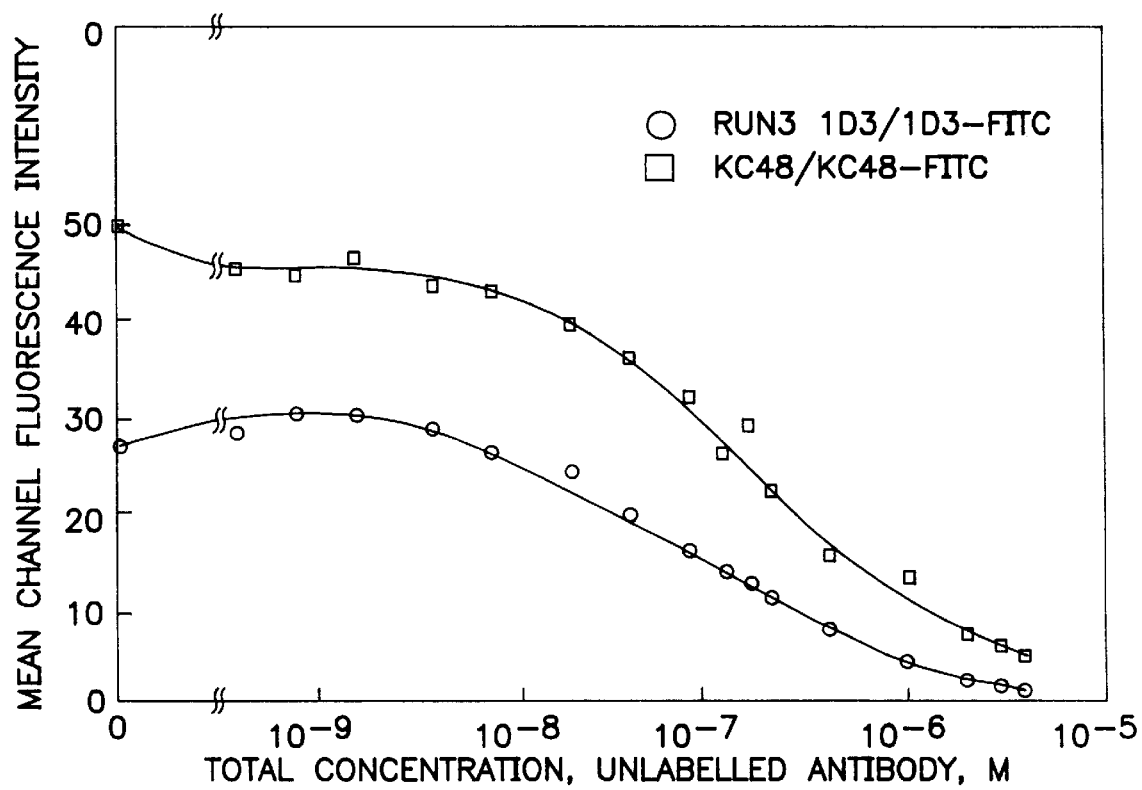
FIG. 4 graphically shows the linear-log dependence of mean channel 1D3-FITC fluorescence intensity on the molar concentration of anti-1D3 antibody in competitive binding run 3 (circles); and the linear-log dependence of mean channel KC48-FITC fluorescence intensity on the molar concentration of anti-KC-48 antibody, in a competitive binding run (squares).

A graph of the mean 1D3-FITC intensity versus the concentration in mol/L of unlabelled 1D3 antibody added to 100 $\mu$L whole blood for run 3 was constructed as shown in FIG. 4, and intersected with the intensity of the control at about 6.0 nM 1D3 antibody. Also, interpolation of the curve in FIG. 5 for run 3 showed larger deviation from linearity at about 6.0 nM 1D3. This endpoint gave 6.0 nM×10×120 $\mu$L/100 $\mu$L=72 nM of soluble 1D3 antigen in the serum of this donor. Run 3 data were analyzed in the same way as for runs 1 and 2 after calculating percentage inhibition values as listed in Table XXIII.

TABLE XXIII

Percentage inhibition data for run 3.

| $\mu$g 1D3 antibody | conc 1D3, M × 10$^8$ | 1D3-FITC intensity | % inhibition |
|---|---|---|---|
| .160 | .157 | 30.07 | 0 |
| .400 | .392 | 28.40 | 5.55 |
| .800 | .784 | 26.11 | 13.2 |
| 2.00 | 1.96 | 23.89 | 20.5 |
| 4.00 | 3.92 | 19.14 | 36.3 |
| 8.00 | 7.84 | 15.81 | 47.4 |
| 12.0 | 11.8 | 13.53 | 55.0 |
| 16.0 | 15.7 | 12.53 | 58.3 |
| 20.0 | 19.6 | 10.87 | 63.8 |
| 40.0 | 39.2 | 7.675 | 74.5 |
| 100. | 98.0 | 4.279 | 85.8 |
| 200. | 196. | 2.23 | 92.6 |
| 300. | 294. | 1.53 | 94.9 |
| 400. | 392. | 1.32 | 95.6 |

Figure 5:
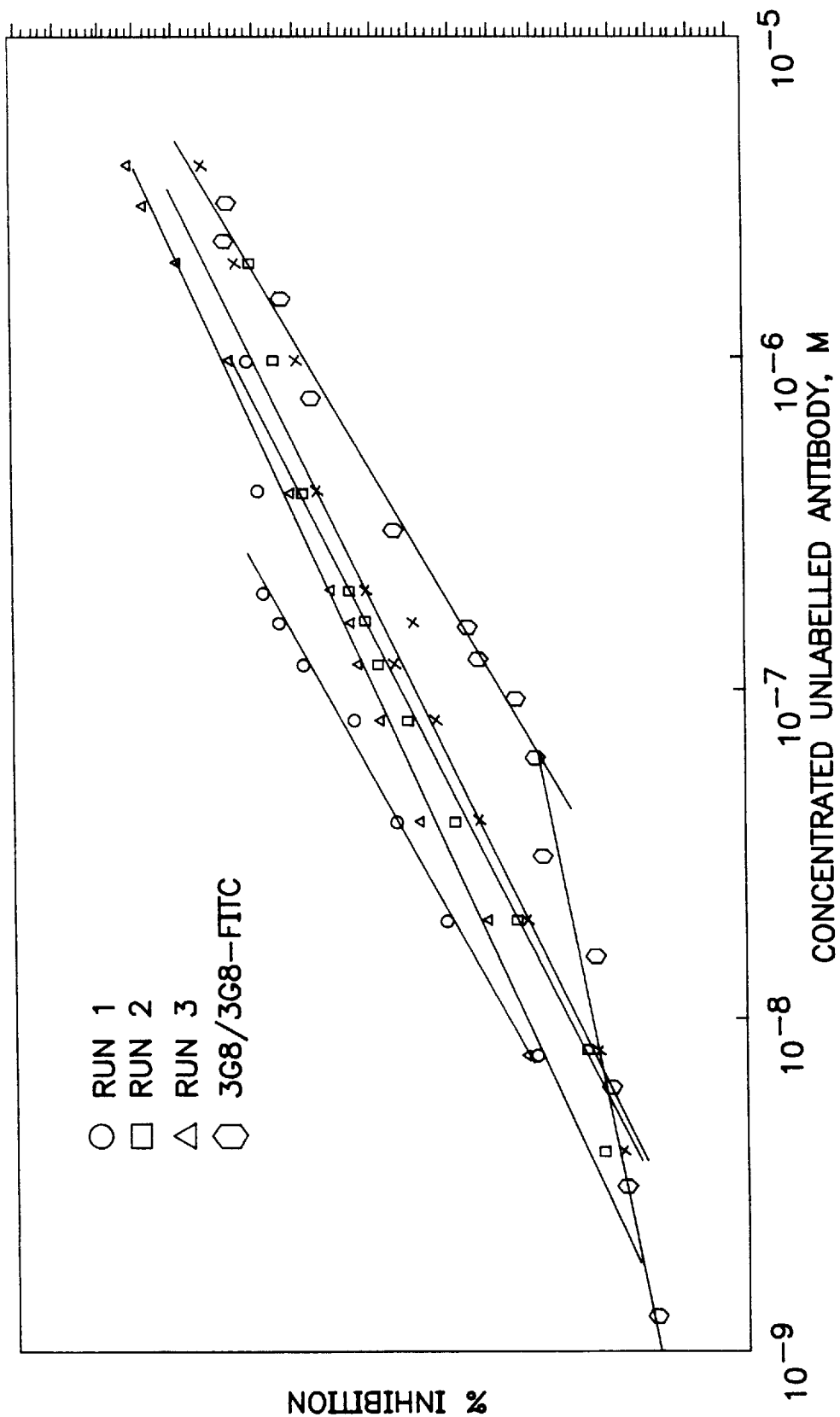
FIG. 5 graphically shows the logistic probability-log dependence of percent inhibition of fluorescent-labelled antibody binding by unlabelled antibody on the molar concentration of unlabelled antibody in several competitive binding runs.

In run 3, $L=9.21\times10^{-8}M$ (9.4 $\mu$g) at the half-titration point from FIG. 5, $L*=3.86\times10^{-8}M$ (4.0 $\mu$g), so that $K_{rel}=[L*]/$ $[L]^-L*/L = 3.86 \times 10^{-8}/9.21 \times 10^{-8} = 0.419$, and also $K^L/K^{L*}$ $\sim K^L/2.1 \times 10^8$ from similar donor, so that $K^{1D3} = 8.8 \times 10^7 M^{-1}$.

The results of the reverse competitive antibody assay, in which the unlabelled antibody concentration is held constant and variable amounts of labelled antibody are added to whole blood, can be analyzed in a similar manner. Thus for donors 1, 2, and 3 of run 3 in the previous section, we calculated the $K_{rel}$ value as follows:

$$K^L = K^{L*}[L*]/[L] \text{ and } K_{rel} = [L*]/[L], \qquad (1)$$
$$K^{1D3} = 1.5 \times 10^8 M^{-1}(71.0 \times 10^{-8} M - 1/2(.50 \times 10^{-8} M))/$$
$$(224.1 \times 10^{-8} M - 1/2(.50 \times 10^{-8} M))$$
$$K^{1D3} = 5.8 \times 10^7 M^{-1} \text{ and } K_{rel} = 0.316,$$

$$K^{1D3} = 2.1 \times 10^{-8} M^{-1}(62.3 \times 10^{-8} M - 1/2(.25 \times 10^{-8} M))/ \qquad (2)$$
$$(224.1 \times 10^{-8} M - 1/2(.25 \times 10^{-8} M))$$
$$K^{1D3} = 5.8 \times 10^7 M^{-1} \text{ and } K_{rel} = 0.278,$$

$$K^{1D3} = 2.8 \times 10^8 M^{-1}(137.7 \times 10^{-8} M - 1/2(.18 \times 10^{-8} M))/ \qquad (3)$$
$$(224.1 \times 10^{-8} |M - 1/2(.18 \times 10^{-8} M))$$
$$K^{1D3} = 1.7 \times 10^{-8} M^{-1} \text{ and } K_{rel} = 0.614.$$

Because of the large total concentrations of both unlabelled and labelled antibody at the half-titration points, the solution concentrations of both species are very nearly equal to the total concentrations, so that $K^L \sim K^{L*}(L*/L)$. These affinity constants of unlabelled 1D3 are similar to those already estimated in competitive antibody runs 1, 2 and 3.

The donor dependence of the relative magnitudes of the two constants, $K^{1D3}$ and $K^{1D3-FITC}$, suggests that both attractive and repulsive interactions of FITC groups with functional groups attached to the FcγRIIIB receptor for 1D3 antibody on the neutrophil cell surface exist. These interactions most probably involve the carboxylate and aromatic hydroxyl groups attached to the fluorescein ring in FITC, and thus introduce an extra pH dependence into the relative equilibrium between marked and unmarked antibody with cell surface receptors. Also, upon conjugation to antibody, each FITC group replaces a positively charged amine group of the antibody. If the Fab structure of 1D3 antibody bears any resemblance to Fab structures of antibody in antigen-antibody complexes that have been characterized [44, 45], then the aromatic FITC rings of 1D3-FITC will perturb by π-cloud interaction the aromatic amino acid residues (Phe, Tyr, Trp) of the antibody in the contact region between antibody-antigen. In the antibodies characterized by X-ray crystallography nearly half the contact residues were aromatic [46] but no particular amino acid composition was found for recognition sites on antigen. Also, the greater negative charge of FITC-conjugated antibodies may lead to a greater electrostatic attraction of antibody for any positively-charged amino acid residues (Arg, Lys) at the binding site on the antigen.

Furthermore, a competitive binding experiment was also done by mixing 100 μL of whole blood with 10 μL titers (1/100 to 280×standard amount of 0.75 μg) of 3G8 antibody and 30 μL of 1×PBS buffer solution for one hour. Then, a fixed amount of dual marker, 0.75 μg 3G8-FITC/5.0 μg KC56-PE in a 10 μL titer was added to the mixture, which was incubated for another hour, Q-PREPed, and analyzed on the flow cytometer. The total concentration of 3G8-FITC in each sample before Q-PREPing was $3.08 \times 10^{-8} M$. The results are listed in Table XXIV.

TABLE XXIV

Competitive 3G8/3G8-FITC binding data.

| μg 3G8 | $c_{total}$, M × $10^8$ | mean channel 3G8-FITC fluorescence intensity | % inhibition |
|---|---|---|---|
| .0075 | .0308 | 36.12(9.35) | 0 |
| .015 | .0616 | 34.31(9.04) | 5.01 |
| .030 | .123 | 34.96(9.19) | 3.21 |
| .075 | .308 | 34.45(9.24) | 4.62 |
| .150 | .616 | 34.19(8.85) | 5.34 |
| .375 | 1.54 | 33.86(8.48) | 6.26 |
| .750 | 3.08 | 32.06(8.72) | 11.24 |
| 1.50 | 6.16 | 31.68(8.25) | 12.29 |
| 2.25 | 9.24 | 30.29(7.61) | 16.14 |
| 3.00 | 12.3 | 28.01(7.36) | 22.45 |
| 3.75 | 15.4 | 27.48(6.98) | 23.92 |
| 7.50 | 30.8 | 19.94(5.10) | 44.79 |
| 18.75 | 77.0 | 10.98(2.23) | 69.60 |
| 37.5 | 154. | 8.401(1.753) | 76.74 |
| 56.25 | 231. | 4.821(0.995) | 86.65 |
| 75.0 | 308. | 4.536(0.956) | 87.44 |
| 210. | 862 | 0.40 | 98.89 |
| 0.0 | control | 31.97(7.82) | — |

Concurrently, variable titers of dual marker, 3G8-FITC/KC56-PE, and 100 μL of whole blood of the same donor, adjusted to a constant total volume of 150 μL with 1×PBS buffer solution, were mixed for one hour, Q-PREPed, and analyzed by flow cytometry. The results are given in Table XXV.

TABLE XXV

Binding data for 3G8-FITC alone.

| μg 3G8-FITC | $c_{total}$, M × $10^8$ | intensity | $\theta_2$ | $\theta_2/(1 - \theta_2)$ |
|---|---|---|---|---|
| .00075 | .00308 | .45 | .0117 | .0118 |
| .0015 | .00616 | .53 | .0138 | .0140 |
| .0030 | .0123 | 1.574(.532) | .0409 | .0426 |
| .0050 | .0205 | 2.788(.715) | .0725 | .0782 |
| .0075 | .0308 | 4.312(1.089) | .1121 | .1263 |
| .015 | .0616 | 8.958(2.111) | .2329 | .3036 |
| .030 | .123 | 13.39(3.12) | .3481 | .5340 |
| .075 | .308 | 23.54(5.43) | .6119 | 1.577 |
| .150 | .616 | 29.20(6.52) | .7590 | 3.149 |
| .375 | 1.54 | 30.71(7.40) | .7983 | 3.958 |
| .750 | 3.08 | 31.97(7.82) | .8310 | 4.917 |
| 1.50 | 6.16 | 37.69(10.67) | .9797 | 48.26 |
| 2.25 | 9.24 | 38.47(11.10) | 1.000 | — |
| 3.00 | 12.3 | 40.42(11.96) | — | — |
| 3.75 | 15.4 | 43.41(13.53) | — | — |

From the slope of the $\theta_2/(1-\theta_2)$ versus $c_{total}$ curve for titers from 0.0030 to 0.075 μg 3G8-FITC, the K value was estimated to be $5.2 \times 10^8 M^{-1}$. An optimized $K^{3G8-FITC} = 7.5 \times 10^8 M^{-1}$ gave $c_{sat} = 1.47 \times 10^{-9} M$, and with $4.95 \times 10^5$ neutrophils/100 μL of whole blood, the number of 3G8 receptors/neutrophil is $2.7 \times 10^5$.

Figure 6:
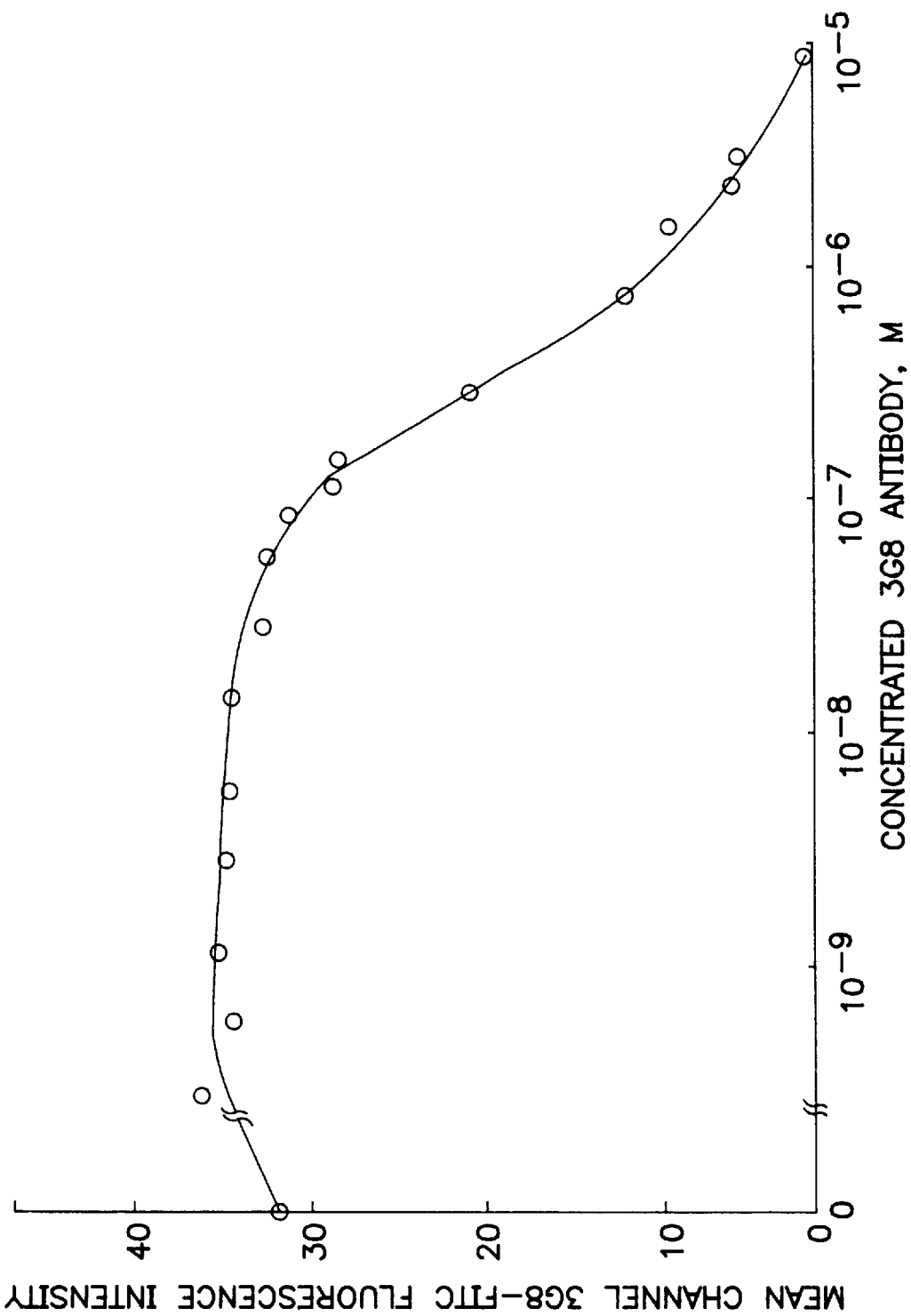
FIG. 6 graphically shows the linear-log dependence of mean channel 3G8-FITC fluorescence intensity on molar concentration of anti-3G8 antibody in a competitive binding run.

A linear-log plot (FIG. 6) of 3G8-FITC mean channel fluorescence intensity versus total concentration of 3G8 antibody in the competitive binding run showed a wide region from $3.08 \times 10^{-10}$ to $5.4 \times 10^{-8} M$ of 3G8 antibody in which the intensity of 3G8-FITC is greater than in the control without any 3G8 antibody. Therefore, the endpoint for titration of soluble 3G8 antigen was taken at the point where the curve drops to the mean channel intensity of the control, i.e., $5.4 \times 10^{-8} M$ 3G8 antibody. For a more accurate estimate of the endpoint the intensity data were recalculated as % inhibition by 3G8 antibody, and then plotted as % inhibition versus concentration of 3G8 antibody on probability paper as shown in FIG. 5. This gave a bimodal curve—a straight line with one slope at low titers of 3G8 antibody for binding of 3G8/3G8-FITC to soluble 3G8 antigen, and another straight line with a steeper slope at higher titers of 3G8 antibody for binding of 3G8/3G8-FITC to 3G8 antigen on neutrophils. The intersection of the two linear portions of the curve at about $7.0 \times 10^{-8}$M 3G8 antibody was taken as the endpoint. Assuming an antigen valence of one and a 1:2 binding stoichiometry between 3G8 (IgG1) antibody and soluble CD16B antigen in the region of antigen excess, we obtain about 70 nM×2×150 µL/100 µL=$2.1 \times 10^2$ nM as the concentration of soluble 3G8 antigen for this blood donor.

At the half-titration point (50% inhibition) in the competitive binding curve for 3G8/3G8-FITC in FIG. 5, $K_{rel}^{-}L^*/L=3.09 \times 10^{-8}/45. \times 10^{-8}=0.0687$, so that $K^{3G8}=0.0687 \times 7.5 \times 10^8=5.1 \times 10^7 M^{-1}$. These association constants for 3G8 and 3G8-FITC fall in the same range as corresponding constants for 1D3 and 1D3-FITC.

Figure 7:
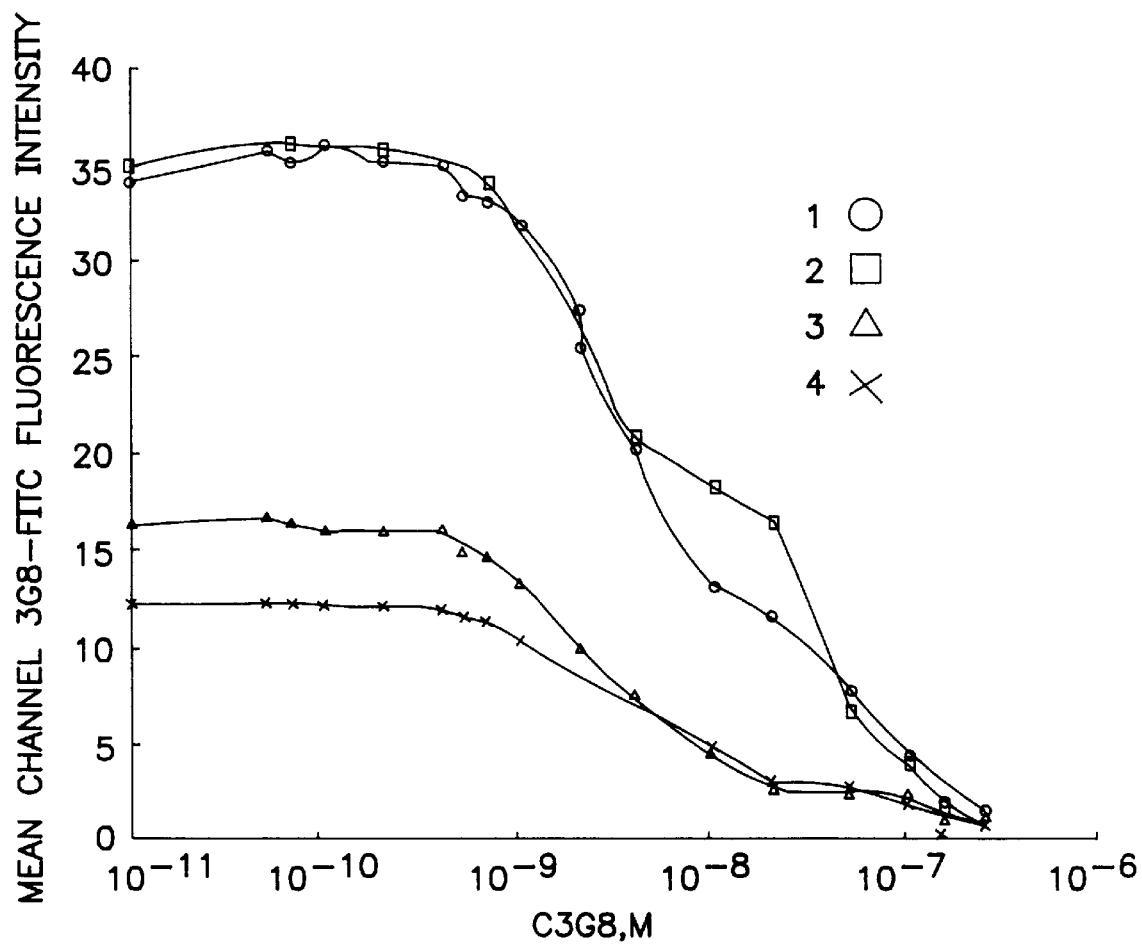
FIG. 7 graphically shows the linear-log dependence of mean channel 3G8-FITC fluorescence intensity on molar concentration of anti-3G8 antibody in competitive binding runs with four blood donors.

We have also run competitive binding trials of 3G8/3G8-FITC and 1D3/1D3-FITC in the absence of the second marker, KC56-PE. Samples were prepared in a similar way by mixing 10 µL of suitably diluted 3G8 antibody solutions containing 0.0010 to 5.0 µg of antibody in 1×PBS buffer solution with 100 µL whole blood for 60 minutes; then, further adding a constant 10 µL volume of 0.1 µg/µL 3G8-FITC marker to each trial and mixing for another 60 minutes. The samples were then treated on a COULTER Q-PREP to lyse rbcs and quench, and run on the COULTER Profile II flow cytometer to obtain mean channel 3G8-FITC fluorescence intensities on neutrophils. The results are shown in FIG. 7 for four blood donors, two medium and two low 3G8-FITC intensity donors. The two dim donors show no definite, measurable initial rise in fluorescence intensity at low concentrations of 3G8 antibody in the competitive binding trials. Both of the medium intensity donors showed an initial rise in 3G8-FITC intensity which intersected with the intensity of the controls without any 3G8 antibody at about 0.5 nM 3G8 concentration, yielding a soluble 3G8 antigen concentration of 0.5×2×120/100=1.2 nM. With a constant 3G8-FITC concentration of 51 nM in each sample and concentrations of 3G8 antibody at the half-titration points in runs 1, 2, 3, and 4 of 5.8, 1.2, 3.0, and 5.0 nM, the $K_{rel}(=L^*/L=K^L/K^{L*})$ values were calculated as 8.8, 4.2, 17., and 10., respectively, yielding constants for unlabelled 3G8 antibody binding that are higher for these donors than binding constants for labelled 3G8-FITC binding by a factor between 4.2 and 17. Thus, the presence of a large amount of soluble 3G8 antigen affected the apparent position of the half-titration point in FIG. 5 by extending it towards higher 3G8 antibody concentrations and was responsible for the lower unlabelled 3G8 antibody binding constant that was calculated in the previous competitive binding run. Corrected for the amount of 3G8 antibody that reacted with soluble antigen, the $K^{3G8}$ value was 20% higher, but still a factor of 0.081 times lower than the value of $K^{3G8-FITC}$. Similar apparent, low binding constants, about 2 to 7% lower, were calculated for 1D3 antibody from competitive binding data for 1D3/1D3-FITC due to the presence of soluble 1D3 antigen.

EXAMPLE 6

Competitive Binding of KC48/KC48-FITC (KC56-PE) to Granulocytes

Other unlabelled and labelled monoclonal antibodies, KC48 (anti-CD15), were used to compare the binding equilibrium data obtained with 1D3/1D3-FITC (KC56-PE) and whole blood. In particular, the beginning of the binding curve at low unlabelled antibody concentrations needs to be verified with monoclonal antibodies whose antigens are not normally shed in whole blood. Thus, a run, similar to those carried out with 1D3 antibody, was performed for KC48/KC48-FITC in which the amount of KC48-FITC was held constant at 4 µg. The results are displayed in Table XXVI.

TABLE XXVI

Mean channel KC48-FITC fluorescence intensities per aliquot of unmarked KC48 added to 100 µL whole blood; values in parentheses are standard deviations (SD).

| µg KC48 antibody | mean channel KC48-FITC fluorescence intensity | | | |
|---|---|---|---|---|
| | trial 1 | trial 2 | trial 3 | mean |
| .040 | 42.12(18.84) | 50.52(24.53) | 43.30(19.64) | 45.31 |
| .080 | 45.63(23.24) | 43.94(20.92) | 44.12(20.93) | 44.56 |
| .160 | 43.60(20.85) | 45.15(20.72) | 48.29(22.21) | 45.68 |
| .400 | 41.13(17.55) | 44.22(19.92) | 45.40(18.96) | 43.58 |
| .800 | 42.00(18.21) | 46.38(20.26) | 40.50(17.63) | 42.96 |
| 2.00 | 38.04(16.24) | 37.00(16.77) | 42.51(18.30) | 39.18 |
| 4.00 | 34.29(15.40) | 37.70(16.83) | 34.97(17.60) | 35.65 |
| 8.00 | 32.98(16.48) | 32.55(14.91) | 28.34(12.35) | 31.29 |
| 12.0 | 28.18(13.19) | 25.55(11.26) | 23.80(10.76) | 25.84 |
| 16.0 | 32.45(21.25) | 23.42(10.47) | 28.88(12.86) | 28.25 |
| 20.0 | 22.11(12.52) | 22.28(10.53) | 20.45(9.61) | 21.61 |
| 40.0 | 11.34(5.71) | 15.99(7.81) | 17.64(8.54) | 14.99 |
| 100. | 13.80(8.05) | 9.987(4.637) | 13.95(7.30) | 12.58 |
| 200. | 6.365(3.264) | 5.015(2.244) | 9.329(5.453) | 6.903 |
| 300. | 6.055(3.023) | 5.001(2.463) | 6.320(3.756) | 5.792 |
| 400. | 4.695(2.097) | 4.732(2.066) | 4.631(2.089) | 4.686 |
| control | 46.52(24.11) | 51.62(26.86) | 51.82(26.54) | 49.99 |

A plot of KC48-FITC intensity versus total concentration of KC48 antibody in mol/L is shown in FIG. 4. There is no initial rise in intensity to a maximum above the intensity of the control at low titers of KC48 antibody; in fact, the intensity is lower than that of the control by about five mean channels. The initial plateau in the graph is followed by an elongated, sigmoidal curve having a very short log-linear portion in the region, 8 to 30 µg KC48 antibody. The percentage inhibition referenced to the maximum intensity was calculated for each titer point and is shown in Table XXVII.

TABLE XXVII

Percentage inhibition data for KC48/KC48-FITC binding.

| µg KC48 antibody | conc KC48, M × $10^8$ | KC48-FITC intensity | % inhibition |
|---|---|---|---|
| .160 | .157 | 45.68 | 0 |
| .400 | .392 | 43.58 | 4.60 |
| .800 | .784 | 42.96 | 5.95 |
| 2.00 | 1.96 | 39.18 | 14.2 |
| 4.00 | 3.92 | 35.65 | 21.9 |
| 8.00 | 7.84 | 31.29 | 31.5 |
| 12.0 | 11.8 | 25.84 | 43.4 |
| 16.0 | 15.7 | 28.25 | 38.1 |
| 20.0 | 19.6 | 21.61 | 52.7 |
| 40.0 | 39.2 | 14.99 | 67.2 |
| 100. | 98.0 | 12.58 | 72.5 |
| 200. | 196. | 6.903 | 84.9 |
| 300. | 294. | 5.792 | 87.3 |
| 400. | 392. | 4.686 | 89.7 |

The half-titration point in the graph plotted on probability paper (FIG. 5) was located at about 17.2 µg ($16.9 \times 10^{-8}$M) KC48 antibody, much greater than the constant amount of KC48-FITC, 4 µg ($3.86 \times 10^{-8}$M), in each sample. The affinity of KC48-FITC was about 4.4× that of KC48, from calculation of the relative equilibrium constant as $K_{rel}=K^L/K^{L^*-}L^*/L=0.228$ at the half-titration point.

EXAMPLE 7

Competitive Binding of T4/T4-PE(T8-FITC) to CD4+ Lymphocytes

A competitive binding run, similar to runs with 1D3/1D3-FITC, was carried out by mixing a constant amount, 10 $\mu$L, of dual marker containing 0.28 $\mu$g T4-PE and 0.14 $\mu$g T8-FITC and 10 $\mu$L of variable amounts (1/100 to 2× the standard amount of 0.28 $\mu$g) of unmarked T4 antibody with 100 $\mu$L of whole blood. The mixtures were analyzed by flow cytometry after mixing for one hour after each component addition. Also, variable titers of the dual marker in the absence of unmarked T4 antibody were mixed with whole blood and analyzed by flow cytometry. The mean channel T4-PE fluorescence intensities are displayed in Table XXVIII.

TABLE XXVIII

Mean channel T4-PE fluorescence intensities per aliquot of unmarked T4 antibody added to 100 $\mu$L whole blood.

| $\mu$g T4 | conc T4, M × $10^9$ | mean channel intensity |
|---|---|---|
| .0028 | .146 | 4.142(1.099) |
| .0056 | .292 | 4.516(1.132) |
| .0112 | .583 | 2.401(0.632) |
| .028 | 1.46 | 1.468(0.352) |
| .056 | 2.92 | 1.578(0.399) |
| .14 | 7.29 | .65 |
| .28 | 14.58 | .16 |
| .56 | 29.16 | .16 |
| control | | 8.323 |

When the above data were plotted on linear-log paper (intensity versus T4 concentration), a half-titration point at 0.23×10$^{-9}$M was established. Results of the analyses of the marker titration data are shown in Table XXIX.

TABLE XXIX

Binding data analysis, T4-PE only.

| $\mu$L, dual marker | $c_{tot}$, M × $10^9$ | intensity | $\theta_2$ | $\theta_2/(1-\theta_2)$ |
|---|---|---|---|---|
| .010 | .00467 | .15 | .0172 | .0175 |
| .025 | .0117 | 1.841(0.443) | .2118 | .2687 |
| .050 | .0234 | 3.700(0.876) | .4256 | .7409 |
| .075 | .0351 | 5.110(1.261) | .5878 | 1.423 |
| .100 | .0467 | 5.453(1.370) | .6272 | 1.683 |
| .250 | .117 | 7.344(2.294) | .8447 | 5.439 |
| .750 | .351 | 7.618(2.335) | .8762 | 7.077 |
| 1.00 | .467 | 7.747(2.448) | .8911 | 8.183 |
| 5.00 | 2.34 | 8.212(2.961) | .9446 | 17.05 |
| 10.0 | 4.67 | 8.694(3.249) | 1.000 | — |
| 20.0 | 9.34 | 8.493(4.142) | — | — |
| 30.0 | 14.01 | 7.585(5.311) | — | — |
| 40.0 | 18.68 | 6.686(5.688) | — | — |
| 50.0 | 23.35 | 5.642(5.471) | — | — |

An initial estimate of K=5×10$^{10}$M$^{-1}$ was obtained from the slope of a $\theta_2/(1-\theta_2)$ versus $c_{tot}$ plot at low titers of dual marker. The best fit for titers between 0.025 and 1.00 $\mu$L was obtained for a binding constant, K=7.5×10$^{10}$M$^{-1}$, which gave an average $c_{sat}$=3.78(0.96)×10$^{-11}$M and a total no. of receptors=3.41×10$^9$. Therefore, for this donor with 1.33×10$^5$ L×0.383=5.1×10$^4$ CD4+ lymphocytes per 100 $\mu$L of whole blood, the number of receptors per CD4+ cell was 6.7(1.7) ×10$^4$.

Further, the binding constant for unlabelled T4 antibody can be calculated as follows, $$\begin{aligned} K_{T4} &= K^{L*}([L^*]/[L]) \\ &= 7.5 \times 10^{10}(.583 \times 10^{-8} - 1/2(.00375 \times 10^{-8}))/ \\ &\quad (.023 \times 10^{-8} - 1/2(.00375 \times 10^{-8})) \\ &= 2.1 \times 10^{12} M^{-1}, \end{aligned}$$

where the total concentrations, 5.83×10$^{-9}$ and 2.3×10$^{-10}$M, of T4-PE and T4 antibody, respectively, at 50% inhibition were modified by the small amount of each (½ $c_{sat}$) on the cell surface to obtain the values of [L*] and [L]. The affinity of T4 was 25× that of T4-PE, as calculated from expressions for the relative affinity constant as follows, $K_{rel}=K^L/K^{L^*-}L^*/L=25$ at the half-titration point.

Another competitive binding run was carried out with reversed roles of unlabelled/labelled antibody. 10 $\mu$L of various dilutions of T4-PE containing 0.0028 to 1.4 $\mu$g of T4-PE and a constant amount (0.14 $\mu$g) of T8-FITC were mixed first with 100 $\mu$L whole blood for one hour. Then, a constant 10 $\mu$L titer of T4 antibody (0.0028 $\mu$g) and sufficient 1×PBS solution to make a constant total volume of 160 $\mu$L for each sample were added and mixed for a second one hour period. Also, a parallel set of samples were prepared with variable amounts of dual marker, T4-PE/T8-FITC and 100 $\mu$L whole blood. Samples were Q-PREPed and run on the flow cytometer. The mean channel T4-PE fluorescence intensities in the competitive antibody run are shown in Table XXX.

TABLE XXX

Competitive T4-PE/T4 binding data.

| $\mu$g T4-PE | conc T4-PE, M × $10^9$ | mean channel intensity |
|---|---|---|
| .0028 | .0438 | 3.046(0.688) |
| .0056 | .0876 | 3.558(0.866) |
| .014 | .219 | 6.099(1.485) |
| .028 | .438 | 6.836(1.634) |
| .070 | 1.09 | 7.351(1.699) |
| .14 | 2.19 | 8.039(2.080) |
| .21 | 3.29 | 8.952(3.272) |
| .28 | 4.38 | 7.671(2.174) |
| .56 | 8.76 | 7.671(2.417) |
| .84 | 13.1 | 8.248(4.066) |
| 1.12 | 17.5 | 7.529(4.564) |
| 1.40 | 21.9 | 7.154(5.036) |

The half-titration point in a linear-log graph of mean channel intensity versus concentration of T4-PE was located at 2.0×10$^{-10}$M so that $K_{rel}$=[L*]/[L]$^-$L*/L=2.0×10$^{-10}$/1.09× 10$^{-10}$=1.8 at the half-titration point. Analyses of the T4-PE marker only titration data gave the following results in Table XXXI.

TABLE XXXI

Binding data for T4-PE alone.

| $\mu$L, dual marker | $c_{tot}$, M × $10^9$ | intensity | $\theta_2$ | $\theta_2/(1-\theta_2)$ |
|---|---|---|---|---|
| .010 | .00438 | .28 | .0266 | .0273 |
| .025 | .0110 | .60 | .0570 | .0604 |
| .050 | .0219 | 1.396(0.315) | .1327 | .1530 |
| .075 | .0329 | 2.638(0.648) | .2508 | .3348 |
| .100 | .0438 | 3.590(0.821) | .3413 | .5181 |

TABLE XXXI-continued

Binding data for T4-PE alone.

| μL, dual marker | $c_{tot}$, M × $10^9$ | intensity | $\theta_2$ | $\theta_2/(1-\theta_2)$ |
|---|---|---|---|---|
| .500 | .219 | 7.767(1.856) | .7383 | 2.821 |
| .750 | .329 | 7.447(1.917) | .7073 | 2.423 |
| 1.00 | .438 | 8.487(2.381) | .8067 | 4.173 |
| 2.00 | .876 | 9.118(2.525) | .8667 | 6.502 |
| 5.00 | 2.19 | 9.398(2.979) | .8933 | 8.372 |
| 10.0 | 4.38 | 10.47(3.21) | .9952 | 207.3 |
| 20.0 | 8.76 | 10.52(3.55) | 1.000 | — |

The slope of a $\theta_2/(1-\theta_2)$ versus $c_{tot}$ plot at low titers between 0.025 and 0.500 μL of dual marker gave K=1.3× $10^{10}M^{-1}$ as an initial estimate. Further adjustment of the K value gave a best fit for K=1.5×$10^{10}M^{-1}$ for an average $c_{sat}$=7.03(3.88)×$10^{-11}$M and a total number of receptors of 6.77×$10^9$. Therefore, for this donor with 1.42×$10^5$ L×0.544= 7.7×$10^4$ CD4+ lymphocytes per 100 μL of whole blood, the number of receptors per CD4+ cell was 8.8(4.8)×$10^4$. Furthermore, for this donor the binding constant for unlabelled T4 antibody was calculated as, $$K^{T4}=K^{L^*}(L^*/L)=1.5\times10^{10}(1.8)=2.7\times10^{10}M^{-1}.$$

For PE derivatives, steric hindrance may play the most important role in modifications to monoclonal antibody-cell surface antigen binding. If a single PE molecule on a relatively small IgG antibody can cause some steric blocking in T4-PE-antigen binding, this would explain the higher K values for unlabelled T4 as opposed to T4-PE. For 1D3-PE, however, the higher K was obtained for labelled 1D3 as with 1D3-FITC. Since 1D3 is a pentameric IgM antibody and since each molecule of 1D3 is attached to at most one PE molecule, no steric blocking of antibody-antigen binding is expected.

EXAMPLE 8

Equilibrium and Competitive Binding of T3/T3-FITC(T8-PE) to T Lymphocytes in Whole Blood Various titers of dual marker, T3-FITC/T8-PE, were mixed with whole blood for one hour, followed by Q-PREP, and then run on the COULTER Profile II flow cytometer. The mean channel T3-FITC (F/P=3.71) fluorescence intensities are listed in Table XXXII for three donors.

TABLE XXXII

Binding data for T3-FITC alone.

| μL dual marker | $c_{tot}$, T3-FITC, M × $10^8$ | T3-FITC mean channel fluorescence intensity | | |
|---|---|---|---|---|
| | | donor 1 | donor 2 | donor 3 |
| .010 | .0041 | .11 | .11 | .12 |
| .020 | .0082 | .12 | .11 | .14 |
| .040 | .0164 | .17 | .17 | .23 |
| .067 | .0273 | .60 | .65 | .38 |
| .100 | .0410 | .95 | .90 | .80 |
| .200 | .0820 | .60 | .60 | .55 |
| .400 | .164 | 4.260(1.700) | 4.040(1.677) | 3.685(1.571) |
| 1.00 | .410 | 6.290(2.390) | 6.459(2.444) | 6.041(2.423) |
| 2.00 | .820 | 7.759(2.874) | 7.390(2.874) | 7.270(2.852) |
| 5.00 | 2.05 | 7.903(2.932) | 8.838(3.325) | 8.200(3.163) |
| 10.0 | 4.10 | 8.768(3.180) | 10.23(3.71) | 9.024(3.592) |

TABLE XXXII-continued

Binding data for T3-FITC alone.

| μL dual marker | $c_{tot}$, T3-FITC, M × $10^8$ | T3-FITC mean channel fluorescence intensity | | |
|---|---|---|---|---|
| | | donor 1 | donor 2 | donor 3 |
| 20.0 | 8.20 | 10.67(4.38) | 10.23(4.55) | 9.059(4.542) |
| 30.0 | 12.3 | 10.77(5.13) | 9.986(5.739) | 9.022(5.197) |
| 40.0 | 16.4 | 10.89(5.44) | 10.14(5.91) | 8.940(5.564) |
| 50.0 | 20.5 | 10.84(5.81) | 9.974(6.317) | 8.874(5.950) |

Initial estimates of K and n values from the slopes of $\theta_2/(1-\theta_2)$ versus $c_{total}$ and the corresponding log-log plots gave 3.3×$10^8$, 4.3×$10^8$, 5.1×$10^8M^{-1}$ and 1.1, 1.2, 1.2, respectively, for donors 1, 2, and 3. Binding data analyses were then carried out in the usual way to produce optimized K values of 4.5×$10^8$, 5.0×$10^8$, and 5.5×$10^8M^{-1}$ and the results in Table XXXIII.

TABLE XXXIII

Total CD3 receptor concentrations and receptor/cell ratios.

| Sample | $c_{sat}$, M × $10^9$ | Sample Vol, L | Total no. Receptors | No. CD3 + Cells | Receptors/ CD3 + Cell |
|---|---|---|---|---|---|
| Donor 1 | 1.95(1.03) | 1.50 × $10^{-4}$ | 1.76 × $10^{11}$ | 2.5 × $10^5$ | 7.0(3.7) × $10^5$ |
| Donor 2 | 1.64(.80) | 1.50 × $10^{-4}$ | 1.48 × $10^{11}$ | 1.9 × $10^5$ | 7.8(3.8) × $10^5$ |
| Donor 3 | .801(.161) | 1.50 × $10^{-4}$ | 7.23 × $10^{10}$ | 1.1 × $10^5$ | 6.6(1.3) × $10^5$ |

The CD3+ cells were enumerated by obtaining the number of lymphocytes/100 μL of whole blood on the COULTER STKS 2B hematology analyzer and then using T3-FITC/KC56-PE dual marker to determine the percentage of CD3+ cells in the lymphocyte population by flow cytometry. The $K^{T3-FITC}$ values closely resemble those (6.4×$10^8$ and 5.0×$10^8M^{-1}$ at 12° and 36° C., respectively) previously measured for OKT3-FITC on washed peripheral blood mononuclear cells; however, the number of CD3+ receptors per T cell is about 5 to 10 times larger here than in previous work (12.9×$10^4$ at 12° C. and 7.8×$10^4$ at 36° C.). The processing of cells by three sequential washings in the work of Oonishi et al. [30] may have activated the T cells to shed receptors and show lower figures for CD3+ receptors/cell.

Competitive binding runs were also done by mixing a constant amount, 10 μL, of dual marker containing 1.0 μg T3-FITC/0.20 μg T8-PE and 10–50 μL of variable dilutions (1/100 to 5× the standard amount of 1.0 μg) of unmarked T3 antibody with 100 μL of whole blood for one hour after addition of each component. The mixtures were then Q-PREPed and analyzed by flow cytometry to obtain total CD3+ lymphocyte mean channel intensities for the same three donors as listed in Table XXXIV.

TABLE XXXIV

Competitive T3/T3-FITC binding data.

| μg T3 marker | conc T3, M × 10⁸ | T3-FITC mean channel fluorescence intensity | | |
|---|---|---|---|---|
| | | donor 1 | donor 2 | donor 3 |
| .01 | .0416 | 8.645(3.014) | 8.545(2.991) | 7.248(2.765) |
| .02 | .0832 | 7.760(2.793) | 5.879(2.140) | 7.034(2.635) |
| .04 | .166 | 4.000(1.472) | 6.442(2.318) | 3.184(1.179) |
| .10 | .416 | 2.451(0.816) | 2.288(0.679) | 2.553(0.880) |
| .20 | .832 | .45 | .75 | .70 |
| .50 | 2.08 | .40 | .20 | .60 |
| 1.0 | 4.16 | .28 | .20 | .50 |
| 2.0 | 8.32 | .30 | .30 | .50 |
| 3.0 | 12.5 | .30 | .20 | .40 |
| 4.0 | 16.6 | .25 | .20 | .40 |
| 5.0 | 20.8 | .20 | .20 | .40 |
| 0.0 | control | 8.768 | 10.23 | 9.024 |

A linear-log plot of mean channel intensity versus $c_{total}$ (T3) at a constant T3-FITC concentration of $4.10 \times 10^{-8}$M gave half-titration points of $1.7 \times 10^{-9}$, $1.6 \times 10^{-9}$, and $1.4 \times 10^{-9}$M T3 antibody for donors 1, 2, and 3. Thus, respective values of $K_{rel}^{-} L^*/L = 24.12$, 25.62, and 29.28 were calculated to yield $K^{T3} = K^{T3-FITC} \times K_{rel} = 1.1 \times 10^{10}$, $1.3 \times 10^{10}$, and $1.6 \times 10^{10}$M$^{-1}$. In these runs the affinity of native T3 antibody was greater by more than an order of magnitude than the affinity of its FITC derivative for cell surface CD3 antigen. This ordering is the reverse of that established for IgM antibodies, 1D3 and KC48, and the IgG1 antibody, 3G8, and their FITC derivatives. Possibly, the relatively low number of FITC groups per T3antibody molecule (F/P=3.71) and/or the additional complexity of the T cell antigen receptor structure, which can be induced to a higher state of activation-proliferation by chelated anti-CD3 antibody [47], contribute to the observed reversal in T3/T3-FITC antibody affinities.

Furthermore, no evidence of any shed CD3 antigen was detected at low titers of T3 antibody in the T3/T3-FITC competitive binding runs. However, the three titration runs with T3-FITC all showed a sudden increase in fluorescence intensity from below one mean channel in the autofluorescence region to about four mean channels above the discriminator line between 0.200 and 0.400 μL titers of dual marker or between 0.040 and 0.10 μg of T3-FITC. This might indicate the presence of soluble CD3 antigen being titrated by T3-FITC at low concentrations but not being detected on CD3+ cell surfaces by flow cytometry.

REFERENCES

1. HIGH-SENSITIVITY CYTOFLUOROMETRIC QUANTITATION OF LECTIN AND HORMONE BINDING TO SURFACES OF LIVING CELLS, B. Bohn, Exp. Cell Res. 103, 39 (1976).
2. APPLICATION OF FLOW CYTOFLUOROMETRY TO LIGAND BINDING STUDIES ON LIVING CELLS: PRACTICAL ASPECTS AND RECOMMENDATIONS FOR CALIBRATION AND DATA PROCESSING, B. Bohn and W. Manske, Acta Pathol. Microbiol. Scand., Sect. A, Suppl 274, 227 (1980).
3. FLOW CYTOMETRY: A NOVEL APPROACH FOR THE QUANTITATIVE ANALYSIS OF RECEPTOR-LIGAND INTERACTIONS ON SURFACES OF LIVING CELLS, B. Bohn, Molec. Cell. Endocrinol. 20, 1 (1980).
4. FLUORESCENT MICROBEAD STANDARDS, Flow Cytometry Standards Corporation, Research Triangle Park, N.C. 27709, 1988.
5. STANDARDS FOR FLOW CYTOMETRY, M. J. Fulwyler in Flow Cytometry and Sorting, M. R. Melamed, P. F. Mullaney, M. L. Mendelsohn, eds., Wiley, New York, 1979, p.351.
6. Fc(IgG) RECEPTOR DISTRIBUTIONS IN HOMOGENEOUS AND HETEROGENEOUS CELL POPULATIONS BY FLOW MICROFLUOROMETRY, J. A. Titus, S. P. Sharrow, J. M. Connolly, D. M. Segal, Proc. Natl. Acad. Sci. USA 78, 519 (1981).
7. QUANTITATIVE IMMUNOFLUORESCENCE IN FLOW CYTOMETRY, J. Visser, J. Haaijman, B. Trask, in Immunofluorescence and Related Staining Techniques, W. Knapp, K. Holubat, G. Wick, eds., Elsevier, Amsterdam, 1978, p. 147.
8. FLOW ANALYZER AND SYSTEM FOR ANALYSIS OF FLUID WITH PARTICLES, G. Bolz and S. E. De Forest, U.S. Pat. No. 4,338,024 issued Jul. 6, 1982.
9. METHOD OF ANALYZING THE DISTRIBUTION OF A REAGENT BETWEEN PARTICLES AND LIQUID IN A SUSPENSION, F. H. Deindoerfer, J. R. Gangwer, U.S. Pat. No. 4,476,231 issued Oct. 9, 1984.
10. ANTIBODY AFFINITY: THERMODYNAMIC ASPECTS AND BIOLOGICAL SIGNIFICANCE, M. W. Steward and J. Steensgaard, CRC Press, Boca Raton, Fla., 1983.
11. FLUORESCEIN HAPTEN: AN IMMUNOLOGICAL PROBE, E. W. Voss, Jr., CRC Press, Boca Raton, Fla., 1984.
12. A QUANTITATIVE IMMUNOCHEMICAL MEASURE OF THE PRIMARY INTERACTION BETWEEN I*BSA AND ANTIBODY, R. S. Farr, J. Infect. Dis. 103, 239 (1958).
13. RADIOIMMUNOASSAY: A PROBE FOR THE FINE STRUCTURE OF BIOLOGIC SYSTEMS, R. S. Yalow, Science 200, 1236 (1978).
14. AMPLIFIED FLOW-CYTOMETRIC SEPARATION-FREE FLUORESCENCE IMMUNOASSAYS, G. C. Saunders, J. H. Jett, and J. C. Martin, Clin. Chem. 31, 2020 (1985).
15. FLOW CYTOMETER MEASUREMENT OF BINDING ASSAYS, G. C. Saunders, U.S. Pat. No. 4,665,020 issued May 12, 1987.
16. FLOW CYTOMETRIC COMPETITIVE BINDING ASSAY FOR DETERMINATION OF ACTINOMYCIN-D CONCENTRATIONS, G. C. Saunders, J. C. Martin, J. H. Jett, and A. Perkins, Cytometry 11, 311 (1990).
17. A FLUORESCENCE IMMUNOASSAY FOR SOLUBLE ANTIGENS EMPLOYING FLOW CYTOMETRIC DETECTION, P. J. Lisi, C. W. Huang, R. A. Hoffman, and J. W. Teipel, Clinica Chimica Acta 120, 171 (1982).
18. SUGAR COMPETITION ASSAYS REVEAL HIGH AFFINITY RECEPTORS FOR ERYTHRINA CRISTIGALLI LECTIN ON FELINE MONOCYTES, C. E. Whitehurst, N. K. Day, and N. Gengozian, J. Immunol. Methods 131, 15 (1990).
19. A METHOD OF PURIFYING T LYMPHOCYTES FROM PERIPHERAL BLOOD USING THE PLANT LECTIN FROM PISUM SATIVUM, C. E. Whitehurst, N. K. Day, and N. Gengozian, J. Immunol. Methods 175, 189 (1994).
20. LINKED FUNCTIONS AND RECIPROCAL EFFECTS IN HEMOGLOBIN: A SECOND LOOK, J. Wyman, Jr., Adv. Protein Chem. 19, 223 (1964).

21. SURFACE RAMAN INVESTIGATION OF THE SORPTION OF DABSYL ASPARTATE AND POLYVINYLPYRROLIDONE ON COLLOIDAL SILVER IN ETHANOL, A. Lepp and O. Siiman, J. Coll. Interface Sci. 105, 325 (1985).

22. A METHOD FOR INVESTIGATING DISSOCIATION EQUILIBRIA IN SOLUTIONS AND ITS APPLICATION TO THE STUDY OF AQUEOUS POTASSIUM MERCURI-IODIDE SOLUTIONS, H. M. Dawson, J. Chem. Soc. 95, 870 (1909); Chem. Abstr. 3, 2080 (1909).

23. THE DETERMINATION OF STABILITY CONSTANTS, F. J. C. Rossotti and H. Rossotti, McGraw-Hill, New York, N.Y., 1961, Chap. 4, Section 4–6, pp. 78–81.

24. CALCULATION OF AVERAGE ANTIBODY AFFINITY IN ANTIHAPTEN SERA FROM DATA OBTAINED BY COMPETITIVE RADIOIMMUNOASSAY, R. Muller, J. Immunol. Methods 34, 345 (1980).

25. KINETIC ANALYSIS OF MONOCLONAL ANTIBODY-ANTIGEN INTERACTIONS WITH A NEW BIOSENSOR BASED ANALYTICAL SYSTEM, R. Karlsson, A. Michaelson, and L. Mattson, J. Immunol. Methods 145, 229 (1991).

26. SURFACE-ENHANCED RAMAN SCATTERING BY CITRATE ON COLLOIDAL SILVER, O. Siiman, L. A. Bumm, R. Callaghan, C. G. Blatchford, M. Kerker, J. Phys. Chem. 87, 1014 (1983).

27. ANALYSIS OF LIGAND-RECEPTOR INTERACTIONS WITH THE FLUORESCENCE ACTIVATED CELL SORTER, L. A. Sklar and D. A. Finney, Cytometry 3, 161 (1982).

28. A. N. Barclay, M. L. Birkeland, M. H. Brown, A. D. Beyers, S. J. Davis, C. Somoza, A. F. Williams, THE LEUKOCYTE FACTS BOOK, Academic Press, San Diego, Calif., 1993, p. 21.

29. INTERLABORATORY STUDY OF CELLULAR FLUORESCENCE INTENSITY MEASUREMENTS WITH FLUORESCEIN-LABELED MICROBEAD STANDARDS, R. F. Vogt, Jr., G. D. Cross, D. L. Phillips, L. O. Henderson, and W. H. Hannon, Cytometry 12, 525 (1991).

30. FLOW CYTOMETRIC STUDIES OF THE BINDING OF MONOCLONAL ANTIBODIES OKT3, OKT4, AND OKT8, T. Oonishi, K. Sakashita, and N. Uyesaka, J. Immunol. Methods 115, 159 (1988).

31. PRESERVED, NON-INFECTIOUS CONTROL CELLS FOR USE IN THE IDENTIFICATION OF A DISEASE THROUGH BLOOD TESTING, J. A. Maples, R. H. Raynor, O. Siiman, M. J. Stiglitz, and S. F. Healy, U.S. Pat. No. 5,342,754 issued Aug. 30, 1994.

32. PRINCIPLES OF COLLOID AND SURFACE CHEMISTRY, 2nd ed., P. C. Hiemenz, Marcel Dekker, New York, N.Y., 1986.

33. PHYSICAL CHEMISTRY OF SURFACES, 4th ed., A. W. Adamson, Wiley-Interscience, New York, N.Y., 1982.

34. MONOCLONAL ANTIBODY SPECIFIC TO NEUTROPHILS, J. D. Griffin, U.S. Pat. No. 4,931,395 issued Jun. 5, 1990.

35. U.S. Ser. No. 07/961,157, filed Oct. 15, 1992, and entitled POLYMERIC PARTICLES HAVING A BIODEGRADABLE GELATIN OR AMINODEXTRAN COATING AND PROCESSES FOR MAKING SAME, O. Siiman, A. Burshteyn, and R. Gupta, which is a continuation of U.S. Pat. No. 5,169,754, issued Dec. 8, 1992.

36. U.S. Pat. No. 4,752,563.

37. BIOCHEMISTRY AND PHYSIOLOGY OF THE NEUTROPHIL, S. W. Edwards, Cambridge University Press, 1994.

38. THE NEUTROPHIL, J. S. Abramson and J. G. Wheeler, eds., IRL Press at Oxford University Press, 1993.

39. A SOLUBLE FORM OF Fc$\gamma$RIII IS PRESENT IN HUMAN SERUM AND OTHER BODY FLUIDS AND IS ELEVATED AT SITES OF INFLAMMATION, H. B. Fleit, C. D. Kobasiuk, C. Daly, R. Furie, P. C. Levy, and R. O. Webster, Blood 79, 2721 (1992).

40. SOLUBLE Fc$\gamma$ RECEPTOR III IN HUMAN PLASMA ORIGINATES FROM RELEASE BY NEUTROPHILS, T. W. J. Huizinga, M. deHaas, M. Kleijer, J. H. Nuijens, D. Roos, and A. E. G. Kr. von dem Borne, J. Clin. Invest. 86, 416 (1990).

41. SURFACE EXPRESSION OF Fc$\gamma$ RECEPTOR III (CD16) ON CHEMOATTRACTANT-STIMULATED NEUTROPHILS IS DETERMINED BY BOTH SURFACE SHEDDING AND TRANSLOCATION FROM INTRACELLULAR STORAGE COMPARTMENTS, M. F. Tosi and H. Zakem, J. Clin. Invest. 90, 462 (1992).

42. ANTIBODIES-A LABORATORY MANUAL, E. Harlow and D. Lane, Cold Spring Harbor Laboratory, 1988, chap. 14.

43. STATISTICAL ANALYSIS IN CHEMISTRY AND THE CHEMICAL INDUSTRY, C. A. Bennett and N. L. Franklin, Wiley, 1967, p. 15, 91.

44. ANTIBODY STRUCTURE, D. R. Davies and S. Chacko, Accs. Chem. Res. 26, 421–427 (1993).

45. ANTIBODY-ANTIGEN COMPLEXES, E. A. Padlan, R. G. Landes Co., Austin, Tex., 1994.

46. THE STRUCTURE OF PROTEIN-PROTEIN RECOGNITION SITES, J. Janin and C. Chothia, J. Biol. Chem. 265, 16027–16030 (1990).

47. U.S. patent application entitled ANTI-CD3 ANTIBODY-AMINODEXTRAN CONJUGATES FOR INDUCTION OF T-CELL ACTIVATION AND PROLIFERATION, W. E. Bolton, J. A. Maples, O. Siiman, N. S. Kenyon, and C. G. Healy, Ser. No. 08/075,647, filed Jun. 11, 1993.

All publications cited in this specification are indicative of the level of skill of those in the art to which this application pertains. Each publication is individually incorporated herein by reference in the location where it is cited.

One skilled in the art will appreciate that although specific reagents and conditions are outlined in the following preparations and methods, modifications can be made which are meant to be encompassed by the spirit and scope of the invention. The preparations and methods, therefore, are provided to illustrate the invention. Such alternate means are to be construed as included within the intent and spirit of the present invention as defined by the following claims.

We claim:

1. A method for enumerating receptors on a formed body contained in a whole blood sample, said receptors being capable of binding to a marker, said method comprising the steps of:

(a) incubating a plurality of titers of said blood sample with predetermined amounts of the marker to produce a plurality of mixtures in which the marker concentration varies from mixture to mixture, over a range of between about 100% saturation and about 10% saturation;

(b) analyzing each mixture with excitation radiation to provide a first set of values, each value of said first set representing the mean channel intensity of the fluorescence or light scatter produced by the marker bound to the irradiated blood cells comprising an associated mixture; and (c) using said first set of values to compute the average number of receptors per formed body in said sample.

2. The method of claim 1, wherein step (b) is performed using a flow cytometer.

3. The method of claim 1, wherein the formed body is a biological cell, a bacterium, a virus, a parasite, or a colloidal particle.

4. The method of claim 1, wherein the marker consists of a label attached to a ligand.

5. The method of claim 4, wherein the label is a fluorescent label.

6. The method of claim 5, wherein the fluorescent label is fluorescein isothiocyanate or phycoerythrin.

7. The method of claim 4, wherein the label is an enhanced Raman label.

8. The method of claim 4, wherein the ligand is a monoclonal antibody, a polyclonal antibody, a lectin, a hormone, a growth factor, or a drug.

9. A method for enumerating receptors on a formed body contained in a whole blood sample, said receptors being capable of binding to a marker, said method comprising the steps of:

(a) incubating a plurality of titers of said blood sample with predetermined amounts of the marker to produce a plurality of mixtures in which the marker concentration varies from mixture to mixture, over a range of between about 100% saturation and about 10% saturation;

(b) analyzing each mixture with excitation radiation to provide a first set of values, each value of said first set representing the mean channel intensity of the fluorescence or light scatter produced by the marker bound to the irradiated blood cells comprising an associated mixture;

(c) using said first set of values to compute the average number of receptors per formed body in said sample by the following steps:

(i) obtaining a set of values for the fraction of receptor sites on targeted formed bodies that are occupied by marker by using the set of values obtained for said mean channel intensities by dividing each mean channel intensity by the mean channel intensity at saturation;

(ii) evaluating the saturation concentration of the marker on formed bodies by running a series of increasing titers until the intensity no longer changes, or reaches a maximum value;

(iii) plotting the fractional occupancy of surface receptor over one minus the fractional occupancy of surface receptor versus the total concentration of the marker, and obtaining an estimate of the specific binding constant from the slope of said plot;

(iv) calculating the solution concentration of the marker for each titer point using the binding equation;

(v) evaluating the surface concentration of the marker and saturation concentration for each titer point;

(vi) comparing the values obtained for the saturation concentration for all titer trials and minimizing their difference by adjustment of binding or association constant value;

(vii) obtaining the specific binding constant from the final adjusted association constant;

(viii) determining the total concentration of receptors and the total number of receptors by using said saturation concentration of marker;

(ix) determining the total number of targeted formed bodies by running the sample in a hematology analyzer; and (x) obtaining the number of receptors per formed body from the ratio of total number of receptors in (viii) to the total number of formed bodies.

10. The method of claim 9, wherein step (b) is performed using a flow cytometer.

11. The method of claim 9, wherein the formed body is a biological cell, a bacterium, a virus, a parasite, or a colloidal particle.

12. The method of claim 9, wherein the marker consists of a label attached to a ligand.

13. The method of claim 12, wherein the label is a fluorescent label.

14. The method of claim 13, wherein the fluorescent label is fluorescein isothiocyanate or phycoerythrin.

15. The method of claim 12, wherein the label is an enhanced Raman label.

16. The method of claim 12, wherein the ligand is a monoclonal antibody, a polyclonal antibody, a lectin, a hormone, a growth factor, or a drug.

17. A method for evaluating the specific binding constant of a marker, said method comprising the steps of:

(a) incubating a plurality of titers of blood samples with a predetermined amount of the marker to produce a plurality of mixtures in which the marker concentration varies from mixture to mixture, over a sufficient range between about 100% saturation and about 10% saturation;

(b) analyzing the mixtures with an instrument that measures light scatter and fluorescent emission of formed bodies, to provide a first set of values, each value of said first set representing the mean channel intensity of the fluorescence or light scatter produced by the marker bound to the irradiated blood cells comprising an associated mixture;

(c) using the set of values obtained from the mean channel intensities to calculate the specific binding constant by the following steps:

(i) obtaining a set of values for the fraction of receptor sites on targeted formed bodies that are occupied by the marker by using the set of values obtained for said mean channel intensities by dividing each mean channel intensity by the mean channel intensity at saturation;

(ii) evaluating the saturation concentration of marker on formed bodies by running a series of increasing titers until the intensity no longer changes or reaches a maximum value;

(iii) plotting the fractional occupancy of surface receptor over one minus the fractional occupancy of surface receptor versus the total concentration of the marker, and obtaining an estimate of the specific binding constant from the slope of said plot;

(iv) calculating the solution concentration of the marker for each titer point using the binding equation;

(v) evaluating the surface concentration of marker and saturation concentration for each titer point;

(vi) comparing the values obtained for the saturation concentration for all titer trials and minimizing their difference by adjustment of binding or association constant value; and (vii) obtaining the specific binding constant from the final adjusted association constant.

18. The method of claim 17, wherein the instrument of step (b) is a flow cytometer.

19. The method of claim 17, wherein the formed body is a biological cell, a bacterium, a virus, a parasite, or a colloidal particle.

20. The method of claim 17, wherein the marker consists of a label attached to a ligand.

21. The method of claim 20, wherein the label is a fluorescent label.

22. The method of claim 21, wherein the fluorescent label is fluorescein isothiocyanate or phycoerythrin.

23. The method of claim 20, wherein the label is an enhanced Raman label.

24. The method of claim 20, wherein the ligand is a monoclonal antibody, a polyclonal antibody, a lectin, a hormone, a growth factor, or a drug.

25. A method for analyzing receptors released from the surface of formed bodies contained in a whole blood sample, said receptors being capable of binding to a ligand, said method comprising the steps of:

(a) incubating a plurality of titers of labelled ligand with a predetermined amount of formed bodies in a whole blood sample, and maintaining a constant concentration of the labelled ligand;

(b) adding a plurality of titers of unlabelled ligand to the mixture in step (a) and incubating new mixtures containing a variable concentration of the unlabelled ligand;

(c) analyzing each mixture from step (b) with excitation radiation to provide a first set of values, each value of said first set representing the mean channel intensity of the fluorescence or light scatter produced by the labelled ligand bound to the irradiated blood cells comprising an associated mixture;

(d) identifying the concentration of the unlabelled ligand at which the mean channel intensity in the competitive binding trials is equal to the mean channel intensity of a control which contained no unlabelled ligand but had the same concentration of the labelled ligand and the same volume of a suspension of formed bodies; and (e) determining the concentration of receptors released from the surface of formed bodies into solution using the concentration of unlabelled ligand from step (d) by using an appropriate ligand-to-receptor binding ratio and a sample-to-blood volume factor.

26. The method of claim 25, wherein step (c) is performed using a flow cytometer.

27. The method of claim 25, wherein the formed body is a biological cell, a bacterium, a virus, a parasite, or a colloidal particle.

28. The method of claim 25, wherein the label is a fluorescent one.

29. The method of claim 28, wherein the fluorescent label is fluorescein isothiocyanate or phycoerythrin.

30. The method of claim 25, wherein the label is an enhanced Raman label.

31. The method of claim 25, wherein the ligand is a monoclonal antibody, a polyclonal antibody, a lectin, a hormone, a growth factor, or a drug.

32. A method for analyzing for receptors that have been released from the surface of formed bodies in a whole blood sample, said method comprising the steps of:

(a) incubating a plurality of titers containing a suitable concentration of labelled ligand with a predetermined amount of said sample to form labelled formed bodies, and maintaining a constant concentration of the labelled ligand;

(b) adding a plurality of titers containing a suitable concentration of the unlabelled ligand to the mixtures in step (a) and incubating new mixtures containing a variable concentration of the unlabelled ligand;

(c) analyzing the labelled formed bodies in mixtures in step (b) with excitation radiation to provide a first set of values, each value of said first set representing the mean channel intensity of the fluorescence or light scatter produced by the labelled ligand bound to the irradiated sample;

(d) obtaining the percent inhibition of the labelled ligand binding to receptors on formed bodies by the presence of the unlabelled ligand for each titer point, by using the mean channel intensities;

(e) obtaining a probability-log graphical representation of said percent inhibition as the logit function against the concentration of the unlabelled ligand for all titer points;

(f) identifying the concentration of the unlabelled ligand in the bimodal curve of said graphical representation at which a discontinuity in the slope of the curves is observed; and (g) using the concentration of unlabelled ligand in step (f) to determine the concentration of receptors released from the surface of formed bodies into solution by using an appropriate ligand-to-receptor binding ratio and a sample-to-blood volume factor.

33. The method of claim 32, wherein step (c) is performed using a flow cytometer.

34. The method of claim 32, wherein the formed body is a biological cell, a bacterium, a virus, a parasite, or a colloidal particle.

35. The method of claim 32, wherein the label is a fluorescent label.

36. The method of claim 35, wherein the fluorescent label is fluorescein isothiocyanate or phycoerythrin.

37. The method of claim 32, wherein the label is an enhanced Raman label.

38. The method of claim 32, wherein the ligand is a monoclonal antibody, a polyclonal antibody, a lectin, a hormone, a growth factor, or a drug.

39. A method for determining the specific binding constant of unlabelled ligand for receptors on formed bodies in a whole blood sample, said method comprising the steps of:

(a) incubating a plurality of titers of blood samples with a predetermined amount of labelled ligand to produce a plurality of mixtures in which the labelled ligand concentration varies from mixture to mixture, over a sufficient range between about 100% saturation and about 10% saturation;

(b) analyzing the mixtures with an instrument that measures light scatter and fluorescent emission of formed bodies, to provide a first set of values, each value of said first set representing the mean channel intensity of the fluorescence or light scatter produced by the labelled ligand bound to the irradiated blood cells comprising an associated mixture;

(c) using the set of values obtained from the mean channel intensities to calculate the specific binding constant of labelled ligand by the following steps:

(i) obtaining a set of values for the fraction of receptor sites on targeted formed bodies that are occupied by the labelled ligand by dividing each mean channel intensity by the mean channel intensity at saturation;
(ii) evaluating the saturation concentration of the labelled ligand formed bodies by running a series of increasing titers until the intensity no longer changes, or reaches a maximum value;
(iii) plotting the fractional occupancy of surface receptor over one minus the fractional occupancy of surface receptor versus the total concentration of the labelled ligand, and obtaining an estimate of the specific binding constant from the slope of said plot;
(iv) calculating the solution concentration of the labelled ligand for each titer point using the binding equation;
(v) evaluating the surface concentration of the labelled ligand and saturation concentration for each titer point;
(vi) comparing the values obtained for the saturation concentration for all titer trials and minimizing their difference by adjustment of binding or association constant value;
(vii) obtaining the specific binding constant of the labelled ligand from the final adjusted association constant;
(d) incubating a plurality of samples of the labelled ligand for a sufficient time, about 60 to about 120 minutes, with a fixed volume of suspension of formed bodies, in which a concentration of the labelled ligand which is close to but not above saturation is maintained constant;
(e) adding and incubating the unlabelled ligand for a sufficient time, about 60 to about 120 minutes, with mixtures of step (d), in which the concentration of the unlabelled ligand is varied over a sufficient range such that enough of the labelled ligand is displaced so as to obtain from 0 to 95–100% inhibition;
(f) analyzing the labelled formed bodies in mixtures from step (e) with an instrument that measures light scatter and fluorescent emission of formed bodies to obtain the mean channel intensities of the labelled formed bodies for each titer mixture of step (e);
(g) identifying the concentration of the unlabelled ligand at which the mean channel intensity in the competitive binding trials of step (e) reaches the half-titration point; and
(h) using said concentration of unlabelled ligand, the constant concentration of labelled ligand, and the specific binding constant determined for the labelled ligand to evaluate the specific binding constant of the unlabelled ligand by using the reciprocal relationship derived between specific binding constant and concentration of ligand at the half-titration point of competitive binding experiments.

40. The method of claim 39, wherein steps (b) and (f) are performed using a flow cytometer.

41. The method of claim 39, wherein the formed body is a biological cell, a bacterium, a virus, a parasite, or a colloidal particle.

42. The method of claim 39, wherein the label is a fluorescent label.

43. The method of claim 42, wherein the fluorescent label is fluorescein isothiocyanate or phycoerythrin.

44. The method of claim 39, wherein the label is an enhanced Raman label.

45. The method of claim 39, wherein the ligand is a monoclonal antibody, a polyclonal antibody, a lectin, a hormone, a growth factor, or a drug.

* * * * *